(12) United States Patent
Tsushima

(10) Patent No.: US 11,360,199 B2
(45) Date of Patent: *Jun. 14, 2022

(54) ULTRASOUND SIGNAL PROCESSING DEVICE, ULTRASOUND DIAGNOSTIC DEVICE

(71) Applicant: Konica Minolta, Inc., Tokyo (JP)

(72) Inventor: Mineo Tsushima, Kyoto-fu (JP)

(73) Assignee: KONICA MINOLTA, INC., Tokyo (JP)

( * ) Notice: Subject to any disclaimer, the term of this patent is extended or adjusted under 35 U.S.C. 154(b) by 319 days.

This patent is subject to a terminal disclaimer.

(21) Appl. No.: 16/599,317

(22) Filed: Oct. 11, 2019

(65) Prior Publication Data

US 2020/0037996 A1  Feb. 6, 2020

Related U.S. Application Data

(63) Continuation of application No. 15/067,858, filed on Mar. 11, 2016, now Pat. No. 10,470,745.

(30) Foreign Application Priority Data

Mar. 27, 2015  (JP) ................................ 2015-066483

(51) Int. Cl.
| A61B 8/00 | (2006.01) |
| G01S 7/52 | (2006.01) |
| G01S 15/89 | (2006.01) |
| G16H 30/20 | (2018.01) |
| A61B 8/08 | (2006.01) |

(52) U.S. Cl.
CPC ........ G01S 7/52046 (2013.01); A61B 8/4483 (2013.01); A61B 8/5207 (2013.01);
(Continued)

(58) Field of Classification Search
CPC ............ G01S 7/52046; G01S 15/8927; G01S 15/8997; G01S 7/52047; G01S 7/52095;
(Continued)

(56) References Cited

U.S. PATENT DOCUMENTS 10,470,745 B2 * 11/2019 Tsushima ............ G01S 7/52046
2015/0196273 A1   7/2015 Yamamoto
2016/0174938 A1   6/2016 Takano

FOREIGN PATENT DOCUMENTS

| JP | 2009240700 A | 10/2009 |
| WO | 2014/050885 A1 | 4/2014 |
| WO | 2015025655 A1 | 2/2015 |

OTHER PUBLICATIONS

M. Itou, et al.; Ultrasound diagnostic device; Corona Publishing Co., Ltd.; Aug. 2002; pp. 42-45 and partial English translation.
(Continued)

*Primary Examiner* — Joel Lamprecht
(74) *Attorney, Agent, or Firm* — Lucas & Mercanti, LLP

(57) ABSTRACT

An ultrasound signal processing device: performing events involving transmitting ultrasound towards a subject; receiving ultrasound reflection from the subject in response to each event; and generating a frame signal from sub-frame signals generated based on the ultrasound reflection. The device, in each event, causes a transmission aperture to transmit ultrasound focusing in the subject. A transmission aperture for one event differs in position, in a transducer element array direction, from a transmission aperture for a previous event by a shift amount of at least twice a transducer element width. The device, for each event, sets a target area which includes a position where transmitted ultrasound focuses and whose width in the transducer element array direction, at a depth where the transmitted ultrasound focuses, is equal to or greater than the shift amount. The device generates a sub-frame signal covering measurement points included in the target area.

14 Claims, 28 Drawing Sheets

(52) U.S. Cl.
CPC ...... *G01S 15/8927* (2013.01); *G01S 15/8997* (2013.01); *G16H 30/20* (2018.01); *G01S 7/52047* (2013.01); *G01S 7/52095* (2013.01)

(58) Field of Classification Search
CPC ... A61B 8/4483; A61B 8/5207; A61B 8/4444; A61B 8/5269; A61B 8/54; G16H 30/20; G16H 50/20
See application file for complete search history.

(56) References Cited

OTHER PUBLICATIONS

S.I. Nikolov, et al; Virtual ultrasound sources in high-resolution ultrasound imaging; Proc, SPIE—Progress in Biomedical Optics and Imaging, vol. 4687; 2002; pp. 395-405.

Extended European Search Report dated Aug. 8, 2016 from corresponding European Application No. 16161580.2; 11 pages.

Notice of Reasons for Refusal dated Apr. 24, 2018 from corresponding Japanese Patent Application No. 2015-066483 and English translation.

Office Action dated May 25, 2018 from corresponding Chinese Patent Application No. CN 201610169092.5 and English translation.

Examination dated Sep. 28, 2018 from corresponding European Application No. 16161580.2.

Notice of Reasons for Refusal dated Mar. 26, 2019 from corresponding Japanese Patent Application No. 2018-110178 and English translation.

CNIPA, Office Action of the corresponding Chinese patent application No. 201910613595.0, dated Jul. 5, 2021, with English translation.

\* cited by examiner

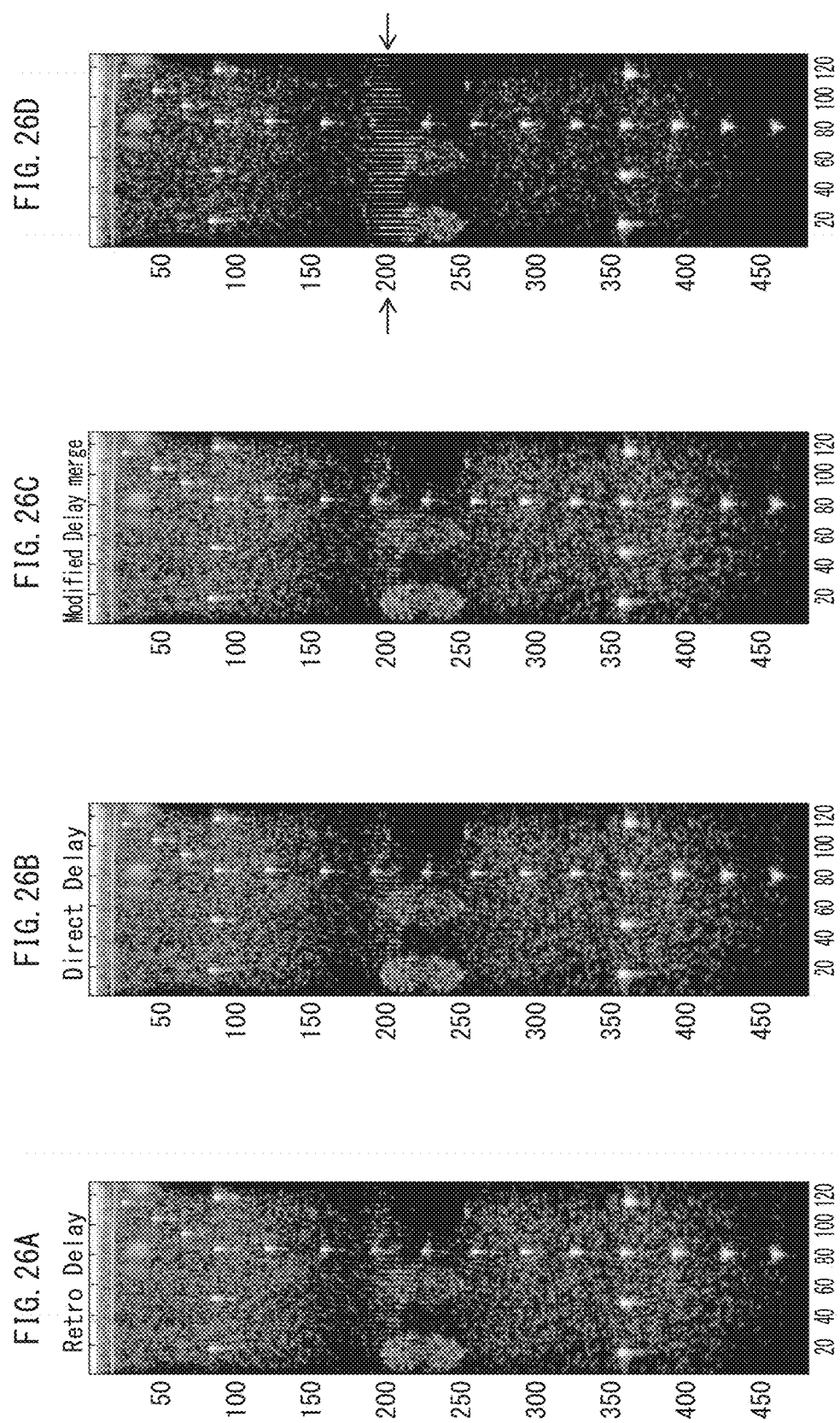

ULTRASOUND SIGNAL PROCESSING DEVICE, ULTRASOUND DIAGNOSTIC DEVICE

CROSS-REFERENCE TO RELATED APPLICATION

This application is a continuation of U.S. application Ser. No. 15/067,858, filed Mar. 11, 2016, which claimed the priority of Japanese Patent Application No. 2015-066483 filed on Mar. 27, 2015, both applications are incorporated by reference herein.

BACKGROUND OF THE INVENTION

(1) Field of the Invention

The present disclosure is related to an ultrasound signal processing device, and an ultrasound diagnostic device equipped with the ultrasound signal processing device. In particular, the present disclosure relates to receive beam forming in an ultrasound signal processing device.

(2) Description of the Related Art

Typically, an ultrasound diagnostic device transmits ultrasound towards the inside of a subject via an ultrasound probe (referred to in the following as a "probe"), and receives reflected ultrasound (an echo) via the probe. The reflected ultrasound is generated within the subject due to tissues in the subject having different acoustic impedances. Further, an ultrasound diagnostic device generates an ultrasound tomographic image based on electric signals acquired through the reception of the reflected ultrasound, and displays the ultrasound tomographic image on a monitor (referred to in the following as a "display unit"). An ultrasound tomographic image shows the structures of tissues inside the subject. Ultrasound diagnostic devices are widely used for the imaging diagnosis of subjects, for having low invasiveness and achieving real-time observation of tissues through tomographic images and the like.

A typical method applied in conventional ultrasound diagnostic devices for forming signals based on received reflected ultrasound (i.e., receive beam forming) is delay-and-sum beam forming. One example of delay-and-sum beam forming can be found disclosed in pages 42-45 of "Ultrasound Diagnostic Device", written by Masayasu Itou and Tsuyoshi Mochizuki and published by Corona Publishing Co., Ltd (Aug. 26, 2002). According to this method, transmission beam forming (i.e., transmission of ultrasound by a plurality of transducer elements towards the inside of the subject) is typically performed such that a transmitted ultrasound beam converges (focuses) at a predetermined focal depth inside the subject. Further, according to this method, measurement points are always set along the central axis of the transmitted ultrasound beam, as illustrated in FIG. 27. Due to this, one ultrasound transmission event generates only one or a few acoustic line signals along the central axis of the transmitted ultrasound beam, and thus, reflected ultrasound is not utilized in an efficient manner. In addition, with this method, it is also problematic that an acoustic line signal acquired from a measurement point distant from the transmission focal point has low resolution and low S/N ratio.

Meanwhile, a receive beam forming method is being proposed that utilizes a so-called synthetic aperture method to yield high quality images not only from near the transmission focal point but also from areas other than near the transmission focal point. One example of receive beam forming utilizing the synthetic aperture method can be found disclosed in pages 395 through 405 of "Virtual Ultrasound Sources in High Resolution Ultrasound Imaging", S. I. Nikolov and J. A. Jensen, in Proc, SPIE—Progress in Biomedical Optics and Imaging, Vol. 3, 2002. According to this method, delaying is performed taking into consideration both a propagation path of ultrasound and the time amount required for reflected ultrasound to arrive at a transducer element by travelling along the propagation path. Thus, the method achieves receive beam forming making use of not only reflected ultrasound from an area of an ultrasound main irradiation area near the transmission focal point but also reflected ultrasound from areas of the ultrasound main irradiation area other than the area near the transmission focal point. Due to this, the method enables generating, from one ultrasound transmission event, acoustic line signals covering the entire ultrasound main irradiation area, including areas far from the transmission focal point. In addition, the synthetic aperture method enables setting a virtual transmission focal point based on multiple receive signals acquired for each measurement point through multiple transmission sessions. Thus, the synthetic aperture method enables acquiring an ultrasound image with higher resolution and higher S/N ratio than the receive beam forming method disclosed in "Ultrasound Diagnostic Device".

SUMMARY OF THE INVENTION

Problems to be Solved by the Invention

Meanwhile, in connection with the synthetic aperture method, research is being conducted to improve ultrasound image resolution per unit time, or that is to increase ultrasound image frame rate. Considering constraints related to the performance of ultrasound diagnostic devices, an increase in frame rate necessitates a reduction in the number of ultrasound transmission events. Meanwhile, with conventional transmission beam forming as described above, the wavefront of ultrasound converges as approaching the transmission focal depth. Accordingly, a reduction in the number of transmission events results in only some areas of the subject along a direction in which ultrasound transducer elements are arrayed being irradiated with ultrasound, with areas not irradiated with ultrasound existing therebetween, particularly at and around the transmission focal depth. Conventionally, measurement points are not set with respect to such areas not irradiated with ultrasound. Due to this, the areas not irradiated with ultrasound form blank areas in ultrasound images, i.e., defective areas in ultrasound images. Such defective areas may lead to a prominent decrease in image quality of ultrasound images.

In view of such problems, the present disclosure provides an ultrasound signal processing device and an ultrasound diagnostic device equipped with such an ultrasound signal processing device that achieve an increase in frame rate, while suppressing the occurrence of defective areas in ultrasound images and the consequent decrease in image quality that would otherwise occur when combining the synthetic aperture method with conventional transmission beam forming.

Means for Solving the Problems

One aspect of the present disclosure is an ultrasound signal processing device: performing a plurality of transmission events each involving selecting a first group of transducer elements from among a plurality of transducer elements of a ultrasound probe that are arranged in at least one line along a transducer element array direction, and causing each transducer element in the first group to transmit ultrasound towards a subject; for each of the transmission events, generating a sub-frame acoustic line signal based on ultrasound reflection received from the subject in response to the transmission event, to yield a plurality of sub-frame acoustic line signals each corresponding to a different one of the transmission events; and generating a frame acoustic line signal based on the sub-frame acoustic line signals for the transmission events. The ultrasound signal processing device includes ultrasound signal processing circuitry that operates as: a transmitter that, in each of the transmission events, selects the first group and causes each transducer element in the first group to transmit ultrasound focusing at a predetermined depth in the subject, the first group in one transmission event differing in position, in the transducer element array direction, from the first group in a previous transmission event by a shift amount corresponding to at least twice a width of a single transducer element in the transducer element array direction; a receiver that selects at least some transducer elements among the plurality of transducer elements of the ultrasound probe, and generates a receive signal sequence for each of the at least some transducer elements based on ultrasound reflection received by the transducer element; a delay-and-sum calculator that, for each of the transmission events: sets a target area including a plurality of measurement points, the target area at least including an area where the ultrasound transmitted from the first group in the transmission event focuses in the subject, wherein at the predetermined depth, a width of the target area in the transducer element array direction is equal to or greater than the shift amount; and generates a sub-frame acoustic line signal composed of a plurality of acoustic line signals, one for each measurement point included in the target area, by performing, for each measurement point that is included in the target area, delay-and-sum processing with respect to one or more receive signal sequences corresponding to the measurement point, the one or more receive signal sequences corresponding to the measurement point respectively generated for one or more transducer elements composing a second group of transducer elements, among the plurality of transducer elements of the ultrasound probe, based on ultrasound reflection received from the measurement point; and a synthesizer that generates a frame acoustic line signal based on a plurality of sub-frame acoustic line signals corresponding one-to-one with the transmission events.

BRIEF DESCRIPTION OF THE DRAWINGS

These and the other objects, advantages and features of the invention will become apparent from the following description thereof taken in conjunction with the accompanying drawings which illustrate a specific embodiment of the invention.

Figure 27:
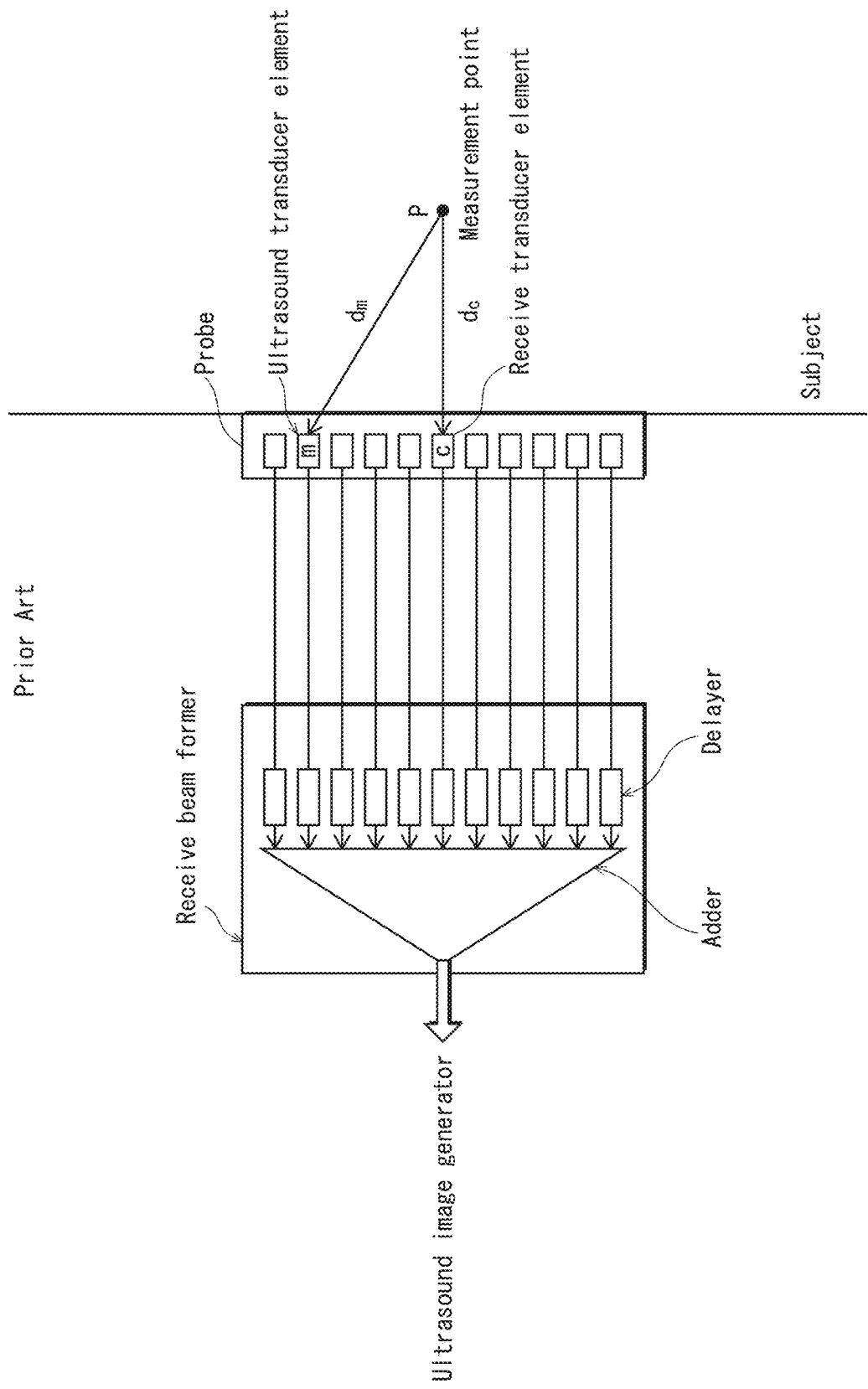
Figure 28A:
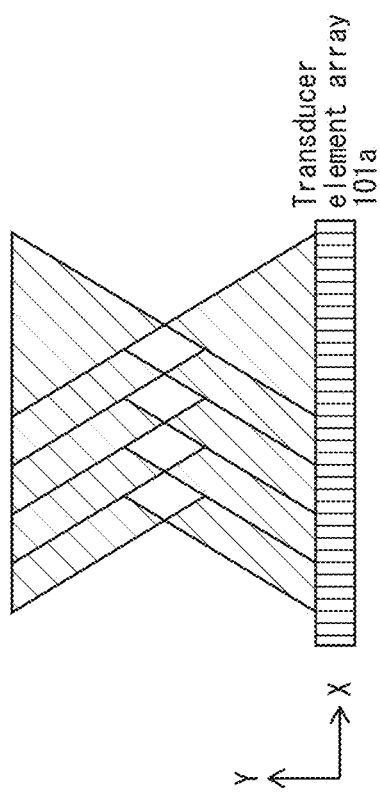
Figure 28B:
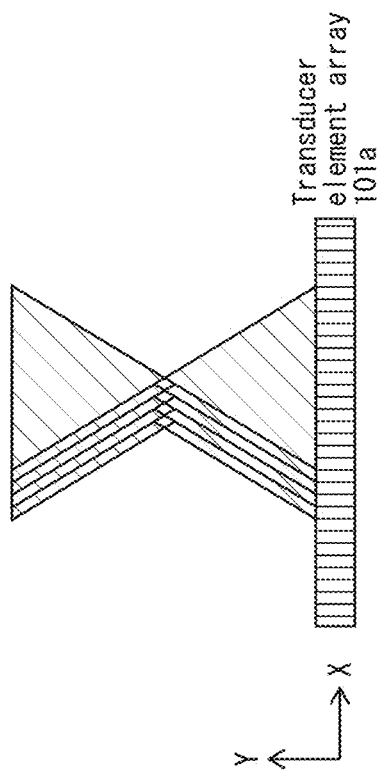

Each of FIGS. 26A through 26D shows an example of an ultrasound image;

FIG. 27 is a schematic illustrating delay-and-sum processing in a conventional ultrasound diagnostic device; and FIGS. 28A and 28B are schematics for explaining a problem arising when combining conventional transmission beam forming causing wavefront to converge, with the synthetic aperture method.

DESCRIPTION OF EMBODIMENTS

How Inventor Arrived at Aspects of Present Disclosure

The present inventor conducted much research for achieving increasing frame rate with an ultrasound diagnostic device employing the synthetic aperture method.

A conventional ultrasound diagnostic device performs transmission beam forming (i.e., transmission of ultrasound by a plurality of transducer elements towards the inside of the subject) by causing wavefront of transmitted ultrasound to converge (focus) inside the subject at the transmission focal depth. Thus, each transmission event results in a specific area inside the subject receiving most of the reflected ultrasound (echo signals) from the transmission transducer elements, which are transducer elements used for ultrasound transmission. Specifically, this area, referred to in the following as an ultrasound main irradiation area, is an area including measurement points where ultrasound transmitted from all transmission transducer elements are in-phase. For example, when ultrasound transmission is performed with one measurement point set as the transmission focal point, the ultrasound main irradiation area has an hourglass shape, the bottom edge (i.e., base) of the ultrasound main irradiation area corresponds to the array of the transmission transducer elements, and two straight lines each extending from a different end of the base towards the transmission focal point partition the ultrasound main irradiation area from the outside thereof. Further, the wavefront of ultrasound transmitted from the transmission transducer elements forms an arc, being a segment of a circle whose center corresponds to the transmission focal point. Here, it should be noted that the ultrasound transmitted from the transmission transducer elements does not always converge (i.e., focus) at a single point as described above. That is, transmitted ultrasound may gather at an area (referred to in the following as a transmission focal area) having a width corresponding to half the width of a single transducer element to several times the width of a single transducer element. When ultrasound focuses at such an area, the width of the ultrasound main irradiation area in a direction in which the transducer elements are arrayed (referred to in the following as a transducer element array direction) decreases as approaching the transmission focal depth, equals the width of the transmission focal area at the transmission focal depth, and increases once again as departing the transmission focal depth towards deeper areas. Nevertheless, in either case, the width of the ultrasound main irradiation area in the transducer element array direction reaches a minimum at the transmission focal depth, and increases with increasing distance from the transmission focal depth.

Further, with the synthetic aperture method, for each transmission event, measurement points covering the entire ultrasound main irradiation area of the transmission event can be set. As such, it is preferable that the entirety of the ultrasound main irradiation area be set as a target area, being an area composed of measurement points from which acoustic line signals are to be generated. Meanwhile, a target area for one transmission event cannot cover the entirety of an area corresponding to one frame image. As such, a plurality of transmission events, for each of which a different target area is set, need to be conducted to generate one frame image. Taking this into consideration and to increase the efficiency of use of ultrasound, it is preferable that a target area for a transmission event cover as great an area of an ultrasound main irradiation area for the transmission event as possible. Further, in general, to achieve high spatial resolution and high signal S/N ratio, it is preferable that target areas for two consecutive transmission events overlap one another as much as possible.

In view of the above, typically, a frame acoustic line signal (a group of acoustic line signals corresponding to one frame image) is generated by combining a plurality of sub-frame acoustic line signals (each being a group of acoustic line signals generated in response to one transmission event), as illustrated in FIG. 28A. Here, each sub-frame acoustic line signal is generated in response to one transmission event that is performed by setting the entire hourglass-shaped ultrasound main irradiation area of the transmission event as the target area for the transmission event. Further, a plurality of such sub-frame acoustic line signals are generated while shifting both the ultrasound main irradiation area and the target area by a shift amount corresponding to a width of a single transducer element between consecutive transmission events. When employing this method, the time amount required to generate one frame image equals a product of the time amount required to perform a single transmission event and the number of transmission events performed per frame.

As already described above, the synthetic aperture method produces acoustic line signals having high resolution and high signal S/N ratio. However, an increase in frame rate would be desirable in situations such as where quick acquisition of ultrasound images is desired for reducing stress of the examination subject and the examiner, and where an increase in time-domain resolution of ultrasound images is desired for examining movements within the subject, such as blood flow. Achieving an increase in frame rate requires reducing the time amount required to generate each frame image. However, this reduction in the time amount required to generate a single ultrasound image cannot be achieved by reducing the time amount required for each transmission event, since the time amount required for a single transmission event is almost uniquely dependent upon ultrasound propagation velocity, and thus, cannot be reduced easily. In view of this, consideration is being made of achieving an increase in frame rate by reducing the number of transmission events performed per frame.

A reduction in the number of transmission events performed per frame can be achieved by increasing the shift amount applied in shifting the ultrasound main irradiation area and the target area between consecutive transmission events. For example, frame rate can be doubled by setting the shift amount to twice the width of a single transducer element, which equals cutting down the number of sub-frame acoustic line signals generated per frame to ½. Similarly, frame rate can be quadrupled by setting the shift amount to four times the width of a single transducer element.

However, when setting the entirety of the hourglass-shaped ultrasound main irradiation area as the target area and also setting the shift amount to at least twice the width of a single transducer element, defective areas as illustrated in FIG. 28B are produced. (Note that in the present disclosure, an area of an ultrasound image that is not included in any target area of any transmission event performed for generating the ultrasound image is referred to as a defective area.) FIG. 28B illustrates a case where the shift amount is set to four times the width of a single transducer element. In FIG. 28B, the defective areas are produced at and around the transmission focal depth, where the width of the ultrasound main irradiation areas in the transducer element array direction is smaller than the shift amount. Such defective areas are also produced when transmitted ultrasound converges at focus areas, whenever the width of the focus areas in the transducer element array direction is smaller than the shift amount. Further, when target areas are set in the inside of ultrasound main irradiation areas, the same problem occurs whenever the width of the target areas in the transducer element array direction at the transmission focal depth is smaller than the shift amount. FIG. 26D illustrates one example of an ultrasound image in which such defective areas are observed. The arrow in FIG. 26D indicates focal depth. Here, it should be noted that due to transmitted ultrasound converging at the transmission focal depth, strong reflected ultrasound is acquired from areas at and around the transmission focal depth near which the defective areas are produced. Due to this, the defective areas tend to stand out in ultrasound images in the form of vertical stripes. Such stripes lead to a prominent decrease in image quality at and around the transmission focal depth.

In view of such problems, the present inventor conducted research of a technology achieving an increase in frame rate while suppressing the decrease in image quality described above, which would otherwise occur when combining the synthetic aperture method with conventional transmission beam forming causing wavefront of ultrasound to converge. It is through such research that the present inventor arrived at the ultrasound signal processing methods and the ultrasound diagnostic devices employing such ultrasound signal processing methods described in the following embodiments.

The following embodiments describe the ultrasound signal processing methods and the ultrasound diagnostic devices employing such ultrasound signal processing methods in detail, with reference to the accompanying drawings.

Embodiment 1

<Overall Structure>

The following describes an ultrasound diagnostic device 100 pertaining to embodiment 1, with reference to the accompanying drawings.

Figure 1:
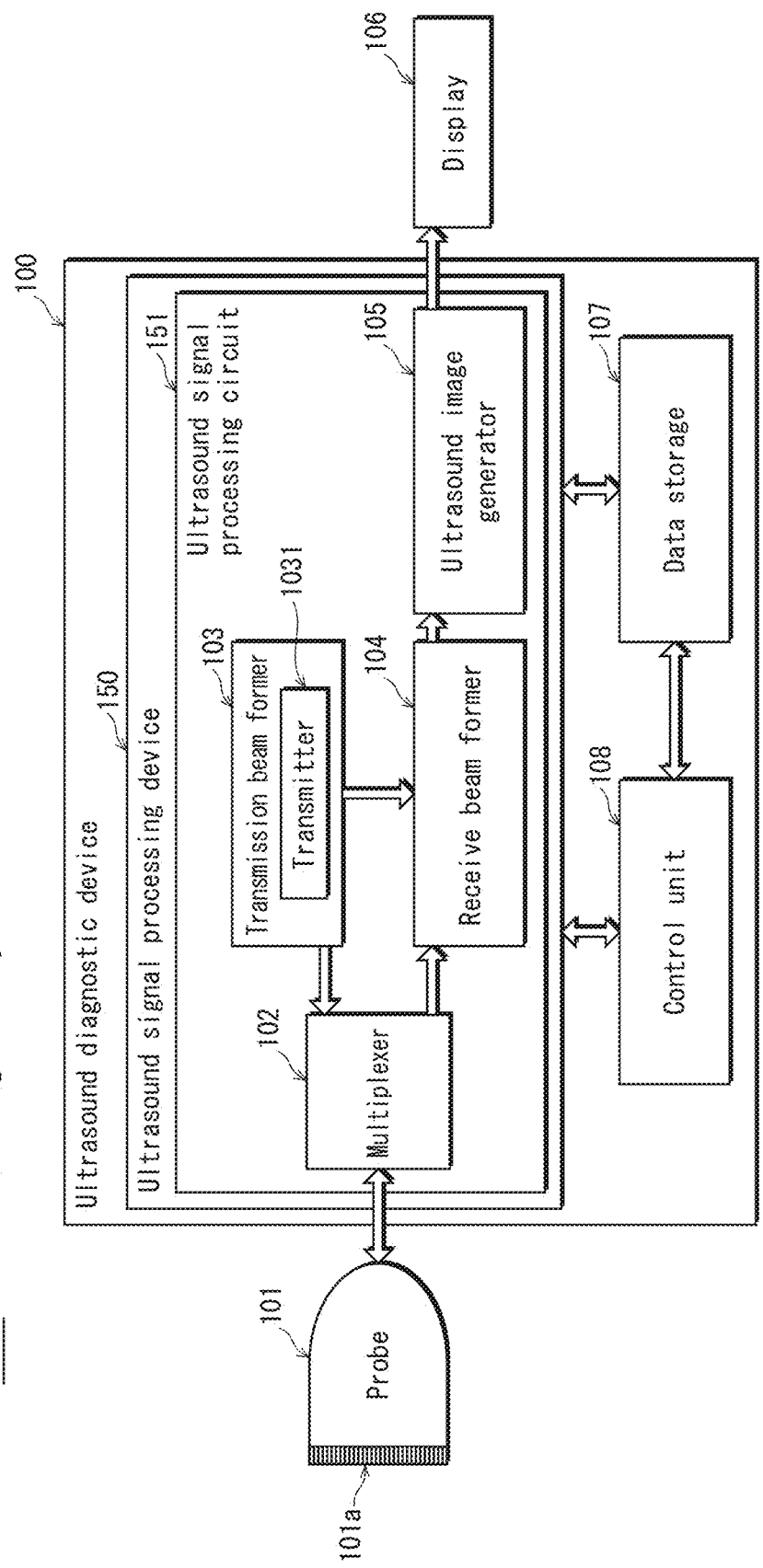
FIG. 1 is a functional block diagram illustrating the structure of an ultrasound diagnostic device 100 pertaining to embodiment 1.

FIG. 1 illustrates functional blocks of an ultrasound diagnostic system 1000 pertaining to embodiment 1. As illustrated in FIG. 1, the ultrasound diagnostic system 1000 includes: a probe 101; the ultrasound diagnostic device 100; and a display unit 106. The probe 101 includes a plurality of transducer elements 101a. Each of the transducer elements 101a is capable of transmitting ultrasound towards the subject and receiving reflected ultrasound (echo signals). The ultrasound diagnostic device 100 causes the probe 101 to perform transmission/reception of ultrasound, and generates an ultrasound image based on signals output from the probe 101. The display unit 106 displays the ultrasound image on any display device provided thereto. The probe 101 and the display unit 106 are separately connectable to the ultrasound diagnostic device 100. FIG. 1 illustrates the ultrasound diagnostic device 100 with the probe 101 and the display unit 106 connected thereto. Alternatively, the ultrasound diagnostic device 100 may include therein the probe 101 and the display unit 106.

<Structure of Ultrasound Diagnostic Device 100>

The ultrasound diagnostic device 100 includes a multiplexer 102; a transmission beam former 103; and a receive beam former 104. The multiplexer 102 selects one or more of the transducer elements 101a for ultrasound transmission and one or more of the transducer elements 101a for ultrasound reception. The multiplexer 102 may select different ones of the transducer elements 101a for ultrasound transmission and ultrasound reception. Further, the multiplexer 102 provides the transducer elements 101a for ultrasound transmission with input, and receives output from the transducer elements 101a for ultrasound reception. The transmission beam former 103 controls timings of application of a high voltage for ultrasound transmission to each of the transducer elements 101a for ultrasound transmission. The receive beam former 104 performs some amplification and A/D conversion on electric signals yielded by the transducer elements 101a for ultrasound reception, based on reflected ultrasound received by the probe 101, and performs receive beam forming to generate acoustic line signals. In addition, the ultrasound diagnostic device 100 includes an ultrasound image generator 105; a data storage 107; and a control unit 108. The ultrasound image generator 105 generates an ultrasound image (a B-mode image) based on signals output from the receive beam former 104. The data storage 107 stores the acoustic line signal output from the receive beam former 104 and the ultrasound image output from the ultrasound image generator 105. The control unit 108 controls each of the other components of the ultrasound diagnostic device 100.

Among the components of the ultrasound diagnostic device 100, the multiplexer 102, the transmission beam former 103, the receive beam former 104, and the ultrasound image generator 105 constitute an ultrasound signal processing circuit 151, and the ultrasound signal processing circuit 151 constitutes an ultrasound signal processing device 150.

Each component of the ultrasound diagnostic device 100, for example, each of the multiplexer 102, the transmission beam former 103, the receive beam former 104, the ultrasound image generator 105, and the control unit 108 may be implemented by using a hardware circuit such as a field-programmable gate array (FPGA), an application-specific integrated circuit (ASIC), or the like. Alternatively, each of the components may be implemented by using a combination of software and a programmable device such as a central processing unit (CPU), a General-purpose computing on graphics processing unit (GPGPU), or any processor. Each of such components may be implemented as one circuit component, or as an aggregate of a plurality of circuit components. Further, a plurality of such components may be implemented by using one circuit component, or as an aggregate of a plurality of circuit components.

The data storage 107 is a computer-readable recording medium. For example, the data storage 107 may be implemented by using a flexible disk, a hard disk, an MO, a DVD, a DVD-RAM, a BD, or a semiconductor memory. Alternatively, the data storage 107 may be an external storage device connected to the ultrasound diagnostic device 100.

Note that the ultrasound diagnostic device 100 pertaining to the present embodiment need not have the structure illustrated in FIG. 1. For example, the ultrasound diagnostic device 100 may not include the multiplexer 102, and the transmission beam former 103 and the receive beam former 104 may be directly connected with each transducer element 101*a* of the probe 101. Further, the probe 101 may have built-in therein a part or the entirety of each of the transmission beam former 103, the receive beam former 104, and the like. Such modifications apply not only to the ultrasound diagnostic device 100 pertaining to the present embodiment, but also similarly apply to the ultrasound diagnostic devices described later in the other embodiments and modifications in the present disclosure.

<Structure of Main Part of Ultrasound Diagnostic Device 100>

The ultrasound diagnostic device 100 pertaining to embodiment 1 is characterized for including the transmission beam former 103 and the receive beam former 104. The transmission beam former 103 causes the transducer elements 101*a* of the probe 101 to transmit ultrasound. The receive beam former 104 performs computation with respect to electric signals acquired through the reception of reflected ultrasound by the probe 101, and generates acoustic line signals used in forming an ultrasound image. Accordingly, the present disclosure focuses on the structure and the functions of each of the transmission beam former 103 and the receive beam former 104. Note that components other than the transmission beam former 103 and the receive beam former 104 may have structures and functions similar to those in conventional ultrasound diagnostic devices. In other words, the ultrasound diagnostic device 100 may be implemented by replacing beam formers in a conventional ultrasound diagnostic device with the beam formers pertaining to the present embodiment.

The following describes the structure of each of the transmission beam former 103 and the receive beam former 104.

1. Transmission Beam Former 103

The transmission beam former 103 is connected to the probe 101, via the multiplexer 102. However, note that the multiplexer 102 is not a mandatory element in the present disclosure. The transmission beam former 103 controls timings of application of high voltage with respect to each of a plurality of transducer elements 101*a* composing a transmission aperture Tx. The transmission aperture Tx is an array of transducer elements composed of all or some of the transducer elements 101*a* of the probe 101. Note that in the following, the term "transmission transducer element" is used to refer to transducer elements composing the transmission aperture Tx. The transmission beam former 103 includes a transmitter 1031.

The transmitter 1031 performs transmission processing. The transmission processing involves supplying a transmission signal having a pulsar waveform to each of the transmission transducer elements. A transmission transducer element receiving a transmission signal transmits an ultrasound beam. The transmitter 1031 supplies transmission signals to the transmission transducer elements based on transmission control signals output from the control unit 108. In specific, the transmitter 1031 includes, for example, a clock generation circuit, a pulse generation circuit, and a delay circuit. The clock generation circuit generates a clock signal specifying the transmission timing of ultrasound beams. The pulse generation circuit generates pulse signals for driving the transmission transducer elements. The delay circuit performs focus processing so that ultrasound beams are appropriately focused. In specific, the delay circuit sets a delay time for each transmission transducer element, and delays the transmission of the ultrasound beam from the transmission transducer element by the corresponding delay time.

The transmitter 1031 repetitively performs ultrasound transmission while shifting the transmission aperture Tx in the transducer element array direction by a predetermined shift amount Mp each time, so that all of the transducer elements 101*a* of the probe 101 transmit ultrasound. The shift amount Mp is at least equal to twice the width of a single transducer element in the transducer element array direction. Note that the present embodiment provides description based on an example where the shift amount Mp equals four times the width of a single transducer element in the transducer element array direction. Thus, in the present embodiment, transmission apertures Tx corresponding to two consecutive transmission events differ in position in the transducer element array direction by an amount corresponding to four times the width of a single transducer element. Further, the transmitter 1031 outputs information indicating the positions of transmission transducer elements composing the transmission aperture Tx to the data storage 107, via the control unit 108. For example, supposing that the probe 101 has one hundred and ninety two (192) transducer elements 101*a* in total, the number of transmission transducer elements composing the transmission aperture Tx may be twenty (20) to one hundred (100). Further, in the present disclosure, the term transmission event is used to refer to ultrasound transmission by the transmitter 1031, performed by using one transmission aperture (i.e., one set of transmission transducer elements of the predetermined number).

Figure 2:
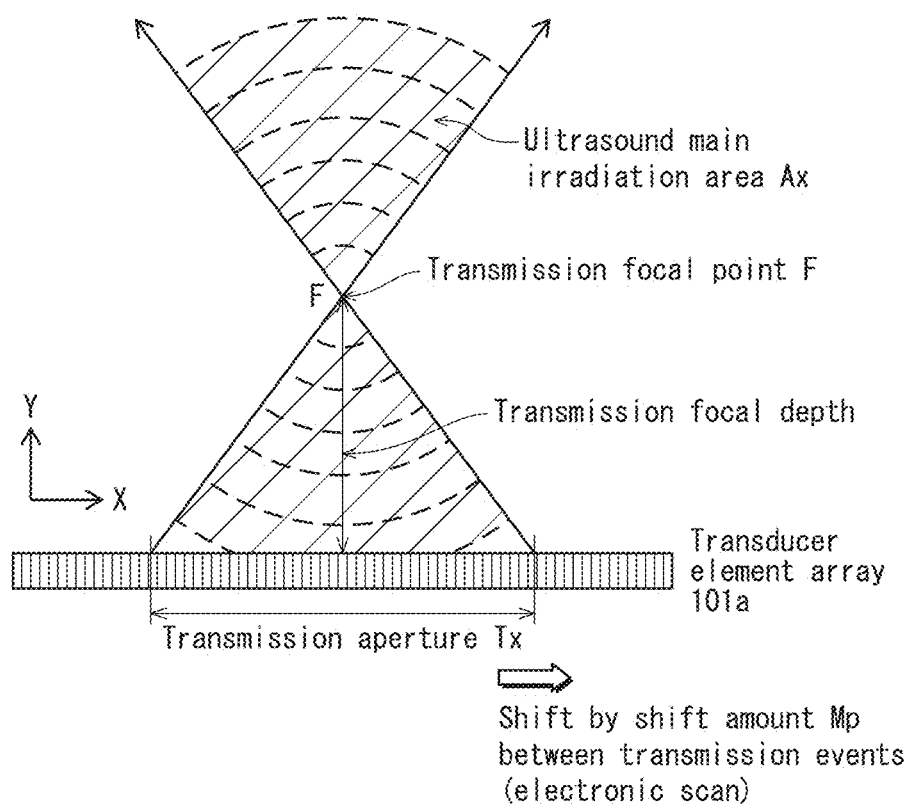
FIG. 2 is a schematic illustrating a propagation path of ultrasound transmitted from a transmission beam former 103 pertaining to embodiment 1.

FIG. 2 is a schematic illustrating a propagation path of ultrasound transmitted by the transmission beam former

103. FIG. 2 illustrates a transmission aperture Tx for one transmission event (i.e., a transmission transducer element array composed of transmission transducer elements 101a that contribute to ultrasound transmission in the transmission event). Further, the transmission-array direction length of the transmission aperture Tx is considered the length of the transmission aperture Tx.

The transmission beam former 103 controls ultrasound transmission by the transmission transducer elements such that a transmission transducer element closer to the center position of the transmission aperture Tx transmits ultrasound later in the transmission event. Due to this, the wavefront of ultrasound transmitted from the transmission transducer elements composing the transmission aperture Tx converges at one point at a certain focal depth in the subject (i.e., the transmission focal point F). Note that the depth of the transmission focal point F (i.e., transmission focal depth) can be set as desired or required. After converging at the transmission focal point F, the wavefront of the transmitted ultrasound spreads out as before converging at the transmission focal point F. Thus, the transmitted ultrasound propagates through an hourglass-shaped area whose base is defined by the transmission aperture Tx and which is partitioned from other areas inside the subject by two straight lines intersecting at the transmission focal point F. More specifically, ultrasound transmitted from the transmission aperture Tx propagates in the following manner. As the transmitted ultrasound advances in a depth direction of the subject from the transmission aperture Tx, the width thereof (length along horizontal axis (X axis) in FIG. 2) gradually decreases until reaching the minimum width at the transmission focal point F. Then, as the transmitted ultrasound advances further in the depth direction from the transmission focal point F (i.e., as the ultrasound advances in the upward direction in FIG. 2), the width thereof increases (i.e., the ultrasound spreads out). In the following, the hourglass-shaped area described above is referred to as a ultrasound main irradiation area Ax. Note that as already described above, the width of the ultrasound main irradiation area need not reach a minimum at one point (i.e., the transmission focal point F), and instead, may reach a minimum at a certain area (i.e., a transmission focal area).

Further, as also described above, the ultrasound main irradiation area Ax is an area in which ultrasound transmitted from the transmission transducer elements are in-phase. In the meantime, ultrasound transmitted from the transmission transducer elements also propagate to the outside of the ultrasound main irradiation area Ax. However, phase difference of the ultrasound transmitted from the different transmission transducer elements occurs outside the ultrasound main irradiation area Ax, and thus, the quality of ultrasound transmission waves arriving at points outside the ultrasound main irradiation area Ax is lower than that of ultrasound transmission waves arriving at points inside the ultrasound main irradiation area Ax. More specifically, the greater the distance from the ultrasound main irradiation area Ax, the lower the quality of ultrasound transmission waves. However, this, in other words, means that ultrasound transmission waves arriving at points close to the ultrasound main irradiation area Ax, or more specifically, points within a distance of a few transducer elements from the ultrasound main irradiation area Ax, has sufficient level to generate beneficial acoustic line signals.

2. Receive Beam Former 104

Figure 3:
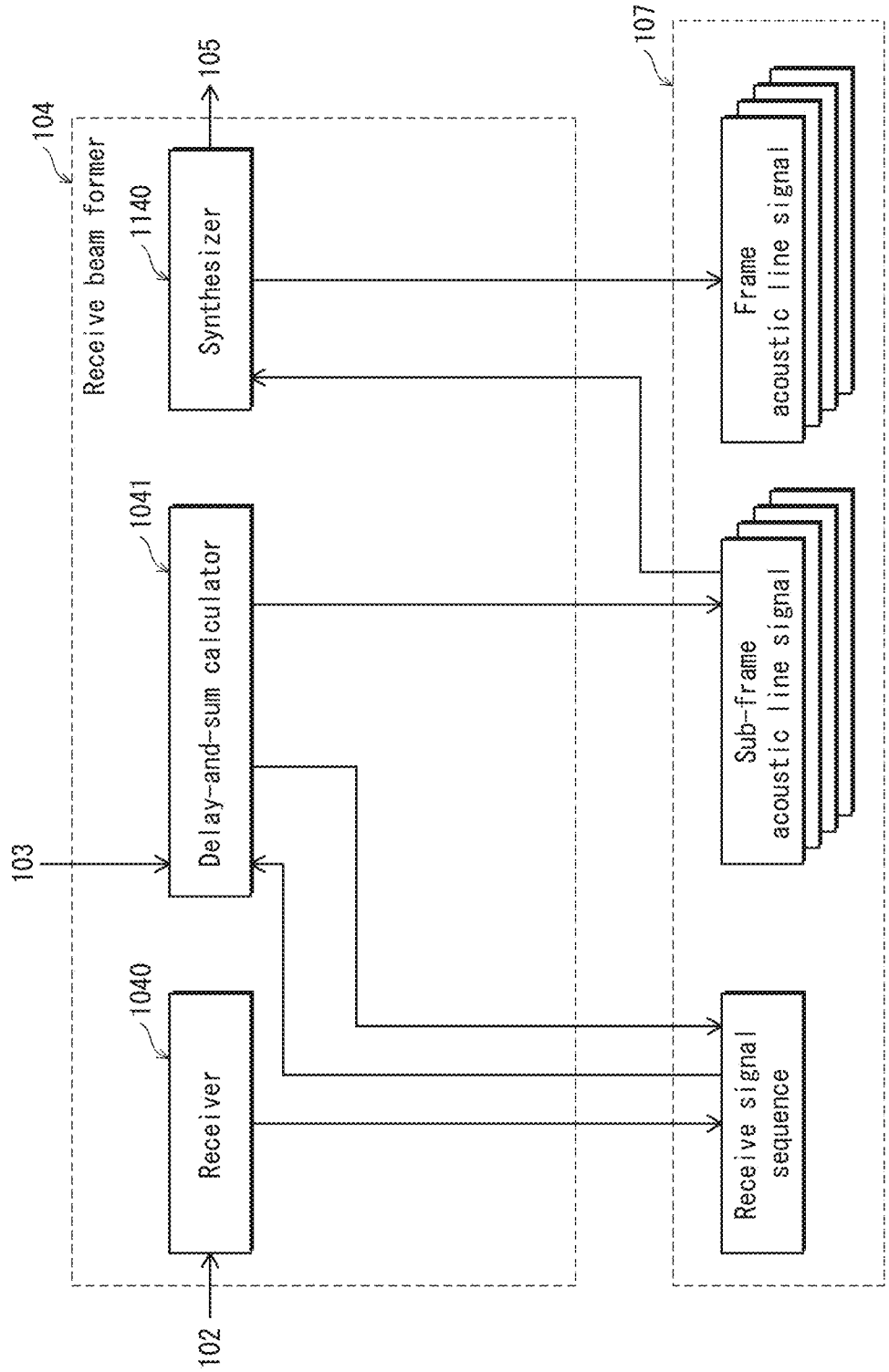
FIG. 3 is a functional block diagram illustrating the structure of a receive beam former 104 pertaining to embodiment 1.

The receive beam former 104 generates acoustic line signals from electric signals acquired by a plurality of transducer elements 101a. The transducer elements 101a acquire the electric signals based on reflected ultrasound received by the probe 101. Here, an acoustic line signal for one measurement point is generated by performing delay-and-sum processing with respect to receive signals from the measurement point. Description of the delay-and-sum processing is provided later in the present disclosure. FIG. 3 is a functional block diagram illustrating the structure of the receive beam former 104. As illustrated in FIG. 3, the receive beam former 104 includes: a receiver 1040; a delay-and-sum calculator 1041; and a synthesizer 1140.

The following describes the structure of each functional block of the receive beam former 104.

(1) Receiver 1040

The receiver 1040 is connected to the probe 101, via the multiplexer 102. However, note that the multiplexer 102 is not a mandatory element in the present disclosure. For each transmission event, the receiver 1040 generates receive signals (RF signals). The receiver 1040 generates the receive signals by first amplifying electric signals acquired through the probe 101 receiving reflected ultrasound, and then performing A/D conversion on the amplified signals. The receiver 1040 performs the generation of receive signals for each transmission event, and outputs the receive signals to be stored in the data storage 107.

Here, the receiver 1040 generates one receive signal sequence (RF signal) for each of some or all of the transducer elements 101a of the probe 101. In specific, a receive signal sequence for a given transducer element is a digital signal yielded by performing A/D conversion on an electrical signal yielded through conversion of reflected ultrasound received by the transducer element, and is a sequence of signals along the ultrasound transmission direction (corresponding to the depth direction) that are received by the transducer element.

As discussed above, in each transmission event, the transmitter 1031 causes the plurality of transmission transducer elements composing the transmission aperture Tx, among the transducer elements 101a of the probe 101, each to transmit an ultrasound beam. Meanwhile, for each ultrasound transmission event, the receiver 1040 generates a receive signal sequence for each of some or all of the plurality of transducer elements 101a of the probe 101. The generation of the receive signal sequence for a given one of such transducer elements 101a is based on reflected ultrasound yielded by the given transducer element 101a. Here, it is preferable that the number of transducer elements for which receive signal sequences are generated be greater than the number of transmission transducer elements composing the transmission aperture Tx. Further, receive signal sequences may be generated for all of the transducer elements 101a of the probe 101.

Further, as already discussed above, the transmitter 1031 repetitively performs transmission events while shifting the transmission aperture Tx in the transducer element array direction by the shift amount Mp between transmission events, so that all of the transducer elements 101a of the probe 101 transmit ultrasound. Meanwhile, for each ultrasound transmission event, the receiver 1040 generates a receive signal sequence for each of some or all of the plurality of transducer elements 101a of the probe 101, and stores the receive signal sequences to the data storage 107.

(2) Delay-and-Sum Calculator 1041

Figure 4:
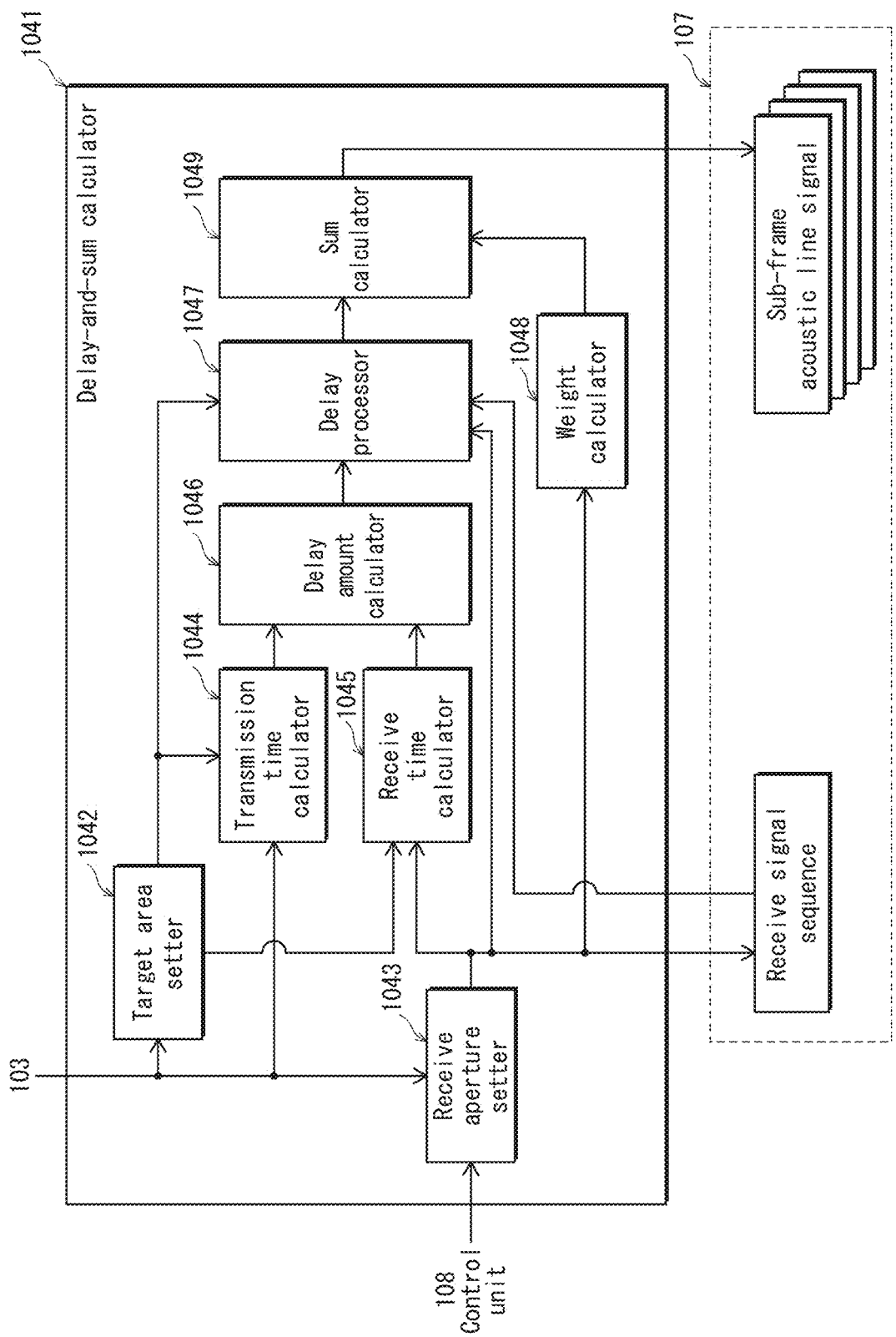
FIG. 4 is a functional block diagram illustrating the structure of a delay-and-sum calculator 1041 pertaining to embodiment 1.

The delay-and-sum calculator 1041 sets a target area Bx for each transmission event. A target area Bx is an area in the subject from which one sub-frame acoustic line signal is to be generated. Each target area Bx is composed of some of a plurality of measurement points Pij. Further, the delay-andsum calculator 1041 performs, for each measurement point Pij in the target area Bx, delay-and-sum processing with respect to receive signal sequences corresponding to the measurement point Pij, each of which is received by one receive transducer element Rk. The delay-and-sum calculator 1041 performs this processing for each transmission event having been performed. The delay-and-sum calculator 1041, for each transmission event, generates a sub-frame acoustic line signal for the transmission event by calculating an acoustic line signal for each measurement point that is included in the target area Bx for the transmission event. FIG. 4 is a functional block diagram illustrating the structure of the delay-and-sum calculator 1041. As illustrated in FIG. 4, the delay-and-sum calculator 1041 includes: a target area setter 1042; a receive aperture setter 1043; a transmission time calculator 1044; a receive time calculator 1045; a delay amount calculator 1046; a delay processor 1047; a weight calculator 1048; and a sum calculator 1049.

The following describes the structure of each functional block of the delay-and-sum calculator 1041.

i) Target Area Setter 1042

The delay-and-sum calculator 1042 sets the target area Bx, which is an area in the subject from which one sub-frame acoustic line signal is to be generated. More specifically, in the present disclosure, the term "target area" is used to indicate a signal area for generating a sub-frame acoustic line signal for one transmission event. Further, one acoustic line signal is generated for each measurement point Pij that is included in the target area Bx. In other words, the target area Bx is set for each transmission event in order to specify ones of the measurement points for which acoustic line signals are to be generated in response to the transmission event.

Further, in the present disclosure, a sub-frame acoustic line signal is a group of acoustic lines signals that are generated from one transmission event. As already described above, in response to one transmission event, a plurality of acoustic line signals are generated, each for a different one of the measurement points Pij included in the target area Bx. Further, a sub-frame is a unit corresponding to a group of signals which are acquired from one transmission event and each of which corresponds to a different one of the measurement points Pij that are included in the target area Bx for the transmission event. Thus, a combination of multiple sub-frames acquired at different time points equals one frame.

For each transmission event, the target area setter 1042 sets a target area Bx based on the information indicating the position of the transmission aperture Tx for the transmission event, which is acquired from the transmission beam former 103.

Figure 5:
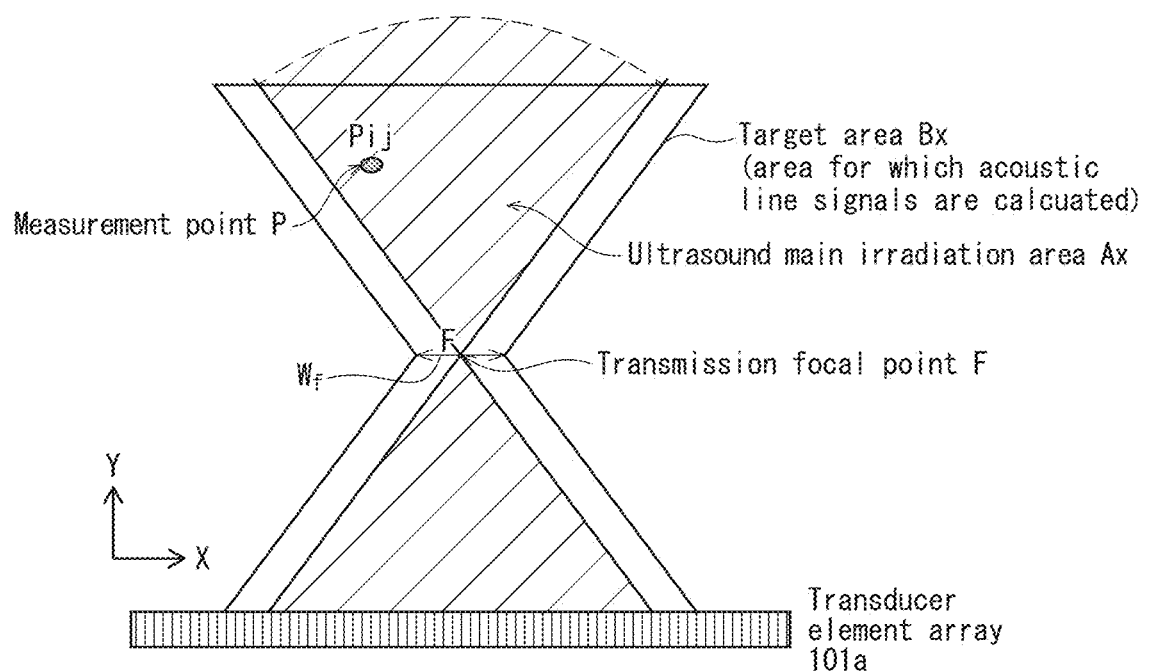
FIG. 5 is a schematic illustrating a target area Bx pertaining to embodiment 1.

FIG. 5 is a schematic illustrating one target area Bx. As illustrated in FIG. 5, a target area Bx for a transmission event covers a greater area than the ultrasound main irradiation area Ax for the transmission event. That is, the target area Bx includes the outside of the ultrasound main irradiation area Ax. Further, the target area Bx is set so that a minimum width of the target area Bx in the transducer element array direction is equal to or greater than the shift amount Mp. For example, in the present embodiment, the target area Bx is yielded by expanding the hourglass-shaped ultrasound main irradiation area Ax by a predetermined amount, in each of the two directions along the transducer element array direction. Due to this, the width of the target area Bx in the transducer element array direction reaches a minimum at the transmission focal depth. Thus, the target area Bx is set so that the minimum width of the target area Bx in the transducer element array direction (referred to in the following as a width Wf) is equal to or greater than the shift amount Mp. For example, when the shift amount Mp equals four times the width of a single transducer element, it is sufficient that the width Wf be set to at least four times the width of a single transducer element. Further, the width Wf is twice the predetermined amount described above, which is the amount by which the ultrasound main irradiation area Ax is expanded in each of the two directions along the transducer element array direction to yield the target area Bx. Thus, the predetermined amount is at least half the shift amount Mp, and for example, may equal at least three times the width of a single transducer element. By setting the target area Bx in such a manner, the target area Bx is capable of including both measurement points covering substantially the entire ultrasound main irradiation area Ax and measurement points located in the proximity of the ultrasound main irradiation area Ax. This achieves efficient use of transmitted ultrasound.

However, the target area Bx may have a shape other than the above-described shape yielded by expanding an hourglass shape in the width direction. For example, the target area Bx may have a rectangular shape, with the base set along the subject surface that is in contact with the transmission transducer element array. Providing the target area Bx with such a shape results in the target area Bx including measurement points covering substantially the entire ultrasound main irradiation area Ax, which also achieves efficient use of transmitted ultrasound. However, as already described above, at the outside of the ultrasound main irradiation area Ax, the greater the distance from the ultrasound main irradiation area Ax, the lower the quality of ultrasound transmission waves. Thus, it is preferable that the target area Bx include only the ultrasound main irradiation area Ax and the proximity of the ultrasound main irradiation area Ax.

The target area setter 1042 outputs the target area Bx to the transmission time calculator 1044, the receive time calculator 1045, and the delay processor 1047.

ii) Receive Aperture Setter 1043

The receive aperture setter 1043 is a circuit that sets, for each transmission event, receive apertures Rx based on a control signal from the control unit 108 and information from the target area setter 1042 indicating the target area Bx for the transmission event. In specific, the receive aperture setter 1043 selects, for each measurement point P in the target area Bx, some of the transducer elements 101a of the probe 101 as receive transducer elements forming a transducer element array (referred to in the following as a receive transducer element array) whose center position corresponds to a transducer element closest to the measurement point P.

Figure 6:
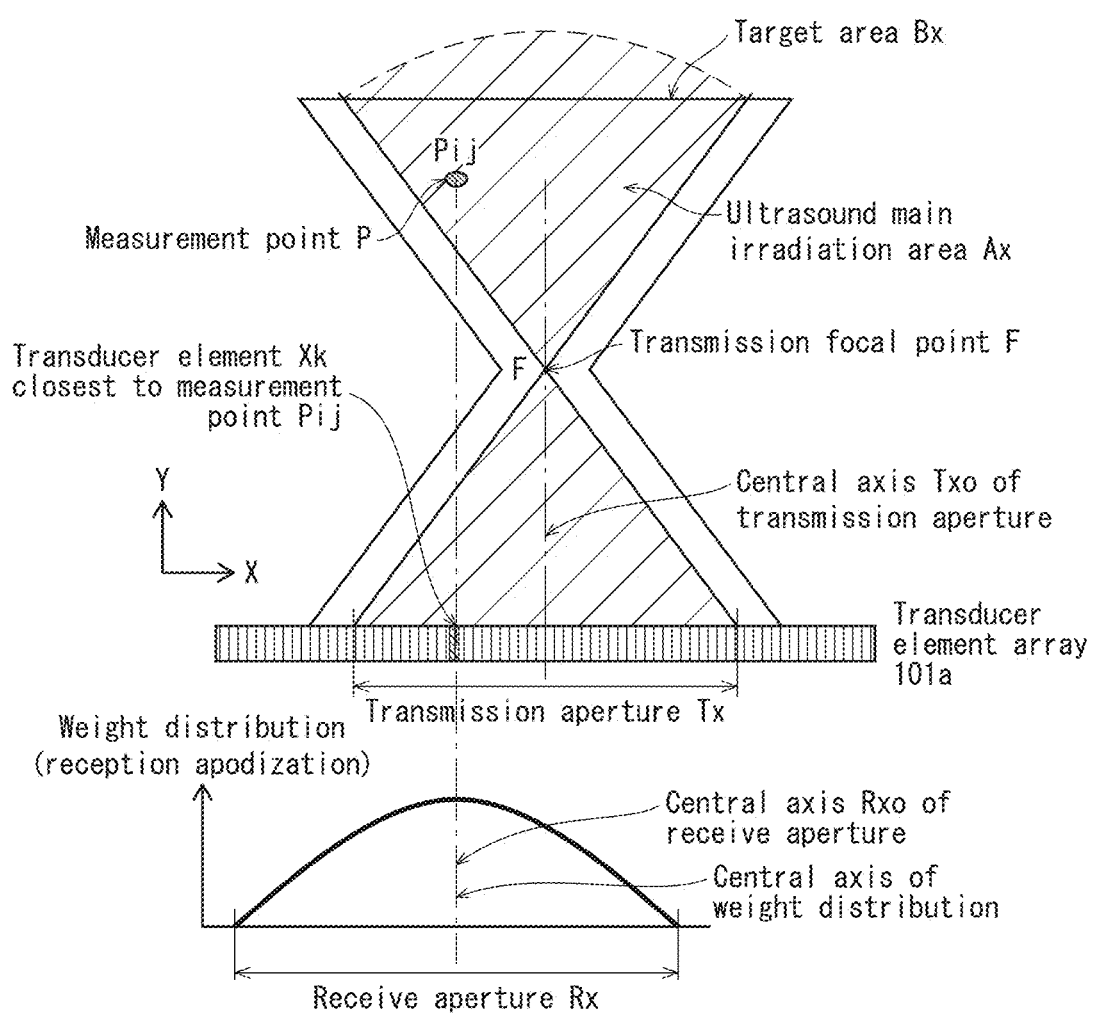
FIG. 6 is a schematic illustrating the relationship between a transmission aperture Tx and a receive aperture Rx set by a receive aperture setter 1043 pertaining to embodiment 1.

The receive aperture setter 1043 sets, for each measurement point P that is included in a target area Bx for a transmission event, a receive aperture Rx (i.e., the receive transducer element array) so that the center position of the receive aperture Rx in the transducer element array direction corresponds to a transducer element that is spatially closest to the measurement point P. FIG. 6 is a schematic illustrating the relationship between a transmission aperture Tx and a receive aperture Rx that the receive aperture setter 1043 sets. As illustrated in FIG. 6, for a given measurement point Pij, the receive aperture Rx is set so that the center position of the receive aperture Rx in the transducer element array direction corresponds to a transducer element Xk that is spatially closest to the measurement point Pij. Due to this, the position of the receive aperture Rx depends upon the position of the measurement point P, and does not change depending upon the position of the transmission aperture Tx, which shifts each time a transmission event is performed. That is, delay-and-sum processing for generating an acoustic line signal for a given measurement point Pij is always performed based on receive signal sequences acquired by receive transducer elements Rk composing the same receive aperture Rx. This means that with respect to the measurement point Pij, the same receive aperture Rx is used in delay-and-sum processing irrespective of transmission events.

In order to utilize reflected ultrasound from the entirety of the ultrasound main irradiation area, the number of the receive transducer elements composing each receive aperture Rx is, beneficially, greater than or equal to the number of transmission transducer elements composing each transmission aperture Tx. For example, the number of receive transducer elements may be 32, 64, 96, 128, 192, and so on.

The setting of the receive apertures Rx is performed for each transmission event. Due to this, the setting of the receive aperture Rx is repeated at least for the number of times transmission events are performed. Further, the setting of receive apertures Rx may be performed each time a transmission event is performed as described above, or alternatively, receive apertures Rx for multiple transmission events having been performed may be set at once after the completion of the transmission events.

Further, the receive aperture setter 1043 outputs information indicating the positions of the receive transducer elements composing the receive aperture Rx to the data storage 107, via the control unit 108.

The data storage 107 outputs the information indicating the positions of the receive transducer elements composing the receive aperture Rx along with receive signal sequences for the receive transducer elements to each of the transmission time calculator 1044, the receive time calculator 1045, the delay processor 1047, and the weight calculator 1048.

iii) Transmission Time Calculator 1044

The transmission time calculator 1044 is a circuit that, for each transmission event, calculates a transmission time for each measurement point P that is included in the target area Bx for the transmission event. The transmission time for a given measurement point P is the time amount required for transmitted ultrasound to arrive at the measurement point P. The transmission time calculator 1043 acquires information indicating the positions of the transmission transducer elements for a given transmission event from the data storage 107, and information indicating the position of the target area Bx for the transmission event, which includes the ultrasound main irradiation area Ax, from the target area setter 1042. Based on such information, the transmission time calculator 1043, for each measurement point Pij included in the target area Bx, calculates the transmission time required for transmitted ultrasound to arrive at the measurement point Pij.

Figure 7A:
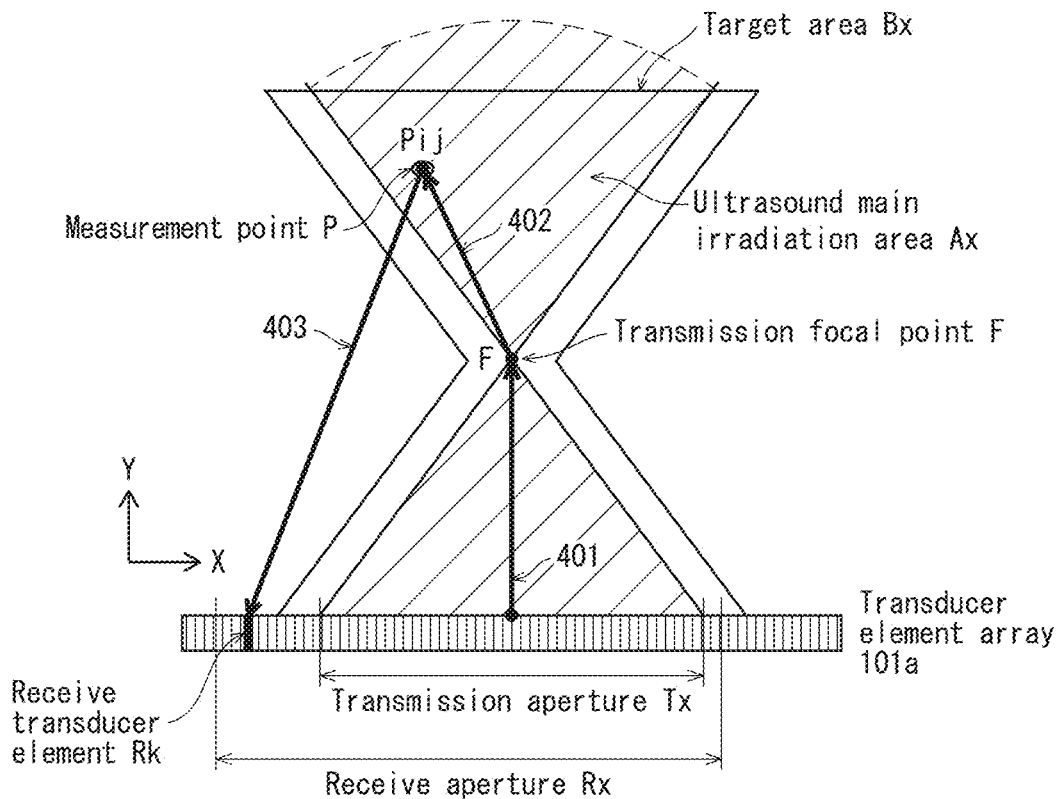
FIG. 7A is a schematic pertaining to embodiment 1, illustrating one propagation path of ultrasound that is transmitted from the transmission aperture Tx and arrives at a receive transducer element Rk via a measurement point Pij.
Figure 7B:
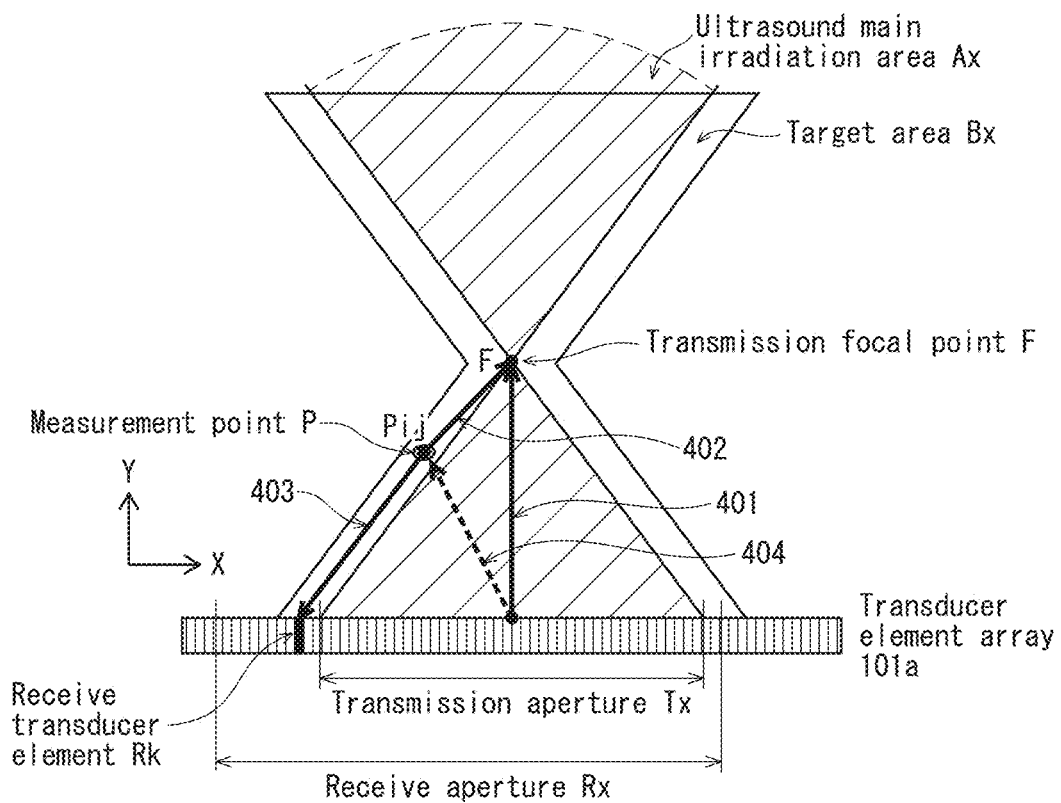
FIG. 7B is a schematic pertaining to embodiment 1, illustrating another propagation path of ultrasound that is transmitted from the transmission aperture Tx and arrives at a receive transducer element Rk via a measurement point Pij.

Each of FIGS. 7A and 7B is a schematic illustrating a propagation path of ultrasound that is transmitted from the transmission aperture Tx for a transmission event, is then reflected at a measurement point Pij that is included in the target area Bx for the transmission event, and finally arrives at a receive transducer element Rk of the receive aperture Rx. Specifically, FIG. 7A illustrates the propagation path of ultrasound for a measurement point Pij located deeper than the transmission focal depth, whereas FIG. 7B illustrates the propagation path of ultrasound for a measurement point Pij located shallower than the transmission focal depth. Note that when comparing the position of a measurement point Pij located deeper than the transmission focal depth and the position of a measurement point Pij located shallower than the transmission focal depth, the measurement point Pij located deeper than the transmission focal depth is located relatively far from the probe and the measurement point Pij located shallower than the transmission focal depth is located relatively near to the probe.

Following emission of ultrasound from the transmission aperture Tx, the wavefront of ultrasound converges at the transmission focal point F after proceeding along the path 401. Subsequently, the wavefront spreads out once again and arrives at the measurement point Pij. When there is a change in acoustic impedance at the measurement point Pij, transmitted ultrasound generates ultrasound reflection, which is received by the receive transducer elements Rk of the receive aperture Rx. The transmission focal point F is preset in advance upon designing of the transmission beam former 103. Thus, the length of the path 402 from the transmission focal point F to the measurement point Pij can be calculated geometrically.

The following describes how the transmission time is calculated in further detail. Here, note that the calculation of the transmission times for measurement points Pij located outside the ultrasound main irradiation area Ax is performed in the same manner as the calculation of transmission time for measurement points Pij located inside the ultrasound main irradiation area Ax.

First, the calculation of a transmission time for a measurement point Pij located deeper than the transmission focal depth is described, with reference to FIG. 7A. A transmission time for a measurement point Pij located deeper than the transmission focal depth is calculated assuming that ultrasound transmitted from the transmission aperture Tx arrives at the transmission focal point F by traveling along path 401, and then arrives at the measurement point Pij by traveling along path 402 from the transmission focal point F. As such, the transmission time for such a measurement point Pij is the total of the time amount required for transmitted ultrasound to travel through path 401 and the time amount required for transmitted ultrasound to travel through path 402. Specifically, the transmission time for such a measurement point Pij can be calculated, for example, by dividing the total of the lengths of paths 401 and 402 by the velocity at which ultrasound propagates within the subject.

In the meantime, the following describes the calculation of a transmission time for a measurement point Pij located shallower than the transmission focal depth, with reference to FIG. 7B. A transmission time for a measurement point Pij located shallower than the transmission focal depth is calculated assuming that the time amount required for ultrasound transmitted from the transmission aperture Tx to arrive at the transmission focal point F by travelling along path 401 equals the time amount required for ultrasound transmitted from the transmission aperture Tx to travel along path 404 to arrive at the measurement point Pij and then travel along path 402 to arrive at the transmission focal point F from the measurement point Pij. As such, the transmission time for such a measurement point Pij is calculated by subtracting the time amount required for transmitted ultrasound to travel through the path 402 from the time amount required for transmitted ultrasound to travel through the path 401. Specifically, a transmission time for such a measurement point Pij can be calculated, for example, by dividing the value acquired by subtracting the length of path 401 from the length of path 401, by the velocity at which ultrasound propagates within the subject.

Note that in the present embodiment, a transmission time for a measurement point Pij located at the transmission focal depth is calculated in the same way as the transmission time for a measurement point Pij located deeper than the transmission focal depth. That is, a transmission time for a measurement point Pij located at the transmission focal depth is calculated by using the total of the time amount required for transmitted ultrasound to travel through path 401 and the time amount required for transmitted ultrasound to travel through path 402. Alternatively, a transmission time for a measurement point Pij located at the transmission focal depth may be calculated in the same way as the transmission time for a measurement point Pij located shallower than the transmission focal depth, or that is by using a value obtained by subtracting the time amount required for transmitted ultrasound to travel through the path 402 from the time amount required for transmitted ultrasound to travel through the path 401. However, it should be noted that in either case, it is preferable that for a single transmission event, the calculation of transmission times for multiple measurement points Pij located at the transmission focal depth be performed according to the same one of the above-described methods. This is since, when in response to a single transmission event, the calculation of transmission times for some measurement points Pij located at the transmission focal depth is performed by using the calculation method for measurement points Pij located deeper than the transmission focal depth and the calculation of transmission times for the rest of the measurement point Pij located at the transmission focal depth is performed by using the calculation method for measurement points Pij located shallower than the transmission focal depth, a considerable gap may occur between the transmission times of two measurement points Pij adjacent in the transducer element array direction. This may result in insufficient image quality improvement.

For each transmission event, the transmission time calculator 1044 calculates the transmission time for each measurement point Pij in the target area Bx for the transmission event. That is, the transmission time calculator 1044 calculates, for each measurement point Pij, the time amount required for transmitted ultrasound to arrive at the measurement point Pij. Further, the transmission time calculator 1044 outputs the transmission time so calculated to the delay amount calculator 1046.

iv) Receive Time Calculator 1045

The receive time calculator 1045 is a circuit that calculates, for each measurement point P, a receive time required for ultrasound reflection from the measurement point P to arrive at each receive transducer element Rk of the receive aperture Rx. For a given transmission event, the receive time calculator 1045 acquires information indicating the positions of the receive transducer elements Rk for the given transmission event from the data storage 107, and acquires the information indicating the position of the target area Bx for the given transmission event from the target area setter 1042. Based on such information, the receive time calculator 1045, for each measurement point Pij in the target area Bx, calculates the receive time required for transmitted ultrasound to arrive at each receive transducer element Rk after being reflected at the measurement point Pij.

As already discussed above, transmitted ultrasound arriving at a measurement point Pij generates ultrasound reflection when there is a change in acoustic impedance at the measurement point Pij. The reflected ultrasound is then received by receive transducer elements Rk of the receive aperture Rx. As discussed above, the receive time calculator 1045 acquires information indicating the positions of the receive transducer elements Rk of the receive aperture Rx from the data storage 107. Accordingly, the receive time calculator 1045 is able to geometrically calculate the length of paths 403 leading from the measurement point Pij to the respective receive transducer elements Rk.

For each transmission event, the receive time calculator 1045 calculates the receive time for each measurement point Pij that is included in the target area Bx for the transmission event. That is, the receive time calculator 1045 calculates, for each measurement point Pij, the time required for transmitted ultrasound to arrive at each receive transducer element Rk after being reflected at the measurement point Pij. Further, the receive time calculator 1045 outputs the receive time so calculated to the delay amount calculator 1046.

v) Delay Amount Calculator 1046

The delay amount calculator 1046 is a circuit that calculates, for each receive transducer element Rk, a total propagation time based on the transmission time and the receive time for the receive transducer element Rk. Further, the delay amount calculator 1046 calculates, for each receive transducer element Rk, a delay amount to be applied to a receive signal sequence for the receive transducer element Rk. In specific, the delay amount calculator 1046 acquires, from the transmission time calculator 1044, the transmission time required for ultrasound waves to arrive at a measurement point Pij. Further, for each receive transducer element Rk, the delay amount calculator 1046 acquires, from the receive time calculator 1045, the receive time required for ultrasound to be reflected at the measurement point Pij and arrive at the receive transducer element Rk. Then, the delay amount calculator 1046, for each receive transducer Rk, calculates a total propagation time required for transmitted ultrasound to arrive at the receive transducer element Rk. Further, based on the difference between total propagation times for the receive transducer elements Rk, the delay amount calculator 1046 calculates a delay amount for each receive transducer element Rk. For each measurement point P that is included in the target area Bx, the delay amount calculator 1046 calculates, for each receive transducer element Rk, the delay amount to be applied to a receive signal sequence for the receive transducer element Rk, and outputs the delay amounts to the delay processor 1047.

vi) Delay Processor 1047

The delay processor 1047 is a circuit that specifies, for each receive transducer element Rk, a receive signal based on reflected ultrasound from a measurement point Pij. In specific, for each receive transducer element Rk, the delay processor 1047 specifies a receive signal corresponding to the delay amount for the receive transducer element Rk from the receive signal sequence for the receive transducer element Rk.

More specifically, for each transmission event, the delay processor 1047 acquires, for each receive transducer element Rk, information indicating the position of the receive transducer element Rk from the receive aperture setter 1043, the receive signal sequence for the receive transducer element Rk from the data storage 107, and the delay amount to be applied to the receive signal sequence of the receive transducer element Rk from the delay amount calculator 1046. In addition, for each transmission event, the delay processor 1047 acquires the information indicating the position of the target area Bx from the target area setter 1042. Further, for each receive transducer element Rk, the delay processor 1047 specifies a receive signal based on reflected ultrasound from a measurement point Pij. In specific, the delay processor 1047 specifies, from the receive signal sequence for the receive transducer element Rk, a receive signal corresponding to a time point after subtraction of the delay amount for the receive transducer element Rk. The delay processor 1047 outputs the receive signal so specified to the sum calculator 1049.

vii) Weight Calculator 1048

The weight calculator 1048 is a circuit that calculates a weight sequence (reception apodization weight) for the receive transducer elements Rk, so that the maximum weight is set with respect to the receive transducer element located at the center of the receive aperture Rx in the transducer element array direction.

As illustrated in FIG. 6, the weight sequence is a numerical sequence of weight coefficients that are to be applied to receive signals for the receive transducer elements composing the receive aperture Rx. The weight sequence indicates weights that are distributed symmetrically with respect to the measurement point Pij. As the shape of distribution of the weights indicated by the weight sequence, any shape is applicable, including but not limited to a hamming window, a hanning window, and a rectangular window. The weight sequence is set so that the maximum weight is set with respect to the receive transducer element located at the center position of the receive aperture Rx in the transducer element array direction, and the central axis of the weight distribution corresponds to the center axis Rxo of the receive aperture Rx. The weight calculator 1048 uses as input information indicating the positions of the receive transducer elements Rk, which is output from the receive aperture setter 1043, and outputs the weight sequence for the receive transducer elements Rk to the sum calculator 1049.

viii) Sum Calculator 1049

The sum calculator 1049 is a circuit that generates a delayed-and-summed acoustic line signal for each measurement point P, by using as input the specified receive signals for the receive transducer elements Rk, which are output from the delay processor 1047, and summing together the specified receive signals. Alternatively, the sum calculator 1049 may generate an acoustic line signal for each measurement point P by using as input the weight numerical sequence for the receive transducer elements Rk, which is output from the weighting calculator 1048, multiplying the specified receive signal for each receive transducer element Rk with a corresponding weight, and summing the weighted receive signals. The sum calculator 1049 sums the receive signals for the receive transducer elements Rk, after the receive signals have been put in the same phase by the delay processor 1047. Due to this, the sum calculator 1049 is capable of increasing the S/N ratio of the receive signals received by the receive transducer elements Rk based on reflected ultrasound from the measurement point Pij, and receive signals for the measurement point Pij can be extracted.

As a result of one transmission event and processing accompanying the transmission event, an acoustic line signal is generated for each measurement point P in the target area Bx for the transmission event, which includes the ultrasound main irradiation area Ax. Further, by repetitively performing transmission events while shifting the transmission aperture Tx in the transducer element array direction by the shift amount Mp each time, all of the transducer elements 101a in the probe 101 perform ultrasound transmission. Due to this, a frame acoustic line signal, which is a combination of acoustic line signals corresponding to one frame, is generated.

In the present embodiment, acoustic line signals for respective measurement points, which compose the frame acoustic line signal and each of which is generated by combining a plurality of acoustic lines signals corresponding to the measurement point that are included in different sub-frame acoustic line signals, are each referred to as a combined acoustic line signal for the measurement point.

The sum calculator 1049, for each transmission event, generates a sub-frame acoustic line signal being a combination of acoustic line signals for every measurement point Pij within the target area Bx for the transmission event. Further, the sum calculator 1049 outputs the sub-frame acoustic line signals so generated to be stored in the data storage 107.

(5) Synthesizer 1140

Figure 8:
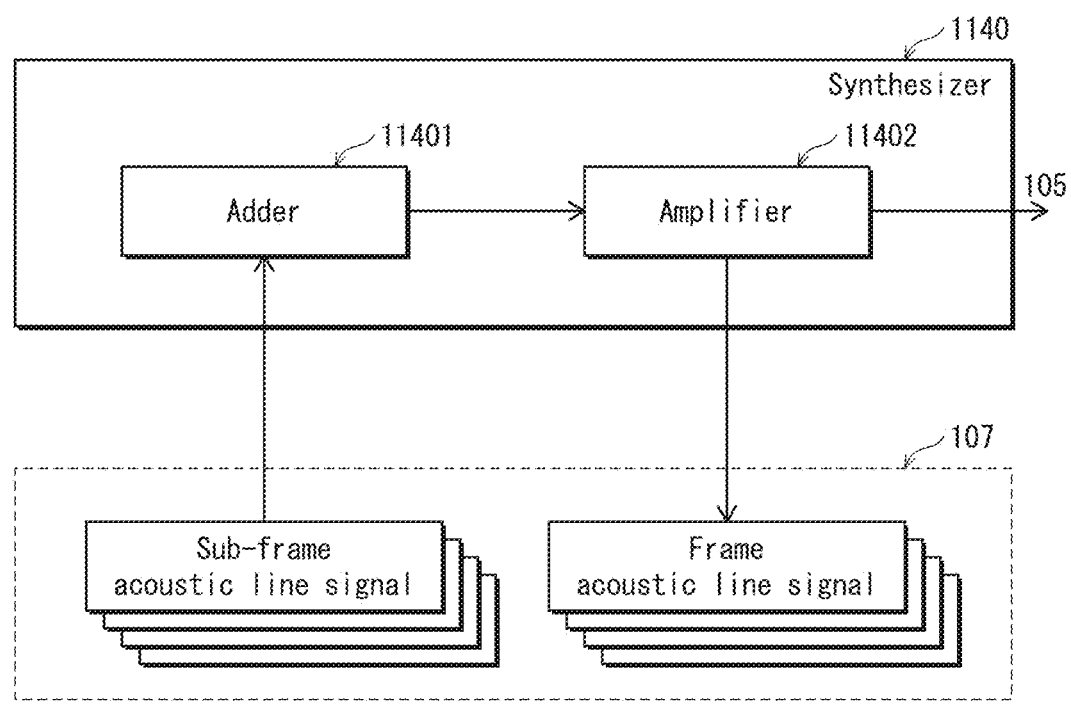
FIG. 8 is a functional block diagram illustrating the structure of a synthesizer 1140 pertaining to embodiment 1.

The synthesizer 1140 is a circuit that generates a frame acoustic line signal by combining a plurality of sub-frame acoustic line signals each generated for one transmission event. FIG. 8 is a functional block diagram illustrating the structure of the synthesizer 1140. As illustrated in FIG. 8, the synthesizer 1140 includes an adder 11401 and an amplifier 11402.

The following describes the structure of each functional block of the synthesizer 1140.

i) Adder 11401

The adder 11401, after the generation of a series of sub-frame acoustic line signals necessary for generating one frame acoustic line signal is completed, reads out the sub-frame acoustic line signals from the data storage 107. Further, the adder 11401 generates a frame acoustic line signal by combining the plurality of sub-frame acoustic line signals. The combining of the sub-frame acoustic line signals is performed according to the positions of the measurement points Pij, such that in the process, a combined acoustic line signal is generated for each measurement point Pij. In specific, the adder 11401 generates a combined acoustic line signal for a given measurement point Pij by combining a plurality of acoustic line signals corresponding to the measurement point Pij that are included in different sub-frame acoustic line signals. Due to this, acoustic line signals for the same measurement point that are included in different sub-frame acoustic line signals are combined, to generate a combined acoustic line signal for the measurement point.

Figure 9:
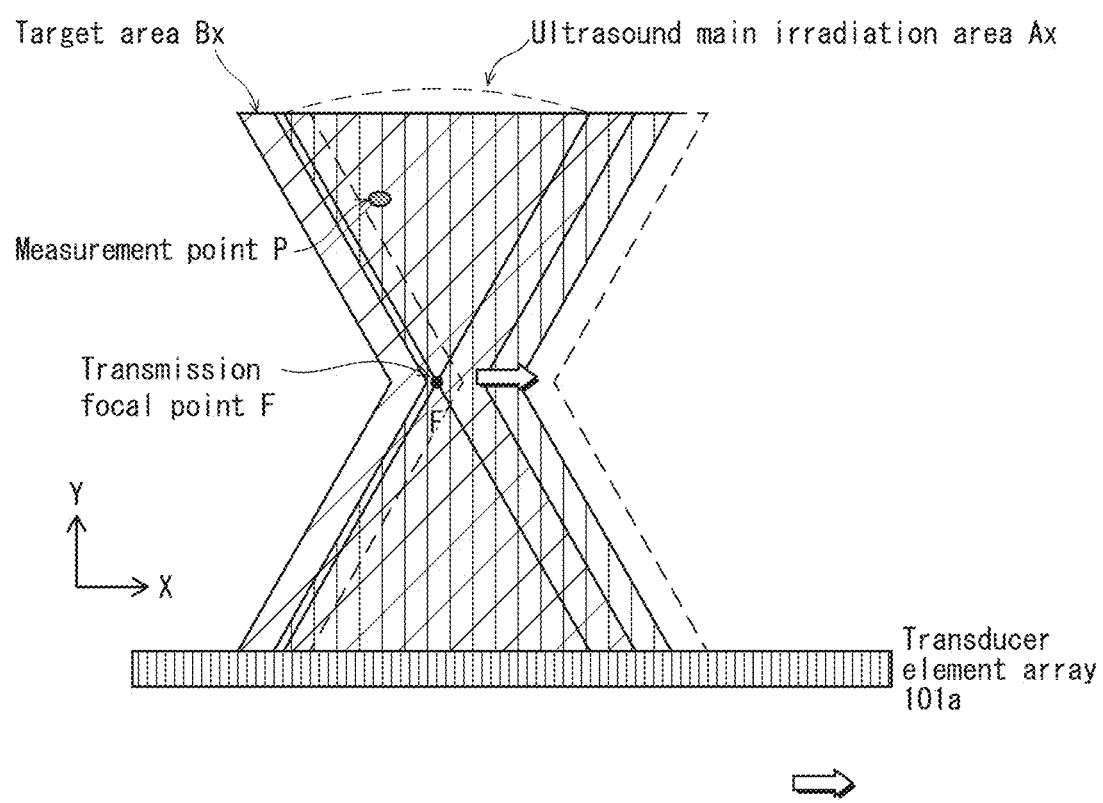
FIG. 9 is a schematic illustrating processing by an adder 11401 pertaining to embodiment 1 for generating a combined acoustic line signal.

FIG. 9 is a schematic illustrating processing by the adder 11401 for generating a combined acoustic line signal. As already discussed above, ultrasound transmission is performed by repetitively performing transmission events while shifting the transmission transducer element array (i.e., the transmission aperture Tx) in the transducer element array direction by the shift amount Mp each time. Due to this, target areas Bx for two consecutive transmission events, each of which including the ultrasound main irradiation area Ax based on one of the consecutive transmission events, differ in position from one another in the transducer element array direction by the shift amount Mp. Thus, a frame acoustic line signal covering all target areas Bx can be generated by combining sub-frame acoustic line signals based on the positions of the measurement points Pij from which the acoustic lines signals included in the sub-frame acoustic line signals are acquired.

Further, for a measurement point included in multiple target areas Bx, values of a plurality of acoustic line signals included in different sub-frame acoustic line signals are summed. Thus, the combined acoustic line signal for such a measurement point may indicate a great value, depending upon the number of target areas Bx in which the measurement point is included. In the following, the number of different target areas Bx in which a given measurement point is included is referred to as an overlap count of the measurement point, and the maximum value of the overlap count in the transducer element array direction is referred to as a maximum overlap count. As already described above, each target area Bx is set so that at the transmission focal depth, the width Wf of the target area Bx in the transducer element array direction is equal to or greater than the shift amount Mp. Due to this, at the transmission focal depth, the overlap count is at least one (not zero), or in other words, each measurement point Pij at the transmission focal depth is included in at least one target area Bx.

Figure 10A:
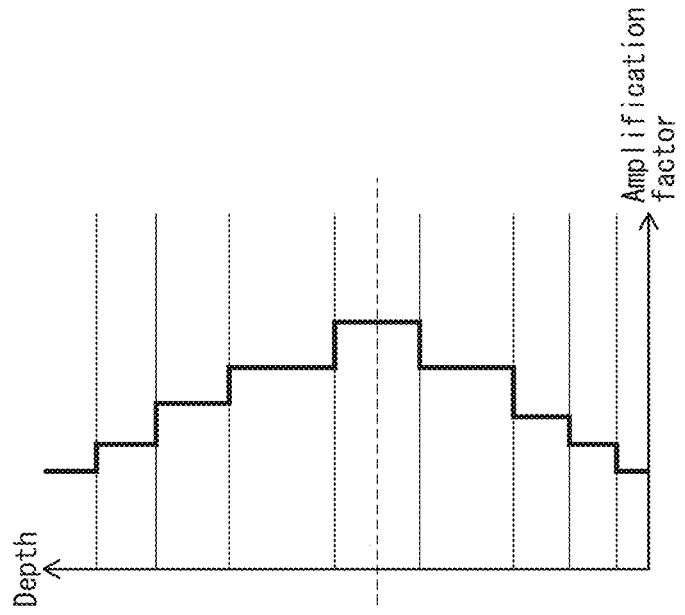
FIG. 10A is a schematic pertaining to embodiment 1, providing an overview of maximum overlap counts for combined acoustic line signals.

Further, in the present embodiment, the target area Bx has an hourglass-shape. Due to this, the overlap count and the maximum overlap count differ in the depth direction of the subject, as illustrated in FIG. 10A. Accordingly, combined acoustic line signals for measurement points at different depths also have different values.

Note that in combining sub-frame acoustic line signals based on the positions of the measurement points Pij from which the acoustic lines signals included in the sub-frame acoustic line signals are acquired to generate combined acoustic line signals for the respective measurement points, the adder 11401 may add weights in accordance with the positions of the measurement points Pij.

The adder 11401 outputs the frame acoustic line signal so generated to the amplifier 10492.

ii) Amplifier 11402

As already described above, the value of a combined acoustic line signal for a given measurement point is dependent upon the maximum overlap count at the measurement point. In addition, the overlap count also changes in the depth direction. In order to moderate such variation between values of different combined acoustic line signals, the amplifier 11402, in combining the combined acoustic line signals to generate the frame acoustic line signal, performs amplification of multiplying the combined acoustic line signals by amplification factors. Here, the amplifier 11402 determines an amplification factor for a given combined acoustic line signal according to the number of acoustic line signals combined to yield the combined acoustic line signal.

Figure 10B:
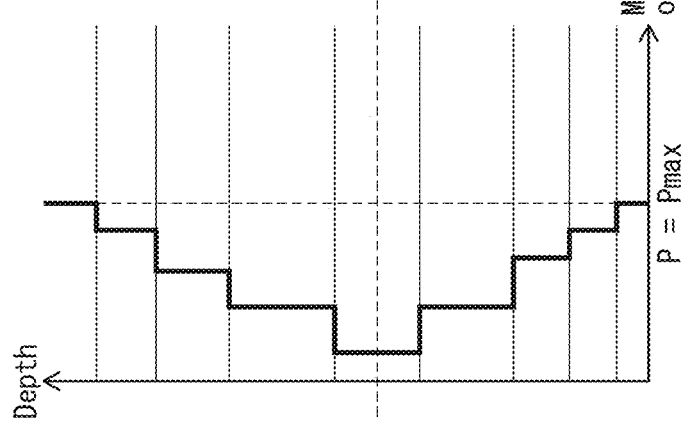
FIG. 10B is a schematic pertaining to embodiment 1, providing an overview of amplification by an amplifier 11402 that is based on the maximum overlap counts for the combined acoustic line signals.

FIG. 10B is a schematic providing an overview of the amplification performed by the amplifier 11402. The maximum overlap count varies in the depth direction, as illustrated in FIG. 10A. Thus, to compensate with this variation in maximum overlap count, the amplifier 11402 multiplies the combined acoustic line signals by respective amplification factors that are based on the maximum overlap counts and vary in the depth direction, as illustrated in FIG. 10B. Here, the amplification factors used by the amplifier 11402 are such that, the greater the width of the target area Bx in the transducer element array direction, the greater the difference between the amplification factors in the depth direction. This moderates a difference between values of combined acoustic line signals deriving from the difference in overlap counts in the depth direction, and thus, the values of the combined acoustic line signals after the amplification are averaged out in the depth direction. That is, the amplification performed by the amplifier 11402 is gain equalization in the depth direction.

Further, the amplifier 11402 may also multiply the combined acoustic line signals by amplification factors varying in the transducer element array direction that are calculated based on overlap counts, when overlap counts vary in the transducer element array direction. This moderates a difference between values of combined acoustic line signals deriving from the difference in overlap counts in the transducer element array direction, and thus, the values of the combined acoustic line signals after the amplification are averaged out in the transducer element array direction.

Here, note that the amplifier 11402 may generate the frame acoustic line signal by combining amplified combined acoustic line signals for respective measurement points.

<Operations>

The following describes the operations of the ultrasound diagnostic device 100 having the structure described up to this point.

Figure 11:
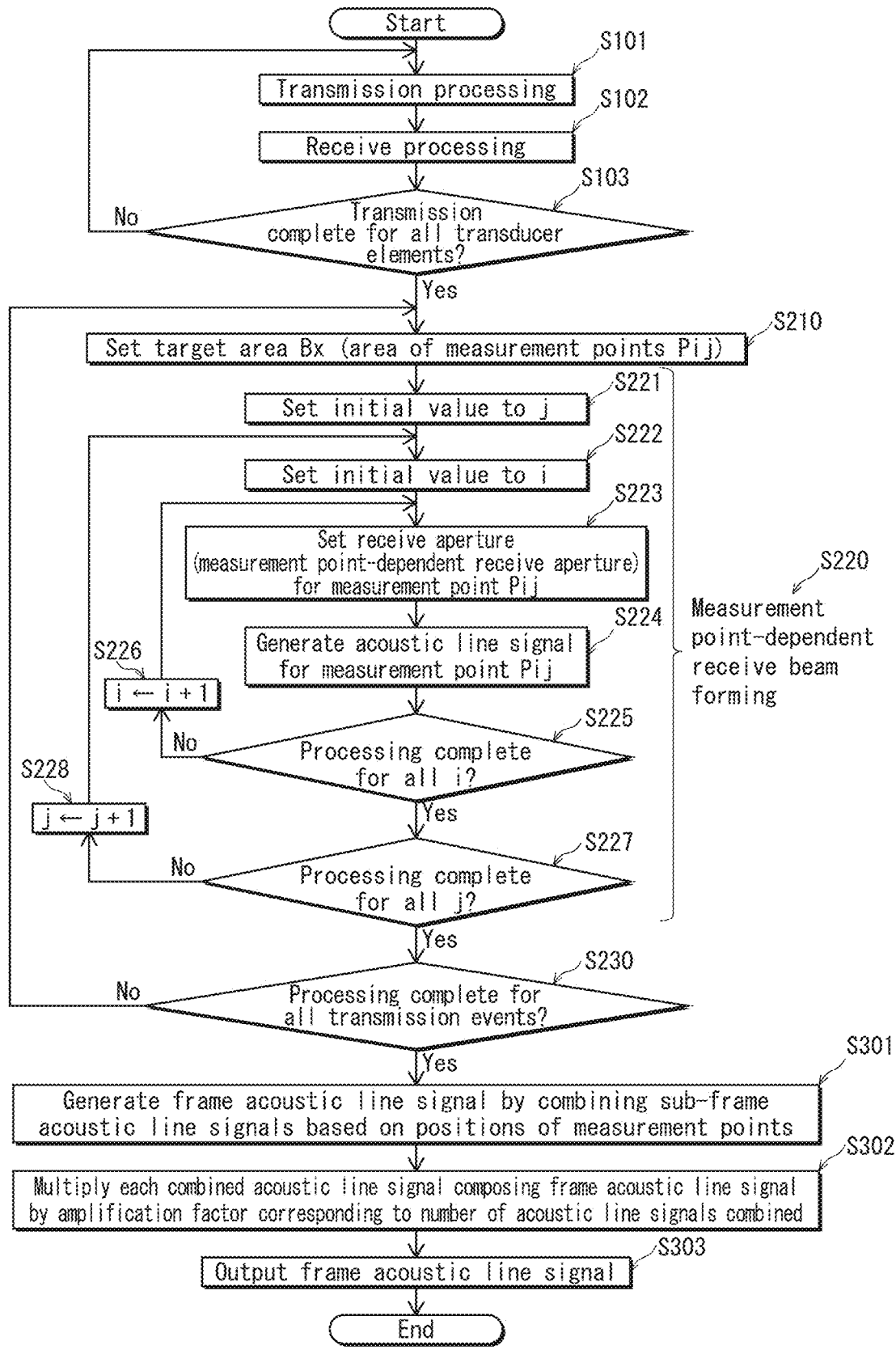
FIG. 11 is a flowchart illustrating beam forming by the receive beam former 104 pertaining to embodiment 1.

FIG. 11 is a flowchart illustrating beam forming by the receive beam former 104.

First, in Step S101, the transmitter 1031 performs transmission processing (a transmission event) of supplying a transmission signal causing transmission of an ultrasound beam to each transmission transducer element of the transmission aperture Tx.

In Step S102, the receiver 1040 generates receive signal sequences based on electric signals yielded through the reception of reflected ultrasound by the probe 101, and outputs the receive signal sequences to be stored in the data storage 107. Then, a determination is made of whether or not all transducer elements 101a of the probe 101 have performed ultrasound transmission (S103). When one or more of the transducer elements 101a have not yet performed ultrasound transmission, processing returns to Step S101, which results in another transmission event being executed by shifting the transmission aperture Tx in the transducer element array direction by a shift amount Mp. Meanwhile, when all of the transducer elements 101a have performed ultrasound transmission, processing proceeds to Step S210.

In Step S210, the target area setter 1042 sets a target area Bx for a processing-target transmission event based on information indicating the position of the transmission aperture Tx for the processing-target transmission event and the shift amount Mp. In the initial loop of processing, the target area setter 1042 sets a target area Bx including the ultrasound main irradiation area Ax for the initial transmission event, which can be calculated from the transmission aperture Tx for the initial transmission event.

Subsequently, processing proceeds to measurement-point dependent beam forming (Step S220 (including Steps S221 through S228)). In Step S220, first, coordinate values i and j indicating a position of a measurement point Pij that is included in the target area Bx for the processing-target transmission event are initialized (set to the respective minimum possible values in the target area Bx) (Steps S221 and S222). Then, the receive aperture setter 1043 sets a receive aperture Rx for the current measurement point so that the center of the receive aperture Rx corresponds to a transducer element Xk that is spatially closest to the current measurement point Pij (Step S223).

Subsequently, an acoustic line signal is generated for the current measurement point Pij (Step S224).

Figure 12:
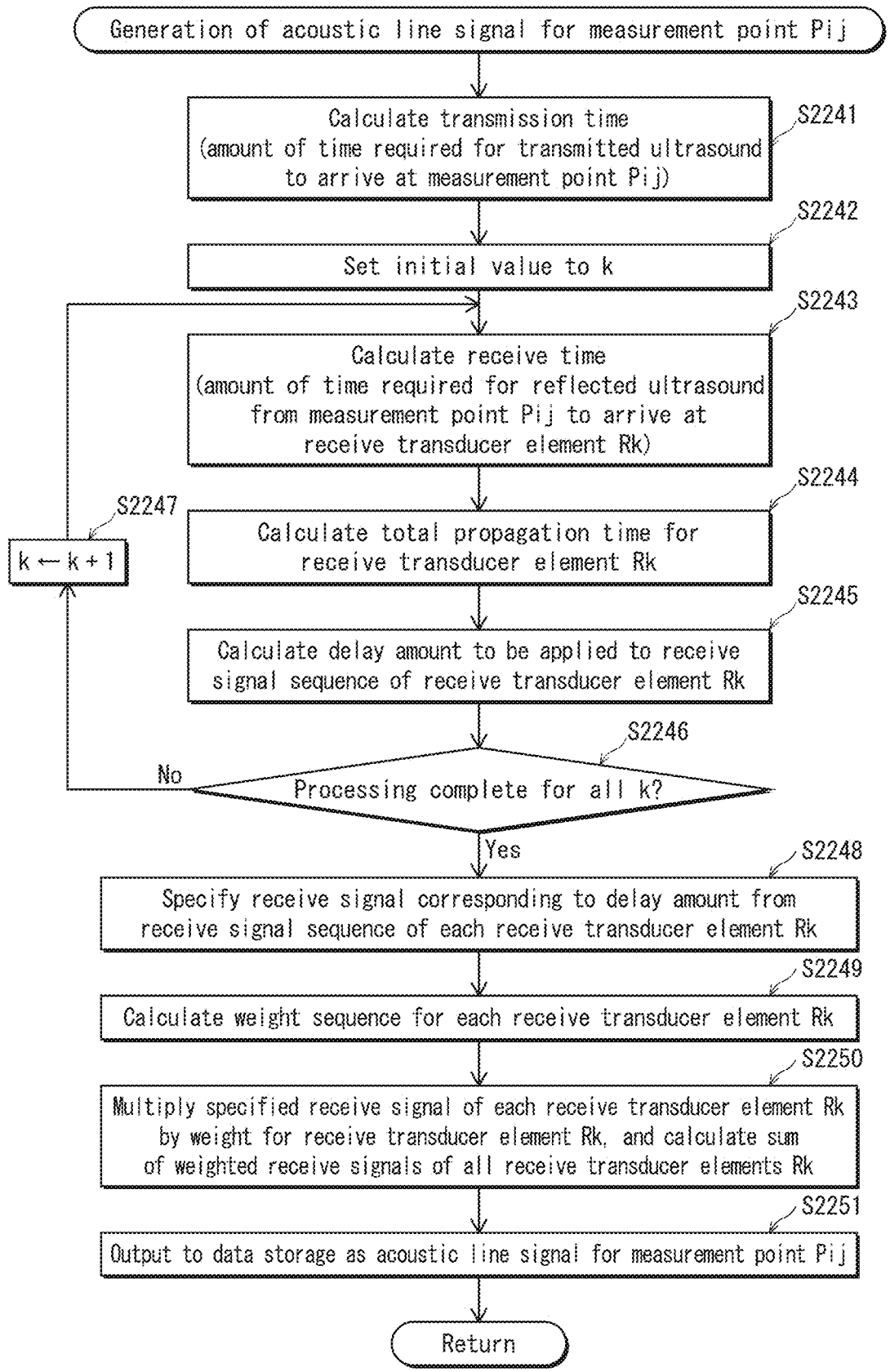
FIG. 12 is a flowchart illustrating operations of the receive beam former 104 pertaining to embodiment 1 for generating an acoustic line signal for a measurement point Pij.
Figure 13:
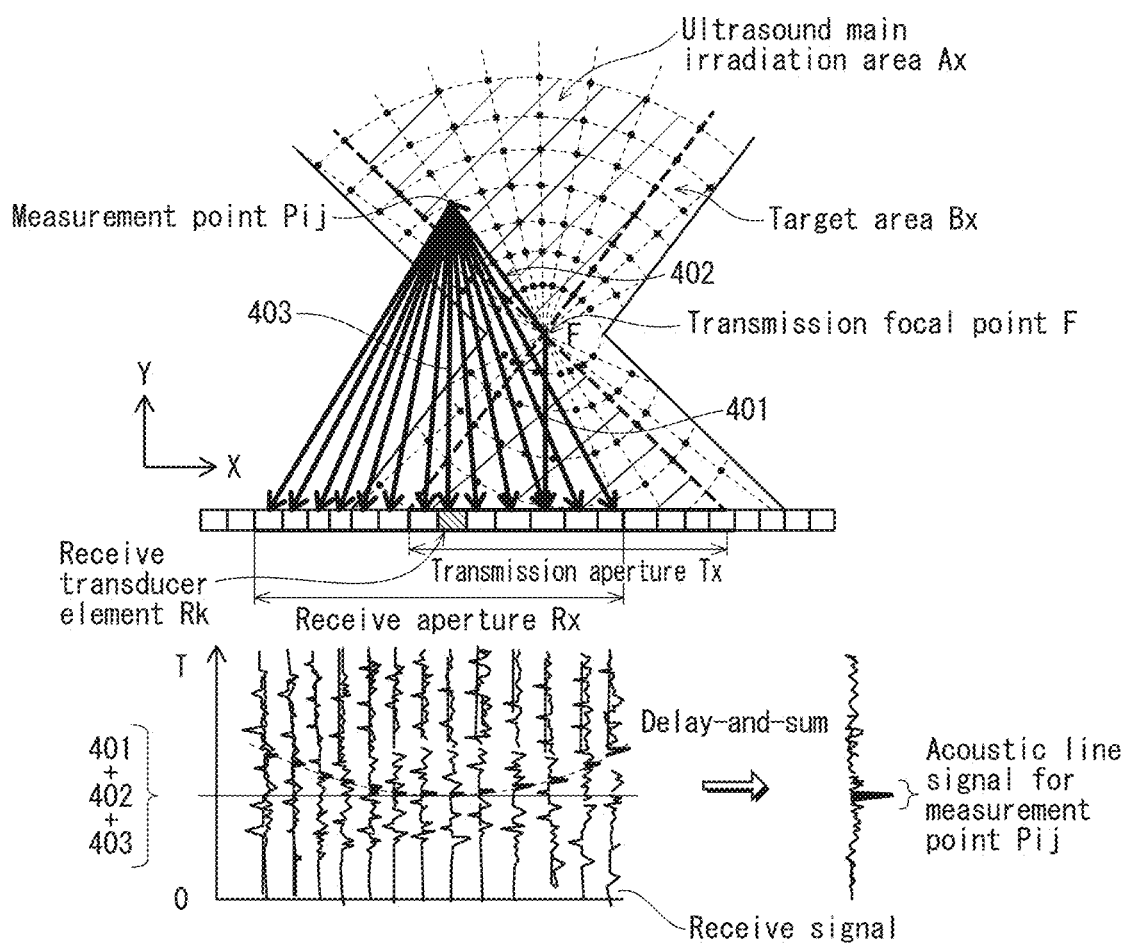
FIG. 13 is a schematic for explaining the operations of the receive beam former 104 pertaining to embodiment 1 for generating an acoustic line signal for a measurement point Pij.

The following describes the operations in Step S224 for generating an acoustic line signal for the current measurement point Pij. FIG. 12 is a flowchart illustrating the operations of the receive beam former 104 for generating the acoustic line signal for the current measurement point Pij. FIG. 13 is a schematic for explaining the operations of the receive beam former 104 for generating the acoustic line signal for the current measurement point Pij.

First, in Step S2241, the transmission time calculator 1044 calculates, for the current measurement point Pij, a transmission time required for transmitted ultrasound to arrive at the current measurement point Pij. As already described above, the current measurement point Pij is a measurement point included in the target area Bx for the processing-target transmission event. Here, (i) when the current measurement point Pij is located at the transmission focal depth or deeper than the transmission focal depth, the transmission time for the current measurement point Pij is calculated by dividing, by ultrasound velocity cs, the geometrically-calculatable length of a path (combination of paths 401 and 402) starting at a transmission transducer element in the transmission aperture Tx and reaching the current measurement point Pij via the transmission focal point F. Meanwhile, (ii) when the current measurement point Pij is located shallower than the transmission focal depth, the transmission time for the current measurement point is calculated by dividing, by the ultrasound velocity cs, a value (401-402) obtained by subtracting the geometrically-calculatable length of the path from the transmission focal point F to the current measurement point Pij from the geometrically-calculatable length of the path from a transmission transducer element in the transmission aperture Tx to the transmission focal point F.

Subsequently, value k, which indicates the position of a target receive transducer element Rk of the receive aperture Rx, is initialized (set to the minimum possible value in the receive aperture Rx) (Step S2242). Then, the receive time for the target receive transducer element Rk is calculated (Step S2243). The receive time is the time required for transmitted ultrasound to arrive at the target receive transducer element Rk after being reflected at the current measurement point Pij. The receive time for the target receive transducer element Rk can be calculated by dividing, by the ultrasound velocity cs, the geometrically-calculatable length of the path 403 from the current measurement point Pij to the target receive transducer element Rk. Further, from a sum of the transmission time and the receive time for the target receive transducer element Rk, the total propagation time required for ultrasound transmitted from the transmission aperture Tx to arrive at the target receive transducer element Rk after being reflected at the current measurement point Pij is calculated (Step S2244). Further, based on the difference in total propagation time between different receive transducer elements Rk composing the receive aperture Rx, the delay amount for the target receive transducer element Rk is calculated (Step S2245).

Subsequently, a determination is performed of whether or not a delay amount has been calculated for every receive transducer element Rk composing the receive aperture Rx (Step S2246). When a delay amount has not yet been calculated for one or more of the receive transducer elements Rk, the value k is incremented (Step S2247), and a delay amount for another receive transducer element Rk is calculated (Step S2243). Meanwhile, when a delay amount has been calculated for every receive transducer element Rk composing the receive aperture Rx, processing proceeds to Step S2248. Note that at this point, a delay amount for the current measurement point Pij has already been calculated for each receive transducer element Rk of the receive aperture Rx. The delay amount for a given receive transducer element Rk indicates delay with which reflected ultrasound from the current measurement point Pij arrives at the receive transducer element Rk.

In Step S2248, the delay processor 1047, for each receive transducer element Rk, specifies a receive signal based on reflected ultrasound from the current measurement point Pij. Here, the delay processor 1047 specifies, from a receive signal sequence corresponding to each receive transducer element Rk, a receive signal corresponding to a time point after subtraction of the delay amount for the receive transducer element Rk.

Subsequently, the weight calculator 1048 calculates a weight sequence for the receive transducer elements Rk of the current receive aperture Rx, so that the maximum weight is set with respect to the receive transducer element located at the center position of the receive aperture Rx in the transducer element array direction (S2249). Then, the sum calculator 1049 generates an acoustic line signal for the current measurement point Pij by multiplying the specified receive signal for each receive transducer element Rk by a weight corresponding to the receive transducer element Rk, and summing the weighted receive signals for the different receive transducer elements Rk (Step S2250). Following this, the sum calculator 1049 outputs the acoustic line signal for the current measurement point Pij to the data storage 107 to be stored in the data storage 107 (Step S2251).

Referring to FIG. 11 once again, subsequently, an acoustic line signal is generated for each measurement point Pij (each illustrated in FIG. 13 as a black dot) that is included in the target area Bx for the processing-target transmission event, by repeating Steps S223, S224 while incrementing the coordinate values i and j (Steps S225, S227). Subsequently, a determination is performed of whether or not an acoustic line signal has been generated for every measurement point Pij within the target area Bx. When an acoustic line signal has not yet been generated for every measurement point Pij within the target area Bx, the coordinate values i and j are incremented, yielding an acoustic line signal for another measurement point Pij (Step S224). Meanwhile, when an acoustic line signal has already been generated for every measurement point Pij within the target area Bx, processing proceeds to Step S230. At this point, an acoustic line signal has already been generated for each measurement point P that is included in the target area Bx corresponding to the processing-target transmission event, and the acoustic line signals have been output to and stored to the data storage 107. In other words, a sub-frame acoustic line signal for the processing-target transmission event has been generated, and output to and stored to the data storage 107.

Subsequently, a determination is performed of whether or not a sub-frame acoustic line signal has been generated for each transmission event having been performed (Step S230). When sub-frame acoustic line signals have not yet been generated for one or more transmission events, processing proceeds to Step S210, where the coordinate values i and j are initialized (set to the respective minimum possible values in the target area Bx for the subsequent transmission event, which can be calculated from the transmission aperture Tx for the subsequent transmission event) (Steps S221 and S222), and then setting of a receive aperture Rx is performed (Step S223). Meanwhile, when sub-frame acoustic line signals have been generated for every transmission event having been performed, processing proceeds to Step S301.

In Step S301, the adder 11401 reads out the sub-frame acoustic line signals stored in the data storage 107, and combines the sub-frame acoustic line signals based on positions of the measurement points Pij. Thus, a combined acoustic line signal is generated for each measurement point Pij, and accordingly, a frame acoustic line signal is generated. Subsequently, the amplifier 11402 multiples each combined acoustic line signal by a corresponding amplification factor that is determined based on the number of acoustic line signals, included in the sub-frame acoustic line signals, that have been combined to yield the combined acoustic line signal (Step S302). Further, the amplifier 11402 outputs the amplified frame acoustic line signal to the ultrasound image generator 105 and the data storage 107 (Step S303), and processing is terminated.

<Conclusion>

As described above, the ultrasound diagnostic device 100 pertaining to the present embodiment, according to the synthetic aperture method, synthesizes acoustic line signals for the same measurement point that are generated in response to different transmission events. This achieves the effect of performing, for multiple transmission events, virtual transmission focusing even for measurement points that are located in depths other than that of the transmission focal point F. This improves spatial resolution and S/N ratio.

In addition, in the ultrasound diagnostic apparatus 100, a target area, which is an area from which a sub-frame acoustic line signal is generated, is set to have a width equal to or greater than the width of the shift amount in the transducer element array direction. Due to this, regardless of the width of the shift amount, a defective area (i.e., an area where overlap count is zero) is not formed between any two target areas corresponding to two consecutive transmission events. Due to this, the ultrasound diagnostic apparatus 100 prevents image quality reduction brought about by the occurrence of such defective areas and is capable of achieving high frame rate, even when the shift amount is provided with a great value.

Further, in the ultrasound diagnostic device 100, the receive aperture setter 1043 selects, as transducer elements composing the receive aperture Rx for each measurement point P, transducer elements forming an array whose center position in the transducer element array direction matches a transducer element that is spatially closest to the measurement point P. Accordingly, the ultrasound diagnostic device 100 performs receive beam forming by using a receive aperture that is not dependent upon ultrasound transmission events but is dependent upon the position of the measurement point P, and that is symmetric with respect to the measurement point P. Due to this, the receive aperture Rx for a given measurement point P does not change (i.e., the same receive aperture Rx is used for the same measurement point P) between different transmission events, between which the transmission focal point F is shifted in the transducer element array direction. Thus, delay-and-sum processing for the same measurement point P is always performed by using the same receive aperture Rx. In addition, in the ultrasound diagnostic device 100, a weight sequence is set so that the closer a receive transducer element is to the measurement point P, the greater the weight applied to the receive transducer element. Due to this, even taking into account the fact that ultrasound decay increases as propagation distance increases, ultrasound reflected from the measurement point P can be used with high efficiency. Accordingly, the ultrasound diagnostic device 100 achieves both high local spatial resolution and high S/N ratio.

<<Modification 1>>

The receive aperture setter 1043 in the ultrasound diagnostic device 100 pertaining to embodiment 1 sets, for each measurement point P, the receive aperture Rx so that the center position of the receive aperture Rx in the transducer element array direction corresponds to a transducer element that is spatially closest to the measurement point P. However, the configuration of the receive aperture Rx may be changed as necessary, as long as acoustic line signals for all measurement points Pij that are included in each target area Bx can be generated by calculating total propagation times and performing delaying based on total propagation paths. As already discussed above, a total propagation time for a given receive transducer element Rk is the time required for ultrasound transmitted from the transmission aperture Tx to reach the receive transducer element Rk after passing through the transmission focal point F and being reflected at the measurement point P.

Modification 1 provides an ultrasound diagnostic device differing from the ultrasound diagnostic device 100 pertaining to embodiment 1 for including a receive aperture setter (a Tx receive aperture setter) that sets, for each transmission event, the receive aperture Rx so that the center position of the receive aperture Rx corresponds to the center position of the transmission aperture Tx for the transmission event. That is, the receive aperture Rx in modification 1 can be referred to as a transmission-dependent receive aperture. Other than the Tx receive aperture setter, the components of the ultrasound diagnostic device pertaining to modification 1 have the same structures and configurations as the corresponding components in the ultrasound diagnostic device 100 described in embodiment 1. Thus, description of such similar components is not provided in the following.

Figure 14:
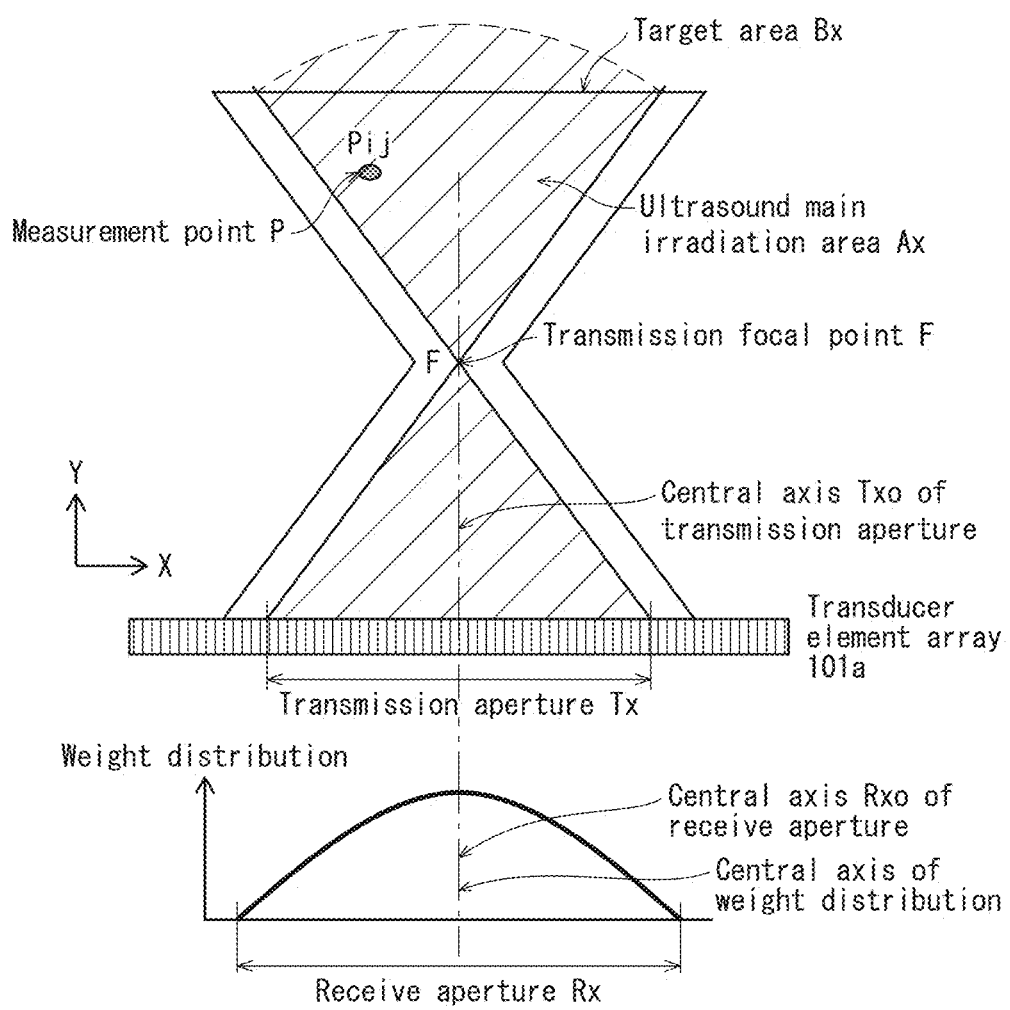
FIG. 14 is a schematic illustrating the relationship between a transmission aperture Tx and a receive aperture Rx set by a Tx receive aperture setter pertaining to modification 1.

FIG. 14 is a schematic illustrating the relationship between a transmission aperture Tx and a receive aperture Rx set by the Tx receive aperture setter. In modification 1, the Tx receive aperture setter sets, for each transmission event, a receive aperture Rx so that the center position of the receive aperture Rx in the transmission element array direction corresponds to the center position of the transmission aperture Tx for the transmission event. Thus, the position of an axis Rxo passing through the center position of the receive aperture Rx corresponds to the position of an axis Txo passing through the center position of the transmission aperture Tx. Further, the receive aperture Rx is symmetric about the transmission focal point F (i.e., has the same number of apertures at both sides of the center position thereof in the transmission element array direction). As such, as the transmission aperture Tx shifts in the transducer element array direction from one transmission event to another, the receive aperture Rx also shifts in the transducer element array direction, following the transmission aperture Tx.

In addition, a weight sequence (so-called reception apodization weight) for the receive transducer elements Rk is calculated, so that the maximum weight is set with respect to the receive transducer element Rk located along the center axis Rxo of the receive aperture Rx and the center axis Txo of the transmission aperture Tx. The weight sequence indicates weights distributed symmetrically with respect to the center axis Txo of the transmission aperture Tx. As the shape of distribution of the weights indicated by the weight sequence, any shape is applicable, including but not limited to a hamming window, a hanning window, and a rectangular window.

<Operations>

Figure 15:
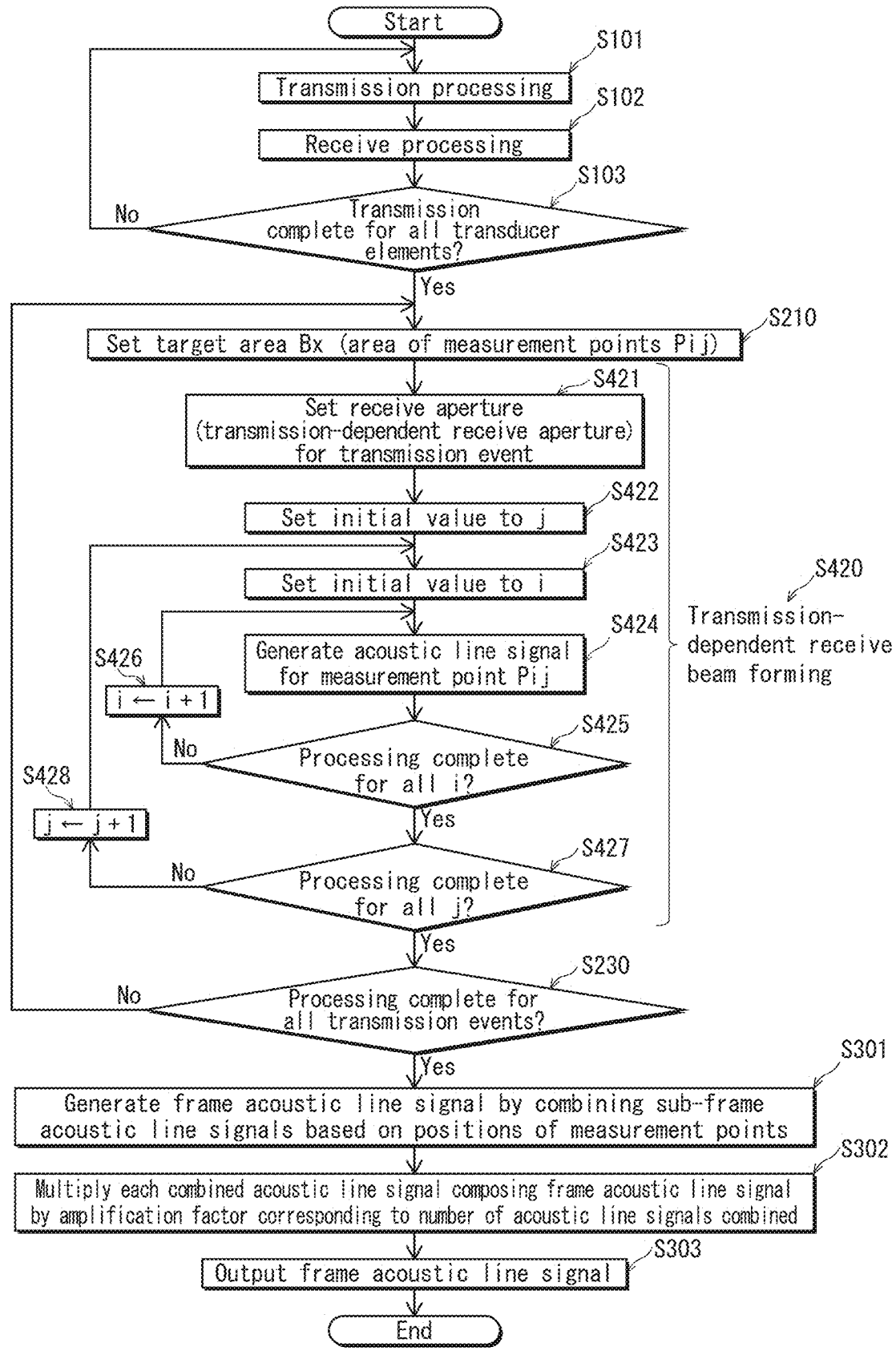
FIG. 15 is a flowchart illustrating beam forming by a receive beam former of an ultrasound diagnostic device pertaining to modification 1.

FIG. 15 is a flowchart illustrating beam forming by a receive beam former of the ultrasound diagnostic device pertaining to modification 1. The flowchart in FIG. 15 differs from the flowchart in FIG. 11 for transmission-dependent dependent beam forming (Step S420 (including Steps S421 through S428)) being performed in place of measurement point-dependent beam forming (Step S220 (including Steps S221 through S228)). Meanwhile, the processing in steps other than Step S420 in the flowchart in FIG. 15 is similar to the processing in the corresponding steps in the flowchart in FIG. 11. Thus, description of such similar processing is not provided in the following.

In Step S420, first, the Tx receive aperture setter sets a receive aperture Rx for a transmission event by selecting receive transducer elements Rk composing a receive transducer element array whose center position matches the center position of the transducer element array composing the transmission aperture Tx for the corresponding transmission event, in Step S421.

Figure 16:
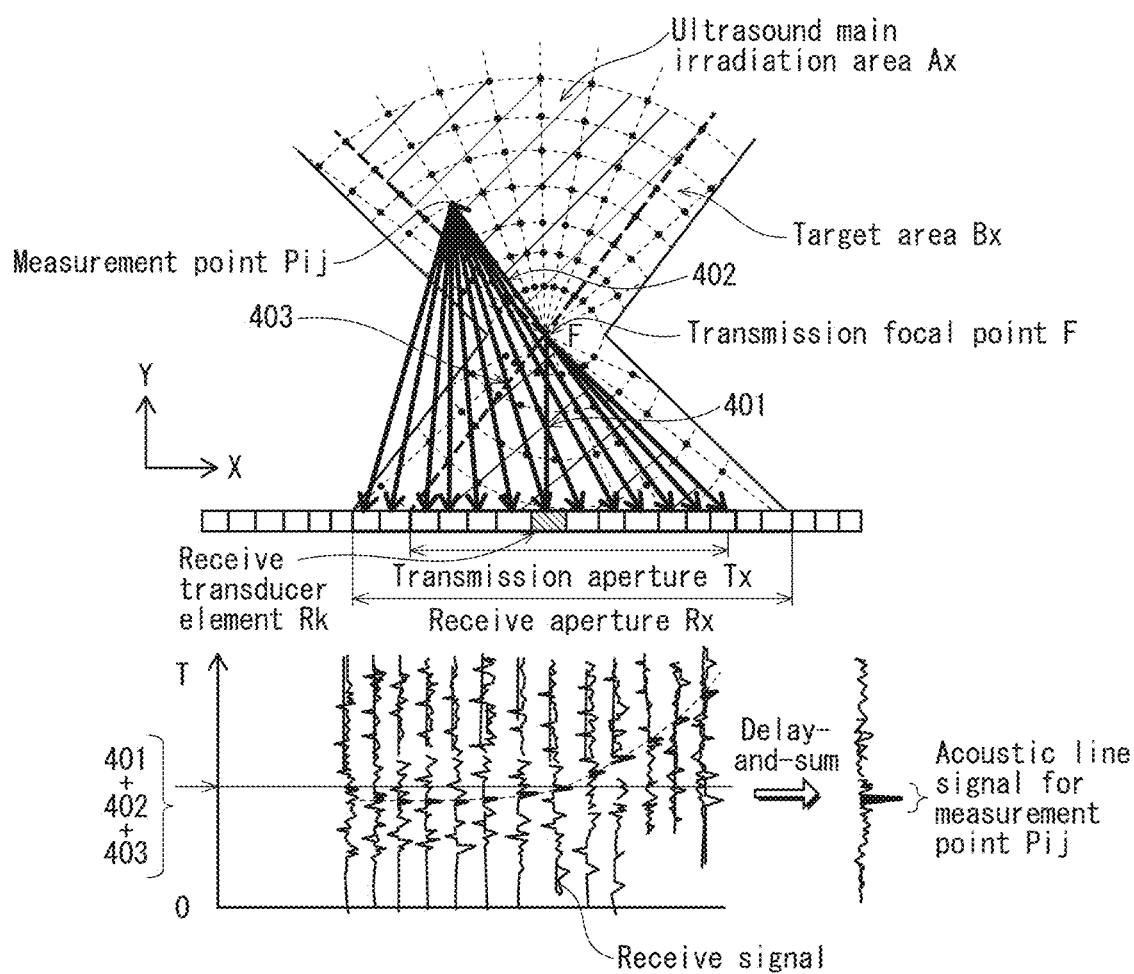
FIG. 16 is a schematic for explaining the operations of the receive beam former pertaining to modification 1 for generating an acoustic line signal for a measurement point Pij.

Subsequently, coordinate values i and j indicating a position of a measurement point Pij that is included in the target area Bx for the processing-target transmission event are initialized (set to the respective minimum possible values in the target area Bx set in Step S210) (Steps S422 and S423). Subsequently, an acoustic line signal is generated for the current measurement point Pij (Step S424). FIG. 16 is a schematic for explaining the operations of the receive beam former pertaining to modification 1 for generating the acoustic line signal for the current measurement point Pij. FIG. 16 differs from FIG. 13 referred to in embodiment 1 in terms of the positional relationship between the transmission aperture Tx and the receive aperture Rx. The processing in Step S424 is similar to that in Step S224 of FIG. 11 (i.e., Steps S2241 through S2251 in FIG. 12).

An acoustic line signal is generated for each measurement point Pij (each illustrated in FIG. 16 as a black dot) that is included in the target area Bx by repeating Step S424 while incrementing the coordinate values i and j. Subsequently, a determination is performed of whether or not an acoustic line signal has been generated for one or more of the measurement points Pij included in the target area Bx (Steps S425, S427). When an acoustic line signal has not yet been generated for every measurement point Pij within the target area Bx, the coordinate values i and j are incremented (Steps S426 and S428), yielding an acoustic line signal for another measurement point Pij (Step S424). Meanwhile, when an acoustic line signal has already been generated for every measurement point Pij within the target area Bx, processing proceeds to Step S230. At this point, an acoustic line signal has already been generated for each measurement point Pij that is included in the target area Bx for the processing-target transmission event, and the acoustic line signals have been output to and stored to the data storage 107.

<Effects>

The ultrasound diagnostic device pertaining to modification 1, which has been described up to this point, achieves the effects described in embodiment 1, excluding the effect related to setting a measurement point-dependent receive aperture. In place of the effect related to setting a measurement point-dependent receive aperture, the ultrasound diagnostic device pertaining to modification 1 achieves the following effect. In modification 1, for each transmission event, the receive aperture Rx is set by selecting receive transducer elements forming a transducer element array whose center position corresponds to the center position of the transducer element array composing the transmission aperture Tx for the transmission event. Due to this, the position of the central axis Rxo of the receive aperture Rx for a given transmission event corresponds to the position of the central axis Txo of the transmission aperture Tx for the same transmission event. Further, when transmission events are repetitively performed, the transmission aperture Tx shifts in the transducer element array direction each time, and the receive aperture Rx also shifts in the transducer element array direction in synchronization with the transmission aperture Tx. Thus, a different receive aperture is used to perform delay-and-sum for each transmission event. Accordingly, receive processing with respect to multiple transmission events can be performed by using a group of receive apertures covering a vast measurement area and each differing in terms of time. Thus, uniform spatial resolution is achieved over a vast measurement area.

Embodiment 2

The ultrasound diagnostic apparatus 100 includes the delay-and-sum processor 1041, which generates sub-frame acoustic line signals, and the synthesizer 1140, which combines the sub-frame acoustic signals to generate a frame acoustic line signal. Here, it should be noted that in embodiment 1, no distinction is made between measurement points inside the ultrasound main irradiation area Ax and measurement points outside the ultrasound main irradiation area Ax in the generation of sub-frame acoustic line signals. However, acoustic line signals generated from measurement points outside the ultrasound main irradiation area Ax, when compared with acoustic line signals generated from measurement points inside the ultrasound main irradiation area Ax, have lower spatial resolution and lower signal S/N ratio. This is since, as already described above, amplitude of transmitted ultrasound decreases and phase difference of transmitted ultrasound increases outside the ultrasound main irradiation area Ax. Accordingly, if one measurement point Pij is included in target areas Bx for two transmission events (a first transmission event and a second transmission event), is inside the ultrasound main irradiation area Ax of the target area Bx for the first transmission event, and is outside the ultrasound main irradiation area Ax of the target area Bx for the second transmission event, the measurement point Pij yields an acoustic line signal having high spatial resolution and high S/N ratio for the first transmission event and an acoustic line signal having low spatial resolution and low S/N ratio for the second transmission event. Nevertheless, in the generation of the frame acoustic line signal, a sub-frame acoustic line signal corresponding to the first transmission event and a sub-frame acoustic line signal corresponding to the second transmission event are combined, while the spatial resolution and S/N ratio for the measurement point Pij is high in the sub-frame acoustic line signal corresponding to the first transmission event and is low in the sub-frame acoustic line signal corresponding to the second transmission event. However, it should be noted that in this case, ultrasound image quality for the measurement point Pij is higher when using only the sub-frame acoustic line signal for the first transmission event.

Embodiment 2 describes an ultrasound diagnostic device that differs from the ultrasound diagnostic device 100 pertaining to embodiment 1 for: (i) separately generating a sub-frame acoustic line signal corresponding to the outside of the ultrasound main irradiation area Ax and a sub-frame acoustic line signal corresponding to the inside of the ultrasound main irradiation area Ax; (ii) combining multiple sub-frame acoustic line signals corresponding to the outside of the ultrasound main irradiation area Ax with one another and combining multiple sub-frame acoustic line signals corresponding to the inside of the ultrasound main irradiation area Ax with one another; and (iii) generating a frame acoustic line signal by combining the results of such separate combining.

<Structure>

Figure 17:
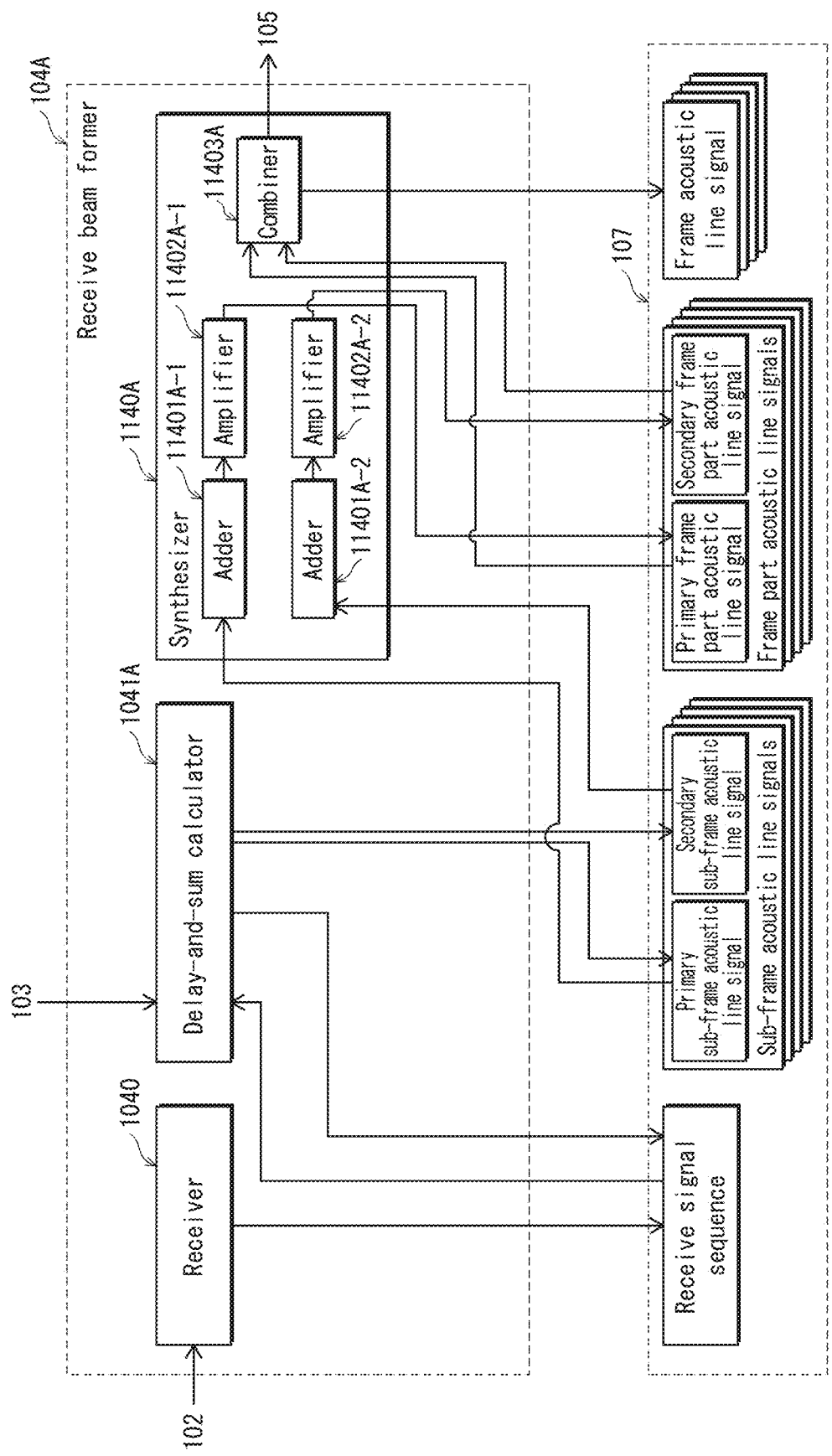
FIG. 17 is a functional block diagram illustrating the structure of a receive beam former 104A of an ultrasound diagnostic device pertaining to embodiment 2.

The following describes the ultrasound diagnostic device pertaining to embodiment 2, with reference to the accompanying drawings. FIG. 17 is a functional block diagram illustrating the structure of a receive beam former 104A of the ultrasound diagnostic device pertaining to embodiment 2. The receive beam former 104A pertaining to embodiment 2 includes a delay-and-sum calculator 1041A. For each transmission event, the delay-and-sum calculator 1041A sets a target area composed of two partial areas of differing type, and further, generates a sub-frame acoustic line signal for each partial area. In addition, the receive beam former 104A pertaining to embodiment 2 includes a synthesizer 1140A. The synthesizer 1140A combines sub-frame acoustic lines generated from partial areas of the same type to generate a frame part acoustic line signal for each type of partial area. Further, the synthesizer 1140A generates a frame acoustic line signal by combining the frame part acoustic line signals of the two partial area types. Other than the delay-and-sum calculator 1041A and the synthesizer 1140A, the components of the ultrasound diagnostic device pertaining to embodiment 2 have the same structures and configurations as the corresponding components in the ultrasound diagnostic device 100 described in embodiment 1. Thus, description of such similar components is not provided in the following.

(1) Delay-and-Sum Calculator 1041A

The delay-and-sum calculator 1041A includes a target area setter that, for each transmission event, sets a target area Bx based on the information indicating the position of the transmission aperture Tx for the transmission event, which is acquired from the transmission beam former 103.

Figure 18:
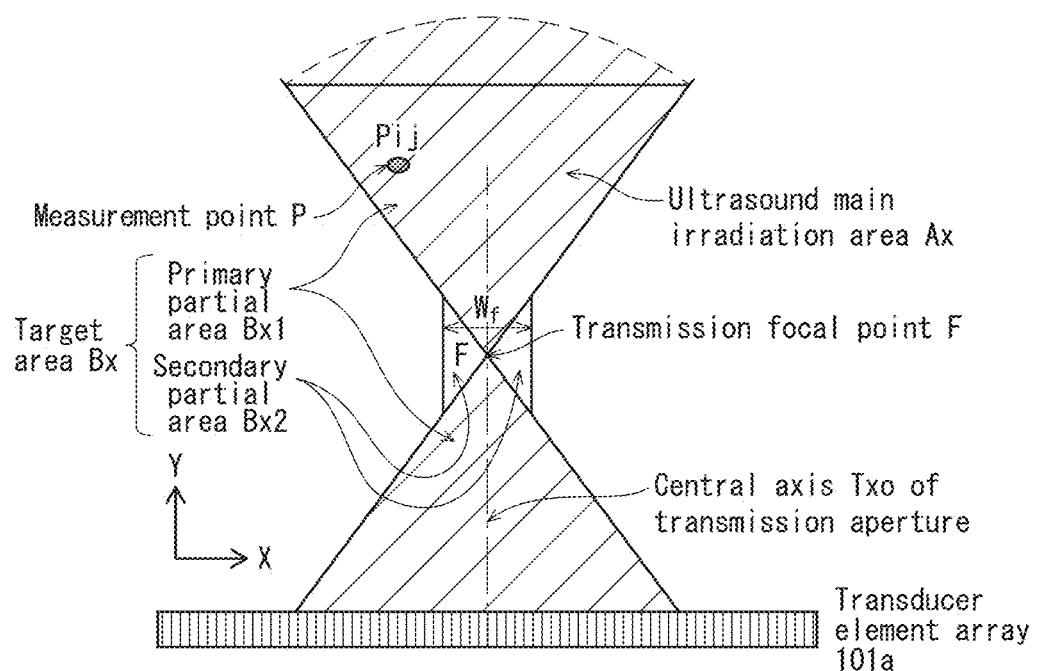
FIG. 18 is a schematic illustrating a target area Bx pertaining to embodiment 2.

FIG. 18 is a schematic illustrating one target area Bx. As illustrated in FIG. 18, the target area Bx includes two partial areas. One is a primary partial area Bx1, which corresponds to the inside of the ultrasound main irradiation area Ax. The other is a secondary partial area Bx2, which is the area of the target area Bx that is outside the ultrasound main irradiation area Ax. The secondary partial area Bx2 is adjacent to at least one side of the primary partial area Bx1 in the transducer element array direction. The target area Bx, as a whole, is set so that the minimum width Wf thereof in the transducer element array direction is equal to or greater than the shift amount Mp. This is similar to embodiment 1. Meanwhile, in the present embodiment, each target area Bx is a combination of the two types of partial areas described above, i.e., a primary partial area Bx1 and a secondary partial area Bx2. The following describes the relationship between the primary partial area Bx1 and the secondary partial area Bx2. The secondary partial area Bx2 is a combination of two triangular areas both having the transmission focal point F as one vertex thereof. The width of the secondary partial area Bx2 in the transducer element array direction is set so that, at a depth where the width of the primary partial area Bx1 is smaller than the minimum width Wf, the sum of the width of the secondary partial area Bx2 and the width of the primary partial area Bx1 equals the minimum width Wf. For example, when the shift amount Mp is equal to eight times the width of a single transducer element, the minimum width Wf may be equal to or greater than ten times the width of a single transducer element. Further, it is preferable that two secondary partial areas Bx2 respectively corresponding to two consecutive transmission events (i.e., two secondary partial areas Bx2 differing in position by the shift amount Mp) overlap one another by at least 50%. This configuration is preferable since, increasing the amount of overlap between two secondary partial areas Bx2 respectively corresponding to two consecutive transmission events increases the number of measurement points having overlap counts of at least two, and thus, ultrasound image quality increases at areas corresponding to such secondary partial areas Bx2. When set in such a manner, the target area Bx includes both measurement points covering substantially the entire ultrasound main irradiation area Ax and measurement points located in the proximity of the ultrasound main irradiation area Ax, which achieves efficient use of transmitted ultrasound.

For each of the measurement points Pij included in the target area Bx set for a given transmission event, the delay-and-sum calculator 1041A performs delay-and-sum processing with respect to receive signal sequences for the measurement point Pij, each of which is received by one of the receive transducer elements Rk. Thus, the delay-and-sum calculator 1041A calculates an acoustic line signal for each measurement point Pij included in the target area Bx, and generates a sub-frame acoustic line signal.

Here, it should be noted that for each transmission event, the delay-and-sum calculator 1041A pertaining to embodiment 2 generates a primary sub-frame acoustic line signal covering ones of the measurement points Pij included in the primary partial area Bx1 and a secondary sub-frame acoustic line signal covering ones of the measurement points Pij included in the secondary partial area Bx2. Further, the delay-and-sum calculator 1041A outputs the primary sub-frame acoustic line signal and the secondary sub-frame acoustic line signal to be stored in the data storage 107.

(2) Synthesizer 1140A

For each transmission event, the synthesizer 1140A generates one signal (introduced in the following as a primary frame part acoustic line signal) from primary sub-frame acoustic line signals corresponding to multiple transmission events, and one signal (introduced in the following as a secondary frame part acoustic line signal) from secondary sub-frame acoustic line signals corresponding to multiple transmission events. The synthesizer 1140A includes two adders (an adder 11401A-1 and an adder 11401A-2), two amplifiers (an amplifier 11402A-1 and an amplifier 11402A-2), and a combiner 11403A.

Each of the adders 11401A-1 and 11401A-2, when a series of sub-frame acoustic line signals of the corresponding type (i.e., primary sub-frame acoustic line signals for the adder 11401A-1, and secondary sub-frame acoustic line signals for the adder 11401A-2) necessary for generating one frame acoustic line signal have been generated, reads out the sub-frame acoustic line signals of the corresponding type from the data storage 107. Further, each of the adders 11401A-1 and 11401A-2 combines the sub-frame acoustic line signals of the corresponding type according to the positions of the measurement points Pij from which the acoustic line signals included in the sub-frame acoustic line signals of the corresponding type are acquired. In the present embodiment, the adder 11401A-1 generates a primary combined acoustic line signal by combining multiple primary sub-frame acoustic line signals, and the adder 11401A-2 generates a secondary combined acoustic line signal by combining multiple secondary sub-frame acoustic line signals. Thus, in the present embodiment, the term combined acoustic line signal refers to either the primary combined acoustic line signal or the secondary combined acoustic line signal. Further, note that that even if both the primary sub-frame acoustic line signal and the secondary sub-frame acoustic line signal include signals for a same measurement point Pij, the combining of such signals for the same measurement point is not performed.

Figure 19A:
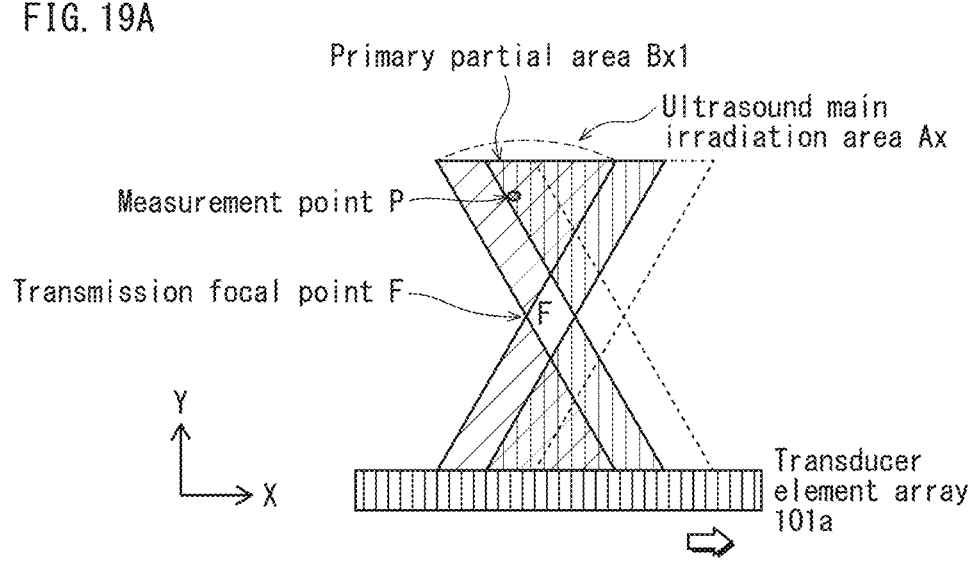
FIG. 19A is a schematic illustrating processing pertaining to embodiment 2 of generating a primary combined acoustic line signal by combining primary sub-frame acoustic line signals.
Figure 19B:
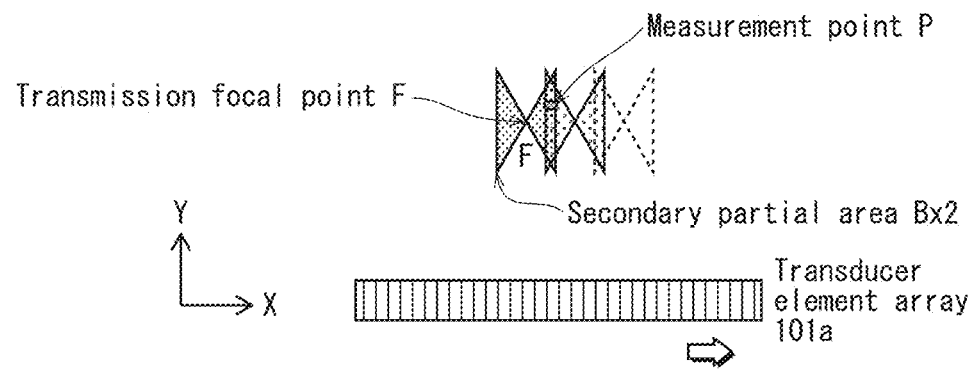
FIG. 19B is a schematic illustrating processing pertaining to embodiment 2 of generating a secondary combined acoustic line signal by combining secondary sub-frame acoustic line signals.
Figure 19C:
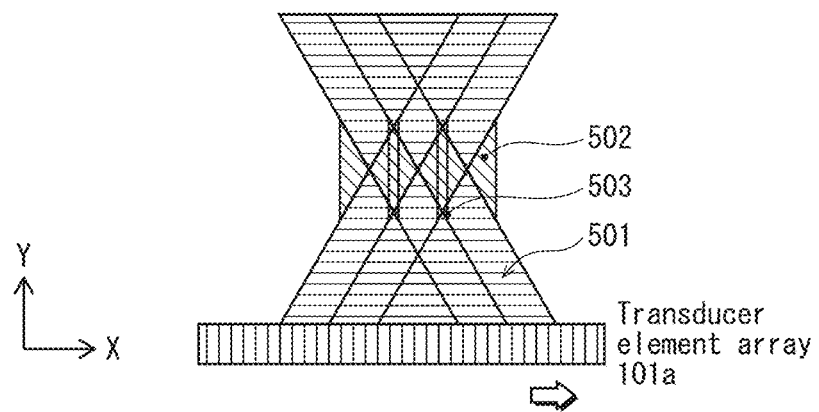
FIG. 19C is a schematic illustrating processing pertaining to embodiment 2 of generating a frame acoustic line signal.

FIGS. 19A through 19C are schematics illustrating processing of generating a frame acoustic line signal from the primary and secondary sub-frame acoustic line signals. FIG. 19A illustrates the processing of combining a plurality of primary sub-frame acoustic line signals according to the positions of measurement points P to generate a primary combined acoustic line signal covering all primary partial areas Bx1. Meanwhile, FIG. 19B illustrates the processing of combining a plurality of secondary sub-frame acoustic line signals according to the positions of measurement points P to generate a secondary combined acoustic line signal covering all secondary partial areas Bx2.

The amplifier 11402A-1 performs amplification processing of amplifying the primary combined acoustic line signal by using amplification factors each of which is determined based on the number of acoustic line signals, included in the primary sub-frame acoustic line signals, combined to yield the primary combined acoustic line signal. Similarly, the amplifier 11402A-2 performs amplification processing of multiplying the secondary combined acoustic line signal by using amplification factors each of which is determined based on the number of acoustic line signals, included in the secondary sub-frame acoustic line signals, combined to generate the secondary combined acoustic line signal. Further, each of the amplifiers 11402A-1 and 11402A-2 may also multiply the corresponding combined acoustic line signal by amplification factors varying in the transducer element array direction that are calculated based on overlap counts, when overlap counts vary in the transducer element array direction. This moderates a difference between values of the corresponding combined acoustic line signal deriving from the difference in overlap counts in the transducer element array direction, and thus, the values of the corresponding combined acoustic line signal after the amplification are averaged out in the transducer element array direction. Through such amplification, the primary combined acoustic line signal becomes a primary frame part acoustic line signal, and the secondary combined acoustic line signal becomes a secondary frame part acoustic line signal. The amplifier 11402A-1 outputs the primary frame part acoustic line signal to be stored in the data storage 107, and the amplifier 11402A-2 outputs the secondary frame part acoustic line signal to be stored in the data storage 107.

The primary frame part acoustic line signal and the secondary frame part acoustic line signal are then combined by the combiner 11403A to generate a frame acoustic line signal.

FIG. 19C is a schematic illustrating processing of generating a frame acoustic line signal from the primary frame part acoustic line signal and the secondary frame part acoustic line signal. First in this processing, for each measurement point P, a determination is made of a region to which the measurement point P belongs. Specifically, each measurement point P belongs to one of the three types of regions described in the following. A measurement point P is determined as belonging to region 501 when the measurement point P is included in a primary partial area Bx1 for at least one transmission event and is not included in a secondary partial area Bx2 for any transmission event. A measurement point P is determined as belonging to region 502 when the measurement point P is included in a secondary partial area Bx2 for at least one transmission event and is not included in a primary partial area Bx1 for any transmission event. A measurement point P is determined as belonging to region 503 when the measurement point P is included in a primary partial area Bx1 for at least one transmission event and is also included in a secondary partial area Bx2 for at least one transmission event. Further, for a measurement point P belonging to region 501, a value of a corresponding acoustic line signal in the primary frame part acoustic line signal is included in the frame acoustic line signal. For a measurement point P belonging to region 502, a value of a corresponding acoustic line signal in the secondary frame part acoustic line signal is included in the frame acoustic line signal. For a measurement point P belonging to region 503, a value of a corresponding acoustic line signal included in the primary frame part acoustic line signal and/or a value of a corresponding acoustic line signal in the secondary frame part acoustic line signal is/are used for calculating a value of an acoustic line signal included in the frame acoustic line signal corresponding to the measurement point P. However, note that in the present embodiment, for a measurement point P belonging to region 503, only a value of a corresponding acoustic line signal in the primary frame part acoustic line signal is included in the frame acoustic line signal. Such a configuration achieves, for each measurement point P belonging to region 503, calculating a value of a corresponding acoustic line signal included in the frame acoustic line signal by using only acoustic line signal values having been acquired when the measurement point P was inside ultrasound main irradiation areas Ax. Thus, this configuration achieves high spatial resolution and high signal S/N ratio for measurement points belonging to region 503, as well as for measurement points belonging to region 501.

Nevertheless, for a measurement point P belonging to region 503, both a value (first value) of a corresponding acoustic line signal included in the primary frame part acoustic line signal and a value (second value) of a corresponding acoustic line signal in the secondary frame part acoustic line signal may be used for calculating a value (third value) of a corresponding acoustic line signal included in the frame acoustic line signal. In this case, the third value may be acquired by calculating an arithmetic mean, a geometric mean, or a linear combination of the first and second values. Calculating the third value by using both the first and second values prevents the risk of a considerable gap occurring in the frame acoustic line signal, between values corresponding to measurement points at both sides of a boundary between regions 501 and 503. This ensures sufficient image quality improvement at such a boundary.

The frame acoustic line signal so generated is output by the combiner 11403A to be stored in the data storage 107.

<Operations>

Figure 20:
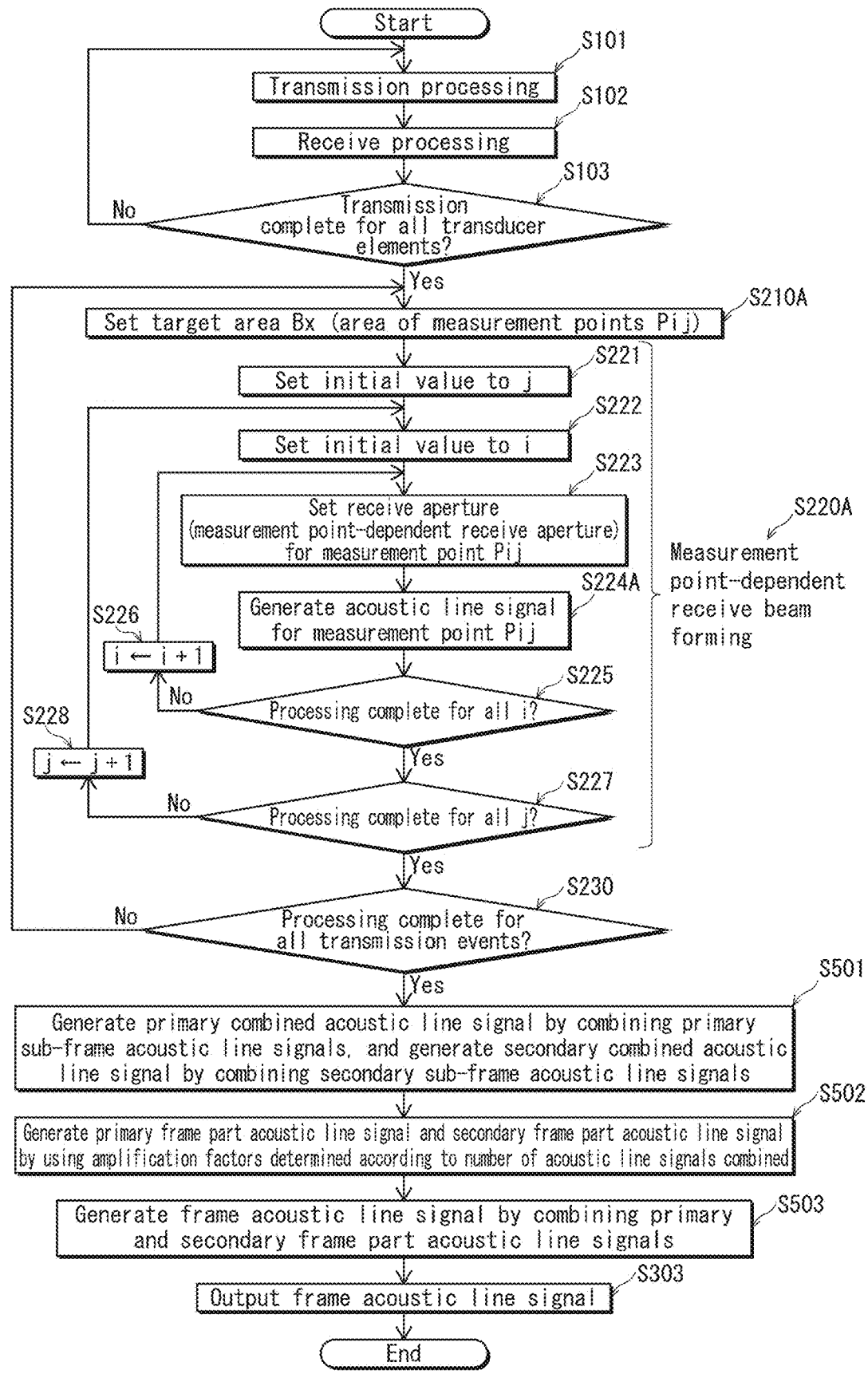
FIG. 20 is a flowchart illustrating beam forming by the receive beam former 104A pertaining to embodiment 2.

FIG. 20 is a flowchart illustrating beam forming by the receive beam former 104A. The flowchart of FIG. 20 differs from the flowchart of FIG. 11 for: (i) including Step S210A in place of Step S210 (target area setting); (ii) including Step S220A, which includes Step S224A, in place of Step S220 (receive beam focusing), which includes Step S224 (acoustic line signal generating); (iii) including Step S501 in place of Step S301 (frame acoustic line signal generating); and (iv) including Step S502 in place of Step S302 (frame acoustic line signal amplification), and for further including Step S503 not included in FIG. 11. Meanwhile, the processing in steps other than such steps in the flowchart in FIG. 20 is similar to the processing in the corresponding steps in the flowchart in FIG. 11. Thus, description of such similar processing is not provided in the following.

In Step S210A, the target area setter of the delay-and-sum calculator 1041A sets a target area Bx for the processing-target transmission event. In specific, the target area setter, based on the information indicating the position of the transmission aperture Tx for the transmission event, sets a primary partial area Bx1 and a secondary partial area Bx1.

Subsequently, processing proceeds to measurement-point dependent beam forming in Step S220A (including Steps S221 through S223, Step S224A, and Steps S225 through S228). Since the processing in Step S220A, other than the processing in Step S224A, is similar to the corresponding processing in Step S220, only the processing in Step S224A is described in the following.

In Step S224A, the delay-and-sum calculator 1041A generates an acoustic line signal for the processing-target measurement point Pij, and outputs the acoustic line signal so generated to the data storage 107. Here, when the measurement point Pij is included in the primary partial area Bx1, the delay-and-sum calculator 1041A includes the acoustic line signal for the measurement point Pij in the primary sub-frame acoustic line signal, which is output to the data storage 107. Meanwhile, when the measurement point Pij is included in the secondary partial area Bx2, the delay-and-sum calculator 1041A includes the acoustic line signal for the measurement point Pij in the secondary sub-frame acoustic line signal, which is output to the data storage 107. Through the processing in Step S220A being repeated, the primary sub-frame acoustic line signal corresponding to the primary partial area Bx1 and the secondary sub-frame acoustic line signal corresponding to the secondary partial area Bx2 are generated.

Subsequently, a determination is performed of whether or not a set of a primary sub-frame acoustic line signal and a secondary sub-frame acoustic line signal has been generated for each transmission event having been performed (Step S230). When the set of sub-frame acoustic signals has not yet been generated for one or more transmission events, processing returns to Step S210A, where the target area setter sets a target area Bx (i.e., a primary partial area Bx1 and a secondary partial area Bx2) for the subsequent transmission event based on information indicating the transmission aperture Tx for the subsequent transmission event, which is acquired from the transmission beam former 103 (Step S210A). Meanwhile, when the set of sub-frame acoustic line signals has been generated for all transmission events, processing proceeds to Step S501.

Subsequently, a primary combined acoustic line signal is generated by combining primary sub-frame acoustic line signals according to the positions of the measurement points Pij, and a secondary combined acoustic line signal is generated by combining secondary sub-frame acoustic line signals according to the positions of the measurement points Pij (Step S501). Then, the primary combined acoustic line signal and the secondary combined acoustic line signal are each multiplied by amplification factors that are in accordance with the number of signals combined to generate the signal, whereby a primary frame part acoustic line signal and a secondary frame part acoustic line signal are respectively generated (Step S502). Further, the primary frame part acoustic line signal and the secondary frame part acoustic line signal are combined, to generate a frame acoustic line signal (Step S503). Subsequently, the frame acoustic line signal so generated is output to the ultrasound image generator 105 and the data storage 107 (Step S303). This completes the processing.

<Effects>

As described up to this point, the ultrasound diagnostic device pertaining to embodiment 2, similar to the ultrasound diagnostic apparatus 100 pertaining to embodiment 1, prevents the occurrence of defective areas even when the shift amount is provided with a great value. Thus, the ultrasound diagnostic device pertaining to embodiment 2 prevents image quality reduction while achieving high frame rate. FIG. 26A illustrates one example of an ultrasound image generated by the ultrasound diagnostic device pertaining to embodiment 2. The ultrasound image in FIG. 26A does not have defective areas (i.e., areas where data is missing). Thus, vertical stripes at the transmission focal depth are less prominent in the ultrasound image in FIG. 26A than in the ultrasound image in FIG. 26D.

In addition, the ultrasound diagnostic device pertaining to embodiment 2 separately performs (i) the combining of primary partial areas Bx1 and (ii) the combining of secondary partial areas Bx2, and then combines the result of the combining in (i) and the result of the combining in (ii). Further, the ultrasound diagnostic device pertaining to embodiment 2, for a measurement point Pij for which an acoustic line signal in the frame acoustic line signal can be generated by combining signals corresponding thereto that are included in primary sub-frame acoustic line signals, does not use signals corresponding thereto that are included in secondary sub-frame acoustic line signals for generating the frame acoustic line signal. The frame acoustic line signal, due to including an acoustic line signal based on only the primary sub-frame acoustic line signals for such a measurement point P, has improved spatial resolution and signal S/N ratio where corresponding to such a measurement point P.

<<Modification 2>>

The delay-and-sum calculator 1041A of the ultrasound diagnostic device pertaining to embodiment 2 calculates a transmission time for each measurement point included in primary partial areas Bx1 and a transmission time for each measurement point included in secondary partial areas Bx2 in the same manner.

Meanwhile, modification 2 describes a delay-and-sum calculator including a transmission time calculator that changes the method used for the calculation of transmission times depending upon whether a measurement point Pij is included in a primary partial area Bx1 or a secondary partial area Bx2.

<Calculation of Transmission Times>

Figure 21A:
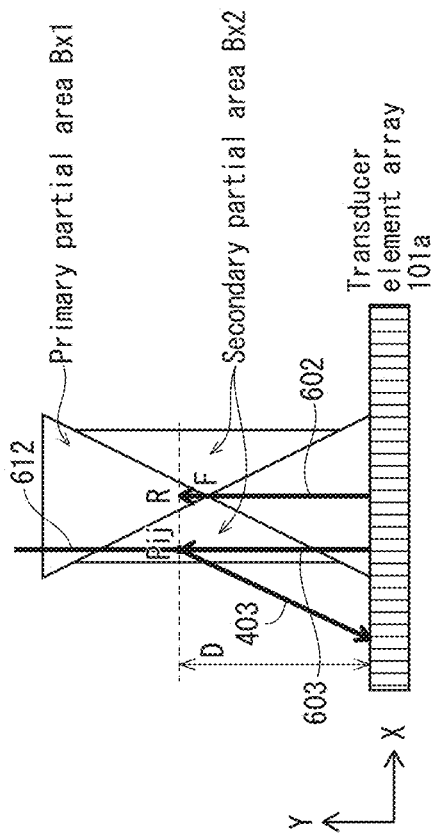
FIG. 21A is a schematic pertaining to modification 2, illustrating one propagation path of ultrasound.
Figure 21B:
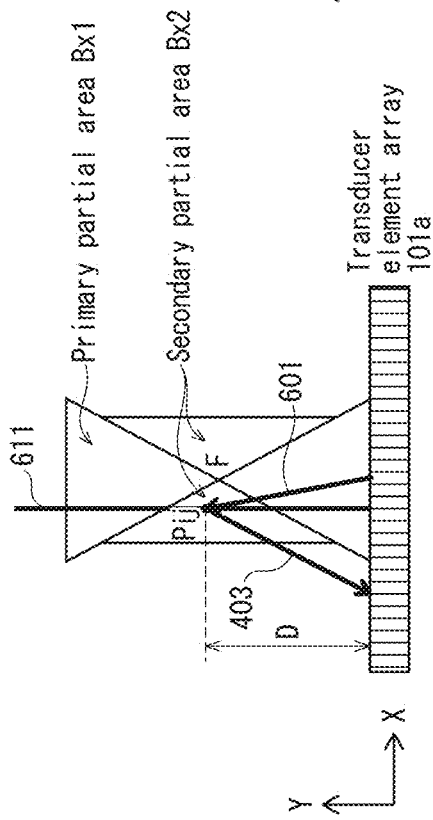
FIG. 21B is a schematic pertaining to modification 2, illustrating another propagation path of ultrasound, FIG. 21C pertains to modification 2 and illustrates one example of a relationship between depths D of measurement points Pij and transmission times for the measurement points, and FIG. 21D pertains to modification 2 and illustrates another example of the relationship between depths D of measurement points Pij and transmission times for the measurement points.

The following describes the method used in the present modification for the calculation of transmission times, with reference to FIGS. 21A through 21D. Each of FIGS. 21A and 21B is a schematic illustrating propagation paths of ultrasound according to the present modification. In the present modification, the calculation of a transmission time for each measurement point Pij included in a primary partial area Bx1 is conducted according to the method described with reference to FIGS. 7A and 7B. That is, a transmission time for such a measurement point Pij is calculated such that (i) when the measurement point Pij is located at or deeper than the transmission focal depth, a sum of the time amount required for transmitted ultrasound to travel through path 401 and the time amount required for transmitted to travel through path 402 is used as the transmission time, and (ii) when the measurement point Pij is located shallower than the transmission focal depth, a value obtained by subtracting the time amount required for transmitted ultrasound to travel through path 402 from the time amount required for transmitted ultrasound to travel through the path 401 is used as the transmission time.

Figure 22A:
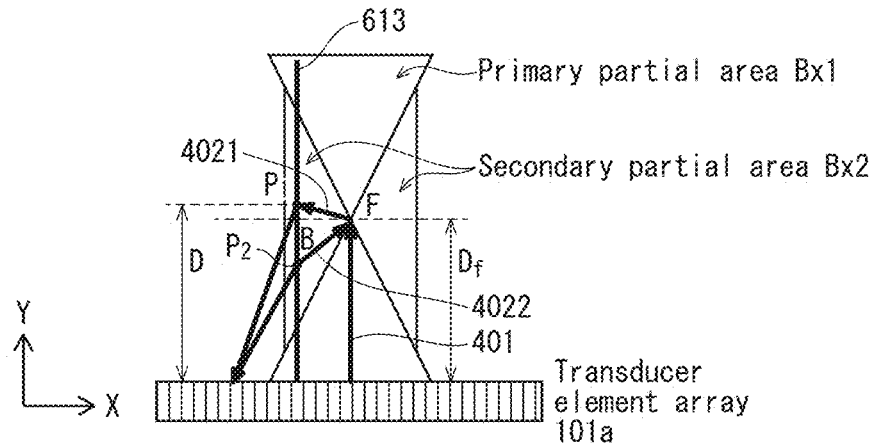
FIG. 22A is a schematic pertaining to modification 2, illustrating propagation paths of ultrasound, FIG. 22B pertains to modification 2 and illustrates one example of the relationship between depths D of measurement points Pij and transmission times for the measurement points.
Figure 22B:
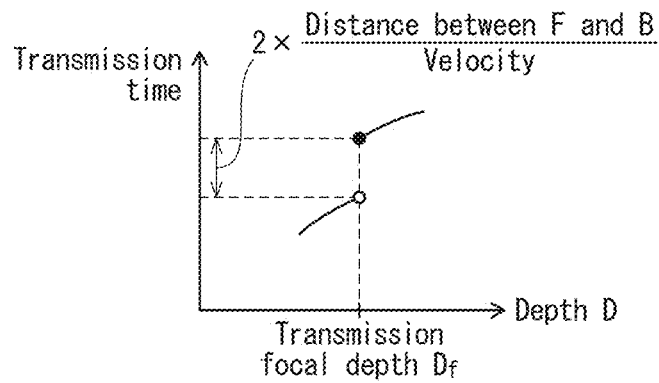
FIG. 22C shows one example of an ultrasound image in which a gap in luminance is observed at both sides of a focal depth, at areas corresponding to secondary sub-frame acoustic line signals.
Figure 22C:
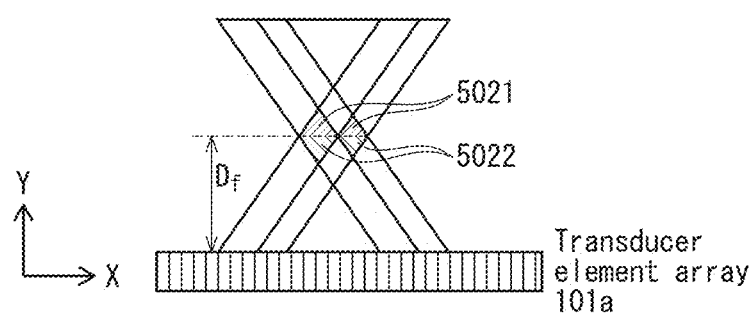

Meanwhile, in the present modification, the calculation of a transmission time for each measurement point Pij included in a secondary partial area Bx2 is conducted according to a method differing from the method described with reference to FIGS. 7A and 7B. To begin with, description is provided why the present modification differentiates the calculation method of transmission times between measurement points Pij included in primary partial areas Bx1 and measurement points Pij included in secondary partial areas Bx2, with reference to FIGS. 22A through 22C. FIG. 22A illustrates a case where the calculation method applied to measurement points included in primary partial areas Bx1 is also applied to measurement points included in secondary partial areas Bx2. FIG. 22A shows line 613 that is straight and perpendicular to the transducer element array direction along which the transducer elements 101a are disposed. Point B indicates a point along line 613 that is located at the transmission focal depth Df. In the case illustrated in FIG. 22A, for measurement point P1 located deeper than the transmission focal depth Df, a sum of the time amount required for transmitted ultrasound to travel through path 401 and the time amount required for transmitted to travel through path 4021 is used as the transmission time for measurement point $P_1$, and for measurement point $P_2$ located shallower than the transmission focal depth Df, a value obtained by subtracting the time amount required for transmitted ultrasound to travel through path 4022 from the time amount required for transmitted ultrasound to travel through path 401 is used as the transmission time for the measurement point $P_2$. Note that the transmission time for point B may be calculated according to either the calculation method applied for measurement points located deeper than the transmission focal depth Df or the calculation method applied to measurement points located shallower than the transmission focal depth Df. Here, if supposing that the points $P_1$, B, and $P_2$ are very close to one another, the distance between points B and F (i.e., the transmission focal point), the length of path 4021, and the length of path 4022 would be substantially equal. Despite this situation, applying the different calculation methods described above to points $P_1$ and $P_2$ results in the transmission times for points $P_1$ and $P_2$ differing by a time amount of 2×(distance between points B and F)/(ultrasound velocity in subject). Further, this difference changes depending upon the distance between points B and F, and in particular, the greater the distance between points B and F, the greater this difference. This difference in transmission time between points $P_1$ and $P_2$ results in a discontinuity, at the transmission focal depth Df, in the change of transmission times in the depth direction. FIG. 22B illustrates, for measurement points Pij along line 613, a relationship between the depths D of the measurement points Pij and the transmission times calculated for the measurement points Pij when applying the different calculation methods described above to points $P_1$ and $P_2$. FIG. 22B clearly shows this discontinuity, at the transmission focal depth Df, in the change of transmission times in the depth direction. Naturally, this discontinuity results in a similar discontinuity, at the transmission focal depth Df, between delay amounts to be applied to the measurement points Pij in the delay-and-sum processing. Meanwhile, FIG. 22B illustrates a case where the transmission time for point B located at focal depth Df is calculated according to the calculation method applied to measurement points located deeper than the transmission focal depth Df. However, even if the transmission time for point B were calculated according to the calculation method applied to measurement points located shallower than the transmission focal depth Df, a similar discontinuity in the change of transmission times in the depth direction would occur at the transmission focal depth Df, while a different value would be calculated as the transmission time for point B. (This case can be depicted by replacing the unfilled circle with a filled circle and replacing the filled circle with an unfilled circle in FIG. 22B.) This discontinuity, at the transmission focal depth Df, in the change of transmission times in the depth direction (and the consequent discontinuity, at the transmission focal depth Df, in the change of delay amounts in the depth direction) results in a discontinuity, at the transmission focal depth Df, of measurement point values of a secondary sub-frame acoustic line signal. This further results in, for example, noise appearing in a frame acoustic line signal along the transmission focal depth. This means that there remains room for further image quality improvement with respect to region 502. For example, as can be seen in the ultrasound image shown in FIG. 22C, a difference in luminance may be present between areas corresponding to secondary sub-frame acoustic line signals that are located at opposite sides of the transmission focal depth Df (e.g., between area 5021 and area 5022 in FIG. 22C). Eliminating such a difference in luminance would improve image quality.

Figure 21C:
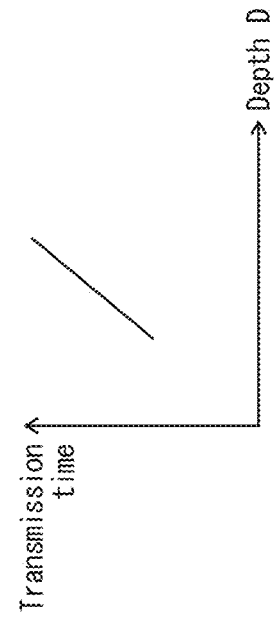

In view of this, in the present modification, transmissions time for measurement points Pij included in secondary partial areas Bx2 are calculated as described in the following. FIG. 21A illustrates one method applicable in the calculation of transmission times for measurement points Pij included in secondary partial areas Bx2. A transmission time calculated according to the method illustrated in FIG. 21A is denoted as a transmission time $T_D$ in the following. In this method, the calculation of a transmission time for a measurement point Pij included in a secondary partial area Bx2 is performed regarding that transmitted ultrasound from the transmission aperture Tx directly reaches the measurement point Pij by traveling along path 601. That is, transmission time $T_D$ is the time amount required for ultrasound transmitted from a center position of a transmission aperture Tx to arrive at a measurement point Pij by traveling through path 601. FIG. 21C corresponds to the method illustrated in FIG. 21A, and illustrates, for measurement points Pij along line 611 that is straight and perpendicular to the transducer element array direction, a relationship between depths D of the measurement points Pij and the transmission times $T_D$ calculated for the measurement points Pij.

As illustrated in FIG. 21C, transmission time $T_D$ increases monotonically as depth D increases, and thus, there is no discontinuity between the transmission times for the measurement points Pij along line 611.

Figure 21D:
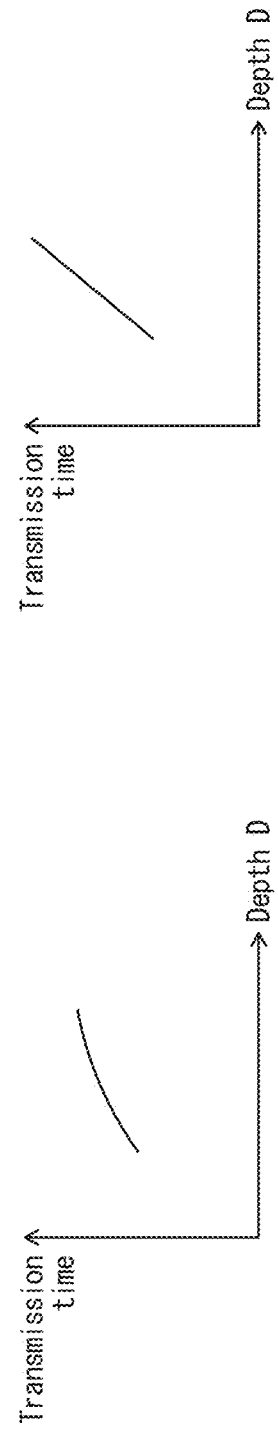

Further, FIG. 21B illustrates another method applicable in the calculation of transmission times for measurement points included in secondary partial areas Bx2. A transmission time calculated according to the method illustrated in FIG. 21B is denoted as a transmission time $T_S$ in the following. In this method, the calculation of a transmission time for a measurement point Pij included in a secondary partial area Bx2 is performed by using path 602 that is the shortest among paths connecting the transmission aperture Tx and a reference point R at the same depth as the measurement point Pij, regarding that transmitted ultrasound from the transmission aperture Tx reaches the measurement point Pij and the reference point R at the same time. That is, transmission time $T_S$ is the time amount required for ultrasound transmitted from a center position of a transmission aperture to arrive at a reference point R by traveling through path 602. Here, note that path 602 has the same length as path 603 connecting the transducer element spatially closest to the measurement point Pij to the measurement point Pij, which is the shortest among paths connecting the transmission aperture Tx and the measurement point Pij. In other words, path 602 has a length equal to the depth of the measurement point Pij. FIG. 21D corresponds to the method illustrated in FIG. 21B, and illustrates, for measurement points Pij along line 612 that is straight and perpendicular to the transducer element array direction, a relationship between depths D of the measurement points Pij and the transmission times $T_S$ calculated for the measurement points Pij. As illustrated in FIG. 21D, transmission time $T_S$ increases monotonically as depth D increases, and thus, there is no discontinuity between the transmission times for the measurement points Pij along line 613.

Further, note that transmissions time for measurement points Pij included in secondary partial areas Bx2 may be calculated according to methods other than those described above, as long as for measurement points Pij along a straight line perpendicular to the transducer element array direction, transmission time monotonically increases as depth increases. For example, a transmission time for a measurement point Pij included in a secondary partial area Bx2 may be calculated based on a path connecting any single position of a transmission aperture Tx and an any single point at the same depth as the measurement point Pij.

Calculating transmission times for measurement points Pij included in secondary partial areas Bx2 as described above achieves the following effects: (i) the effect described in embodiment 1 of preventing the occurrence of defective areas even when the shift amount is provided with a great value, and thereby preventing image quality reduction while achieving high frame rate; (ii) the effect described in embodiment 2 of preventing a decrease in spatial resolution and signal S/N ratio that would otherwise occur when using, for a measurement point Pij for which an acoustic line signal in the frame acoustic line signal can be generated by combining only signals corresponding thereto that are included in primary sub-frame acoustic line signals, signals corresponding thereto that are included in both primary sub-frame acoustic line signals and secondary sub-frame acoustic line signals for generating a frame acoustic line signal; and (iii) an effect of improving ultrasound image quality as illustrated by the example ultrasound image shown in FIG. 26B, by preventing a discontinuity in transmission time at the transmission focal depth.

<<Modification 3>>

The delay-and-sum calculator pertaining to modification 2 calculates a transmission time for a measurement point Pij included in a secondary partial area Bx2 based on a path connecting any single position of a transmission aperture Tx and any single point at the same depth as the measurement point Pij.

However, completely differentiating the calculation method of transmission times between measurement points Pij included in primary partial areas Bx1 and measurement points Pij included in secondary partial areas Bx2 results in a discontinuity in transmission times occurring at a boundary between a primary partial area Bx1 and a secondary partial area Bx2. This further results in, for example, noise appearing along a boundary between region 501 and region 502. This means that image quality improvement at the boundary between region 501 and region 502 is insufficient. FIG. 23D is a schematic showing an ultrasound image including noise at a boundary between area 5012 corresponding to primary sub-frame acoustic line signals and area 5022 corresponding to secondary sub-frame acoustic line signals.

In view of this, a delay-and-sum calculator pertaining to modification 3 calculates transmission times for measurement points Pij included in secondary partial areas Bx2 so that there is no discontinuity in transmission time between primary partial areas Bx1 and secondary partial areas Bx2, and transmission time increases monotonically as depth increases.

<Calculation of Transmission Times>

Figure 23A:
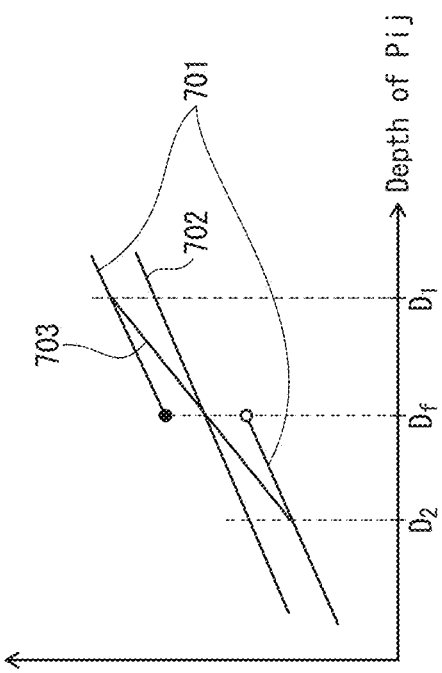
FIG. 23A is a schematic pertaining to modification 3, illustrating propagation paths of ultrasound, FIG. 23B pertains to modification 3 and illustrates one example of the relationship between depths D of measurement points Pij and transmission times for the measurement points.
Figure 23B:
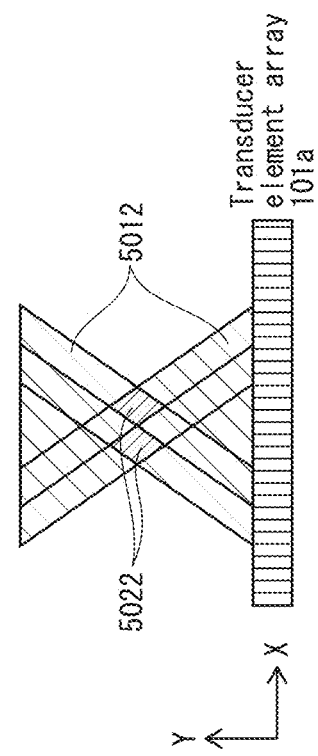
FIG. 23C illustrates one example of a relationship between variable α used in calculating transmission times and depths D of measurement points Pij.
FIG. 23D shows one example of an ultrasound image in which a gap in luminance is observed at boundaries between areas corresponding to primary sub-frame acoustic line signals and areas corresponding to secondary sub-frame acoustic line signals.
Figure 23C:
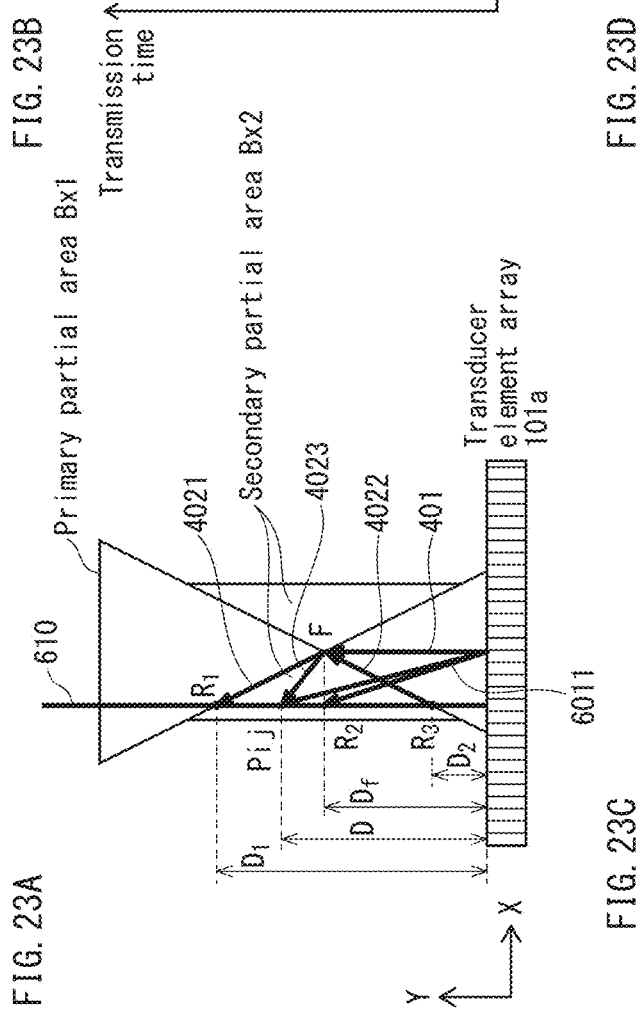
Figure 23D:
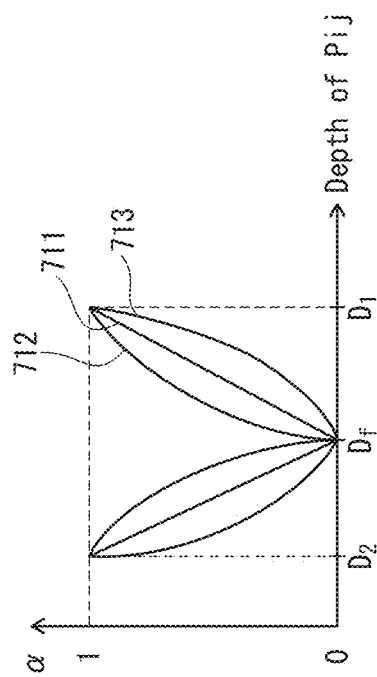

The following describes the method used in the present modification for the calculation of transmission times for measurement points Pij included in secondary partial areas Bx2, with reference to FIGS. 23A through 23D. FIG. 23A is a schematic illustrating propagation paths of ultrasound according to the present modification. FIG. 23A shows line 610 that is straight and perpendicular to the transducer element array direction. In the present modification, transmission times for measurement points $R_1$ and $R_3$ (respectively referred to in the following as boundary points $R_1$ and $R_3$), each of which is located at a boundary between a secondary partial area Bx2 and a primary partial area Bx1, are calculated according to the method applied in the calculation of transmission times for measurement points Pij included in primary partial areas Bx1. In specific, the transmission time for boundary point $R_1$ located deeper than the transmission focal depth is calculated by summing the time amount required for transmitted ultrasound to travel through path 401 and the time amount required for transmitted ultrasound to travel through path 4021. Meanwhile, the transmission time for boundary point $R_3$ located shallower than the transmission focal depth is calculated by subtracting the time amount required for transmitted ultrasound to travel through path 4022 from the time amount required for transmitted ultrasound to travel through path 401.

Meanwhile, the transmission time for measurement point $R_2$ (referred to in the following as intermediate point $R_2$), which is located along line 610, is located at the transmission focal depth Df, and is located halfway between the boundary points $R_1$ and $R_3$, is calculated according to the method illustrated in FIG. 21A. That is, the time amount required for transmitted ultrasound to travel through path 6011 (i.e., transmission time $T_D$) is regarded as the transmission time for intermediate point $R_2$.

Further, in the present modification, for each measurement point Pij located between boundary point $R_1$ and intermediate point $R_2$ and for each measurement point Pij located between boundary point $R_3$ and intermediate point $R_2$, a transmission time is calculated by using both a transmission time for the measurement point Pij that is calculated according to the method applied to measurement points included in primary partial areas Bx1 (denoted in the following as transmission time $T_R$) and a transmission time $T_D$ calculated for the measurement point Pij. Here, note that a transmission time $T_S$ calculated for the measurement point Pij may be used in place of the transmission time $T_D$ calculated for the measurement point Pij. Note that the following description is provided based on a case where the transmission time $T_D$ calculated for the measurement point Pij is used in combination with a transmission time $T_R$ calculated for the measurement point Pij. However, the following description similarly applies to when the transmission time $T_S$ calculated for the measurement point Pij is used in place of the transmission time $T_D$ calculated for the measurement point Pij.

Specifically, in calculating transmission times for measurement points Pij located between boundary point $R_1$ and intermediate point $R_2$ and measurement points Pij located between boundary point $R_3$ and intermediate point $R_2$, a transmission time for each of the measurement points Pij is calculated by combining the transmission time $T_R$ and the transmission time $T_D$ for the measurement point Pij so that the following conditions are satisfied. Condition (1): The transmission times for the measurement points Pij monotonically increase as depth D increases, without any discontinuity therebetween. Condition (2): For each boundary point ($R_1$ and $R_3$), the transmission time $T_R$ calculated for the boundary point is used as the transmission time for the boundary point. Condition (3): For intermediate point $R_2$, the transmission time $T_D$ calculated for intermediate point $R_2$ is used as the transmission time for intermediate point $R_2$. FIG. 23B is a graph illustrating, for measurement points Pij located between boundary point $R_1$ and intermediate point $R_2$ and measurement points Pij located between boundary point $R_3$ and intermediate point $R_2$, a relationship between depths D and transmission times for such measurement points Pij. In FIG. 23B, line 701 indicates transmission times $T_R$ calculated for the measurement points Pij, and line 702 indicates transmission times $T_D$ calculated for the measurement points Pij. For example, in the present modification, transmission times for measurement points Pij located between boundary point $R_1$ and intermediate point $R_2$ and measurement points Pij located between boundary point $R_3$ and intermediate point $R_2$ are calculated such that the depths D and the transmission times for such measurement points Pij satisfy the relationship indicated by line 703 in FIG. 23B, which is a straight line connecting the intercept of line 701 at depth $D_2$ and the intercept of line 701 at depth $D_1$. However, the calculation of transmission times of measurement points Pij located between the boundary point $R_1$ and the intermediate point $R_2$ and measurement points Pij located between the boundary point $R_3$ and the intermediate point $R_2$ need not be performed so that the transmission times satisfy the specific relationship indicated by line 703 in FIG. 23B, as long as the transmission times satisfies a relationship that would satisfy the following conditions based on FIG. 23B. Condition (i): A line representing the transmission times for such measurement points Pij intersects line 701 at both depths $D_1$ and $D_2$. Condition (ii): The line representing the transmission times for such measurement points Pij does not have any discontinuity between depth $D_2$ and depth $D_1$. Condition (iii): The line representing the transmission times for such measurement points Pij monotonically increases (rises to the right) from depth $D_2$ to depth $D_1$. Note that in FIGS. 23A through 23C, depth $D_1$ is depth D for boundary point $R_1$, and depth $D_2$ is depth D for boundary point $R_3$.

For example, transmission times of such measurement points Pij may be calculated by using linear combination. When using linear combination, a transmission time for each of such measurement points (denoted in the following as transmission time $T_M$) satisfies the following equation.

$$T_M = \alpha T_R + (1-\alpha) T_D$$

Here, α satisfies the two following conditions. Condition (4): α=0 when D=$D_f$, where $D_f$ denotes the depth D for intermediate point $R_2$ in FIGS. 23A through 23C. Condition (5) α=1 when D=$D_1$ or D=$D_2$. For example, when supposing that α is proportional to |D–$D_f$|, a can be defined by the following equation.

$$\alpha = |D - D_f| / (D_1 - D_f)$$

When α is defined by this equation, the relation between α and the depths of the measurement points Pij located between the boundary points $R_1$ and $R_3$ and the intermediate point $R_2$ can be depicted by a combination of two straight lines 711, one between $D_2$ and $D_f$ and the other between $D_f$ and $D_1$, in FIG. 23C. Note that α need not be defined by the equation above, and α may for example take values representable by curves 712 and curves 713 in FIG. 23C, as long as transmission time $T_M$ satisfies Conditions (1) through (5) discussed above.

In addition, note that transmission time $T_M$ need not be calculated by using linear combination as described above, and may be calculated by other methods as long as transmission time $T_M$ satisfies Conditions (1) through (3) discussed above. For example, transmission time $T_M$ may be defined by the following equation.

$$T_M = T_R^\alpha \times T_D^{(1-\alpha)}$$

Needless to say, substituting $T_S$ for $T_D$ in this equation is also possible. Further, in any equation provided in the present modification, any transmission time that satisfies the condition provided in modification 2 that transmission times for measurement points Pij along a straight line perpendicular to the transducer element array direction monotonically increase as depth increases, without any discontinuity therebetween, may be substituted for transmission time $T_D$. One example of such a transmission time is a transmission time calculated based on any path connecting one position of the transmission aperture Tx to one point at the same depth as the measurement point Pij.

Transmission times $T_M$ as described above monotonically increase as depth increases, without any discontinuity. As a result, the change in values of acoustic line signals for measurement points Pij in the depth direction becomes smooth, without any discontinuity. FIG. 26B illustrates one example of an ultrasound image generated by employing the calculation method of transmission times pertaining to the present modification. The present modification, as well as achieving the effects of modification 2, achieves further image quality improvement at the transmission focal depth and at boundaries between primary partial areas Bx1 and secondary partial areas Bx2, by ensuring that the change in transmission time in the depth direction is continuous.

<<Modification 4>>

As described above, the target area setter of the delay-and-sum calculator 1041A pertaining to embodiment 2 sets, for each transmission event, a target area Bx including a primary partial area Bx1 and a secondary partial area Bx2. Further, in embodiment 2, the primary partial area Bx1 and the secondary partial area Bx2 do not overlap each other.

Meanwhile, in the present modification, a target area Bx for each transmission event includes a primary partial area Bx1 and a secondary partial area Bx2, and the primary partial area Bx1 and the secondary partial area Bx2 overlap one another.

<Setting of Target Area Bx>

The following describes how a target area Bx is set in the present modification, and how a primary frame part acoustic line signal and a secondary frame part acoustic line signal are combined in the present modification.

Figure 24A:
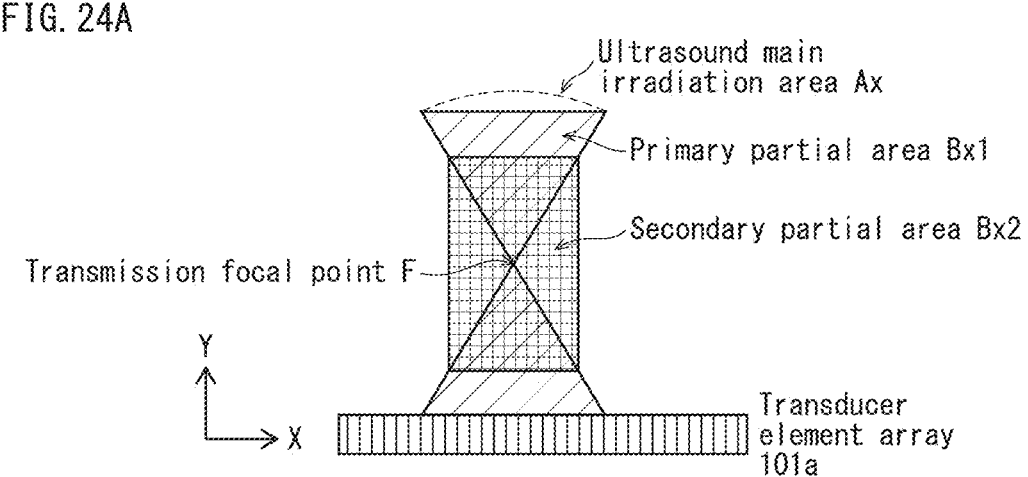
FIG. 24A is a schematic illustrating a target area Bx pertaining to modification 4.

FIG. 24A is a schematic illustrating a target area Bx pertaining to the present modification. The present modification is similar to embodiment 2 in that the primary partial area Bx1 corresponds to the inside of the ultrasound main irradiation area Ax. Further, the present modification is similar to embodiment 2 in that the secondary partial area Bx2 is set so that the minimum Wf of the overall width of the target area Bx is no smaller than the shift amount Mp. Meanwhile, the present modification differs from embodiment 2 in that the secondary partial area Bx2 has a rectangular shape and partially overlaps the primary partial area Bx1. That is, the secondary partial area Bx2 pertaining to the present modification is a combination of the secondary partial area Bx2 pertaining to embodiment 2 and a part of the primary partial area Bx1 pertaining to embodiment 2.

Similar to embodiment 2, for each of the measurement points Pij included in the target area Bx set for a given transmission event, the delay-and-sum calculator 1041A performs delay-and-sum processing with respect to receive signal sequences for the measurement point Pij, each of which is received by one of the receive transducer elements Rk. Thus, the delay-and-sum calculator 1041A calculates an acoustic line signal for each measurement point Pij included in the target area Bx, and generates a sub-frame acoustic line signal.

Further, similar to embodiment 2, sub-frame acoustic line signals of each type (primary sub-frame acoustic line signals and secondary sub-frame acoustic line signals) are combined according to the positions of the measurement points Pij from which the acoustic line signals included in the sub-frame acoustic line signals are acquired. Further, similar to embodiment 2, amplification processing of amplifying the primary combined acoustic line signal by using amplification factors each determined based on the number of acoustic line signals, included in primary sub-frame acoustic line signals, combined to generate the primary combined acoustic line signal is performed. Similarly, amplification processing of multiplying the secondary combined acoustic line signal by using amplification factors each determined based on the number of acoustic line signals, included in secondary sub-frame acoustic line signals, combined to generate the secondary combined acoustic line signal is performed. Through such amplification, the primary combined acoustic line signal becomes a primary frame part acoustic line signal, and the secondary combined acoustic line signal becomes a secondary frame part acoustic line signal. The primary frame part acoustic line signal and the secondary frame part acoustic line signal are then combined to generate a frame acoustic line signal.

Figure 24B:
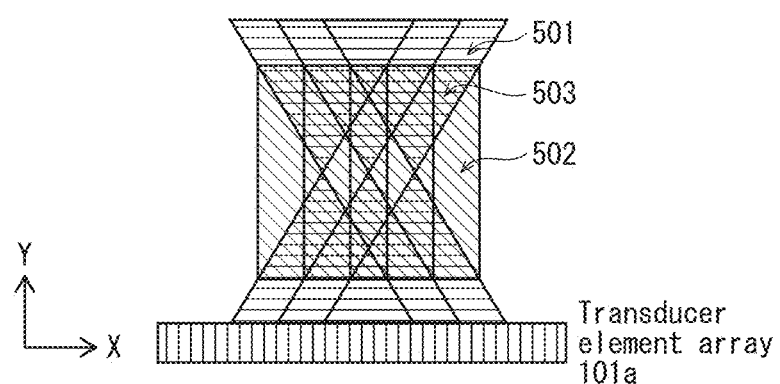
FIG. 24B is a schematic illustrating processing pertaining to modification 4 for generating a frame acoustic line signal from frame part acoustic line signals.

FIG. 24B is a schematic pertaining to the present modification illustrating processing of generating a frame acoustic line signal from the primary frame part acoustic line signal and the secondary frame part acoustic line signal. Similar to embodiment 2, for each measurement point P, a determination is made of a region (region 501, region 502, or region 503) to which the measurement point P belongs. For a measurement point P belonging to region 501 or region 503, a value of a corresponding acoustic line signal in the primary frame part acoustic line signal is included in the frame acoustic line signal. Meanwhile, for a measurement point P belonging to region 502, a value of a corresponding acoustic line signal in the secondary frame part acoustic line signal is included in the frame acoustic line signal. Here, note that in the present modification, for a measurement point P belonging to region 503, only a value of a corresponding acoustic line signal in the primary frame part acoustic line signal is included in the frame acoustic line signal. This is since, for a measurement point P located where the secondary partial area Bx2 overlaps a part of the primary partial area Bx1, using a corresponding acoustic line signal in the primary frame part acoustic line signal, which was acquired when the measurement point P was included in primary partial areas Bx1, achieves higher spatial resolution and higher signal S/N ratio compared to using a corresponding acoustic line signal in the secondary frame part acoustic line signal.

As such, secondary partial areas Bx2 pertaining to the present modification, as well as achieving the effects described in embodiment 2, has a simpler shape than secondary partial areas Bx2 pertaining to embodiment 2. Due to this, setting secondary partial areas Bx2 as described in the present modification simplifies the computation required in generating secondary sub-frame acoustic line signals and the secondary frame part acoustic line signal.

<<Other Modifications>>

(1) While description is provided in each of the embodiments and modifications that the shift amount Mp is equal to or greater than twice the width of a single transducer element in the transducer element array direction, the shift amount Mp need not have such a size. For example, the shift amount Mp may equal the width of single transducer element in the transducer element array direction. Even when making such a modification, the width of the target area Bx in the transducer element array direction may be equal to or greater than the shift amount Mp, which means that the width of the target area Bx is no smaller than the width of a single transducer element in the transducer element array direction. Meanwhile, providing the shift amount Mp with such a size leads to target areas Bx corresponding to two consecutive transmission events overlapping one another without any gap therebetween. Due to this, even when providing the shift amount Mp with such a size, the overlap count for measurement points corresponding to where the two target areas Bx overlap increases, compared to a configuration where each target area only includes the ultrasound main irradiation area Ax. Accordingly, this modification also achieves image quality improvement in areas of ultrasound images corresponding to where two target areas Bx overlap.

Figure 25A:
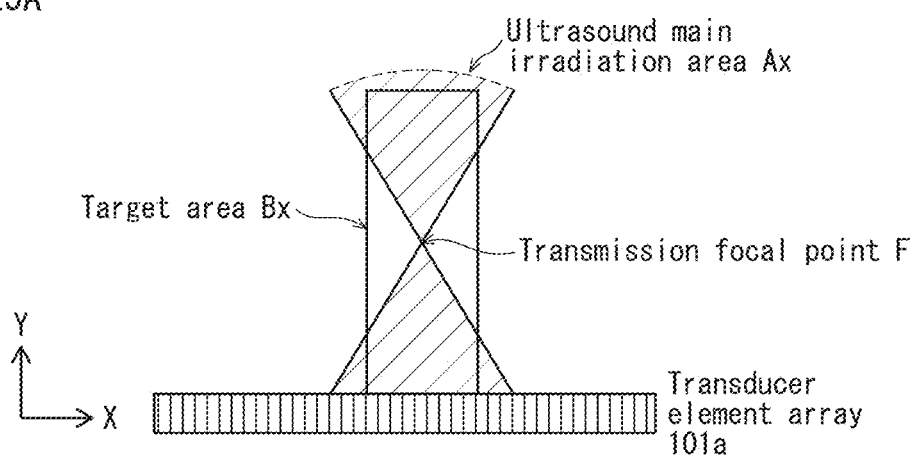
FIG. 25A is a schematic illustrating one example of a target area Bx pertaining to another modification.
Figure 25B:
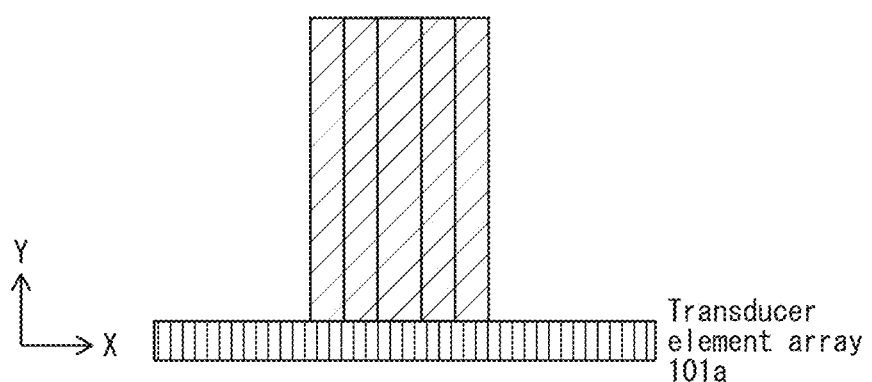
FIG. 25B is a schematic illustrating one example of a target area Bx pertaining to yet another modification.

(2) While description is provided in embodiment 1 that the target area Bx includes substantially the entirety of the hourglass-shaped ultrasound main irradiation area Ax, the target area Bx need not cover such an area. For example, the target area Bx may include a part of the ultrasound main irradiation area Ax and a part corresponding to the outside of the ultrasound main irradiation area Ax. Specifically, the target area Bx may have a rectangular shape whose width Wf in the transducer element array direction is equal to or greater than the shift amount Mp. For example, as illustrated in the schematic in FIG. 25A, when the shift amount Mp equals four times the width of a single transducer element in the transducer element array direction, the rectangular target area Bx may have a width corresponding to ten times the width of a single transducer element in the transducer element array direction. Making this modification while providing the target area Bx with a width in the transducer element array direction smaller than the width of the transmission aperture prevents measurement points distant from the ultrasound main irradiation area Ax from being included in the target area Bx, particularly at the transmission focal depth, and the consequent decrease in spatial resolution and signal S/N ratio. Further, making such a modification achieves generating a frame acoustic line signal through simple computation, as illustrated in the schematic of FIG. 25B.

Further, the modification of setting the target area Bx to include a part of the ultrasound main irradiation area Ax and a part corresponding to the outside of the ultrasound main irradiation area Ax is applicable also when the ultrasound main irradiation area Ax does not converge at one transmission focal point F but instead converges at a transmission focal area. Further, even when making this modification, modifications 2 through 4 are applicable, by setting the inside of the ultrasound main irradiation area Ax as a primary partial area Bx1 and the outside of the ultrasound main irradiation area Ax as a secondary partial area Bx2.

(3) While description is provided in embodiment 2 and modifications 2 through 4 that the synthesizer includes two adders and two amplifiers, the synthesizer need not have such a configuration. For example, the synthesizer may include one adder and one amplifier, in which case the adder and the amplifier first generate a primary frame part acoustic line signal from primary sub-frame acoustic line signals, and then generates a secondary frame part acoustic line signal from secondary sub-frame acoustic line signals.

Further, in embodiment 2 and modifications 2 through 4, the delay-and-sum calculator may include two each of all components other than the target area setter, in which case the delay-and-sum calculator performs the generation of the primary sub-frame acoustic line signal and the generation of the secondary sub-frame acoustic line signal in parallel.

Further, in each of the embodiments and modifications, a modification may be made such that the delay-and-sum calculator and the synthesizer are integrated, and the following set of processing is performed sequentially for every measurement point included in the frame: (i) delay-and-sum processing for generating an acoustic line signal for the measurement point; and (ii) combining of acoustic line signals for the measurement point that correspond to different transmission events. This modification achieves direct generation of a frame acoustic line signal from receive signals acquired through multiple transmission events corresponding to one frame, or that is, generation of a frame acoustic line signal without generating sub-frame acoustic lines signal each corresponding to one transmission event and covering the entirety of the target area for the corresponding transmission event. Note that even when making this modification, the combining (ii) is performed after the delay-and-sum processing (i) has been performed for each measurement point in the target area for each transmission event. Due to this, while there is a difference in whether sub-frame acoustic line signals each covering an entirety of a corresponding target area is generated, the combination of processing (i) and processing (ii) is basically similar to generating a frame acoustic line signal based on sub-frame acoustic line signals for the respective target areas.

(4) Up to this point, the technology pertaining to the present disclosure has been described based on specific embodiments and modifications thereof. However, the embodiments and modifications described above are non-limiting examples of application of the technology pertaining to the present disclosure, and thus, the technology pertaining to the present disclosure shall be construed to encompass the following exemplar modifications.

For example, the technology pertaining to the present disclosure may be implemented by using a computer system including a memory storing a computer program and a microprocessor operating based on the computer program. For example, the computer system may store a computer program of a diagnosis method of an ultrasound diagnostic device pertaining to the technology of the present disclosure, and the computer system may operate in accordance with the computer program or may provide instructions in accordance with the computer program to various components connected thereto.

Further, the technology pertaining to the present disclosure may be implemented by implementing a part of or the entirety of an ultrasound diagnostic device described above, or a part of or an entirety of an beam former described above by using a computer system including a microprocessor, a recording medium such as a ROM or a RAM, and a hard disk unit. In this implementation, a computer program achieving the same operations as a device described above is stored to the RAM or the hard disk unit. Further, in this implementation, various devices achieve their functions by the microprocessor operating in accordance with the computer program.

Further, the technology pertaining to the present disclosure may be implemented by implementing some or all components included in a device described above by using one system LSI (large scale integration). A system LSI is an ultra-multifunctional LSI manufactured by integrating multiple components onto one chip. Specifically, a system LSI is a computer system including a microprocessor, a ROM, a RAM, and the like. Further, each component may be separately implemented by using one chip, or some or all components may be implemented by using one chip. Note that LSIs are referred to by using different names, depending upon the level of integration achieved thereby. Such names include IC, system LSI, super LSI, and ultra LSI. In this implementation, a computer program achieving the same operations as any device described above is stored to the RAM. Further, in this implementation, the system LSI achieves its functions by the microprocessor operating in accordance with the computer program. For example, the technology pertaining to the present disclosure encompasses a form of implementation where an LSI stores a beam forming method pertaining to the present disclosure as a program, the LSI is inserted into a computer, and the computer executes the program (i.e., the beam forming method pertaining to the present disclosure).

Note that integration of circuits may be achieved by a dedicated circuit or a general purpose processor, in addition to being achievable by using an LSI as discussed above. Further, a Field Programmable Gate Array (FPGA), which is programmable after manufacturing, or a reconfigurable processor, which allows reconfiguration of the connection and setting of circuit cells inside the LSI, may be used.

Furthermore, if technology for circuit integration that replaces LSIs emerges, owing to advances in semiconductor technology or to another derivative technology, the integration of functional blocks may naturally be accomplished using such technology.

Further, some or all functions of an ultrasound diagnostic device discussed in the embodiments may be implemented by a processor such as a CPU executing a program. Further, the technology pertaining to the present disclosure may be implemented by using a non-transitory computer-readable recording medium having recorded thereon a program causing execution of a diagnostic method and a beam forming method of an ultrasound diagnostic device. Further, execution of the program by another independent computer system may be achieved by transferring the program by recording the program or a signal onto a recording medium. Naturally, the program may be distributed via means of transmission media such as the internet.

Each of the ultrasound diagnostic devices pertaining to the embodiments includes the data storage, which is a recording device. However, the recording device need not be included in the ultrasound diagnostic devices, and may be implemented by using a semiconductor memory, a hard disk drive, an optical disk drive, a magnetic storage device, or the like connected to the ultrasound diagnostic devices from the outside.

Further, the functional blocks illustrated in the block diagrams are mere examples of possible functional blocks. That is, a plurality of functional blocks illustrated in the block diagrams may be combined to form one functional block, a given functional block illustrated in the block diagrams may be divided into a plurality of functional blocks, and a function of a given functional block illustrated in the block diagrams may be transferred to another functional block. Further, with regards to multiple functional blocks having similar functions, such functional blocks may be implemented by one piece of hardware or software executing such functions in parallel or by applying time division.

Further, the above-described order in which steps of processing are executed is a non-limiting example among multiple possible orders that is used for the sole sake of providing specific description of the technology pertaining to the present disclosure. Further, some of the steps of processing described above may be executed simultaneously (in parallel).

Further, in the embodiments, description is provided that the ultrasound diagnostic devices may have a probe and a display attached thereto. However, the ultrasound diagnostic devices may include a probe and a display therein.

Further, in the embodiments, the probe includes a plurality of piezoelectric transducer elements forming a line in one direction. However, the probe may have a different structure. For example, the probe may include a plurality of piezoelectric transducer elements disposed two-dimensionally. Alternatively, the probe may be a swingable probe including a plurality of swingable transducer elements (i.e., transducer elements that can be caused to swing by mechanical means) forming a line in one direction, which enables acquisition of three-dimensional tomographic images. Further, probes of different types may be selected and used depending upon the examination to be performed. For example, when using a probe including piezoelectric transducer elements disposed two-dimensionally, supplying different piezoelectric transducer elements with voltages at different timings or with voltages with different values achieves controlling the position, the direction, etc., of the ultrasound beam to be transmitted.

Further, the probe may be provided with some of the functions of the transmission beam former/receive beam former. For example, the probe may be capable of generating a transmission electric signal based on a control signal that the transmission beam former/receive beam former outputs to cause generation of a transmission electric signal, and of converting the transmission electronic signal into ultrasound. In addition, the probe may be capable of converting reflected ultrasound into a receive electric signal, and of generating a receive signal based on the receive electric signal.

Further, at least some of the functions of the ultrasound diagnostic devices pertaining to the embodiments and the modifications may be combined with functions of other ones of the ultrasound diagnostic devices pertaining to the embodiments and the modifications. Further, the values used above are non-limiting examples used for the sole sake of providing specific description of the technology pertaining to the present disclosure, and may be replaced with other values.

Further, the technology pertaining to the present disclosure should be construed as encompassing various modifications that a skilled artisan would arrive at based on the embodiments describe above.

SUMMARY (1) One aspect of the present disclosure is an ultrasound signal processing device: performing a plurality of transmission events each involving selecting a first group of transducer elements from among a plurality of transducer elements of a ultrasound probe that are arranged in at least one line along a transducer element array direction, and causing each transducer element in the first group to transmit ultrasound towards a subject; for each of the transmission events, generating a sub-frame acoustic line signal based on ultrasound reflection received from the subject in response to the transmission event, to yield a plurality of sub-frame acoustic line signals each corresponding to a different one of the transmission events; and generating a frame acoustic line signal based on the sub-frame acoustic line signals for the transmission events. The ultrasound signal processing device includes ultrasound signal processing circuitry that operates as: a transmitter that, in each of the transmission events, selects the first group and causes each transducer element in the first group to transmit ultrasound focusing at a predetermined depth in the subject, the first group in one transmission event differing in position, in the transducer element array direction, from the first group in a previous transmission event by a shift amount corresponding to at least twice a width of a single transducer element in the transducer element array direction; a receiver that selects at least some transducer elements among the plurality of transducer elements of the ultrasound probe, and generates a receive signal sequence for each of the at least some transducer elements based on ultrasound reflection received by the transducer element; a delay-and-sum calculator that, for each of the transmission events: sets a target area including a plurality of measurement points, the target area at least including an area where the ultrasound transmitted from the first group in the transmission event focuses in the subject, wherein at the predetermined depth, a width of the target area in the transducer element array direction is equal to or greater than the shift amount; and generates a sub-frame acoustic line signal composed of a plurality of acoustic line signals, one for each measurement point included in the target area, by performing, for each measurement point that is included in the target area, delay-and-sum processing with respect to one or more receive signal sequences corresponding to the measurement point, the one or more receive signal sequences corresponding to the measurement point respectively generated for one or more transducer elements composing a second group of transducer elements, among the plurality of transducer elements of the ultrasound probe, based on ultrasound reflection received from the measurement point; and a synthesizer that generates a frame acoustic line signal based on a plurality of sub-frame acoustic line signals corresponding one-to-one with the transmission events.

This structure prevents the occurrence of defective areas in ultrasound images when combining the synthetic aperture method with conventional transmission beam forming, and thus enables increasing frame rate without image quality degradation.

(2) In the ultrasound signal processing device of (1), for each of the transmission events, the delay-and-sum calculator may set, as the target area, a combination of: a first area having an hourglass shape, having a base corresponding in position to the first group in the transmission event, and having minimum width in the transducer element array direction at the predetermined depth, the minimum width being smaller than the shift amount; and a second area adjacent to the first area in the transducer element array direction at least at and around the predetermined depth.

This structure provides an enlarged target area whose width in the transducer element array direction is equal to or greater than the shift amount, by including a first area that covers an area in which transmitted ultrasound is in-phase and a second area that covers an outside of the area in which transmitted ultrasound is in-phase.

(3) In the ultrasound signal processing device of (2), for each measurement point, the delay-and-sum calculator may perform the delay-and-sum processing by using delay amounts for the respective transducer elements composing the second group, a delay amount for a given one of the transducer elements composing the second group being based on a total propagation time being a total of a transmission time being a time amount required for transmitted ultrasound to arrive at the measurement point and a receive time being a time amount required for ultrasound reflection from the measurement point to arrive at the transducer element.

This structure enables a sub-frame acoustic line signal to be generated by performing delay-and-sum processing for each measurement point in the target area.

(4) In the ultrasound signal processing device of (3), for each measurement point included in the first area, the delay-and-sum calculator may use, as the transmission time, a first arrival time that is calculated by using a first time amount and a second time amount and that changes depending upon a depth of the measurement point, the first time amount being a time amount required for transmitted ultrasound to arrive at a reference point included in the first area and at the predetermined depth, the second time amount being a time amount required for transmitted ultrasound to arrive at the measurement point from the reference point, and for each measurement point included in the first area and deeper than the predetermined depth, the first arrival time may be calculated by summing the first time amount and the second time amount, and for each measurement point included in the first area and shallower than the predetermined depth, the first arrival time may be calculated by subtracting the second time amount from the first time amount.

This structure enables a sub-frame acoustic line signal to be generated by performing delay-and-sum processing for each measurement point in the first area by calculating a transmission time based on a distance from a transmission focal point.

(5) In the ultrasound signal processing device of (4), for each measurement point included in the second area, the delay-and-sum calculator may use the first arrival time as the transmission time, and for each measurement point included in the second area and deeper than the predetermined depth, the first arrival time may be calculated by summing the first time amount and the second time amount, and for each measurement point included in the second area and shallower than the predetermined depth, the first arrival time may be calculated by subtracting the second time amount from the first time amount.

This structure enables a sub-frame acoustic line signal to be generated by performing delay-and-sum processing for each measurement point in the second area by calculating a transmission time based on a distance from a transmission focal point.

(6) In the ultrasound signal processing device of (4), for at least each measurement point at the predetermined depth, among a plurality of measurements included in the second area, the delay-and-sum calculator may use, as the transmission time, a time amount required for transmitted ultrasound to travel though any path from a transducer element of the first group to a point at the same depth as the measurement point.

This structure avoids discontinuity in the change of transmission times for measurement points in the second area, which would otherwise occur due to a distance between measurement points at the transmission focal depth and the transmission focal point, and improves ultrasound image quality.

(7) In the ultrasound signal processing device of (6), for each of the measurement points included in the second area, the delay-and-sum calculator may use, as the transmission time, a time amount required for transmitted ultrasound to travel through a path from a transducer element of the first group that is located at a center position of the first group in the transducer element array direction to the measurement point.

This structure enables calculating transmission times for measurement points in the second area according to a method that does not depend upon the transmission focal point.

(8) In the ultrasound signal processing device of (6), among measurement points in the second area that are located along each of at least one line perpendicular to the transducer element array direction, for each boundary point located in a periphery of a boundary between the first and second areas, the delay-and-sum calculator may use the first arrival time as the transmission time, wherein for a boundary point deeper than the predetermined depth, the first arrival time may be calculated by summing the first time amount and the second time amount, and for a boundary point shallower than the predetermined depth, the first arrival time may be calculated by subtracting the second time amount from the first time amount, for an intermediate point being one of the measurement points that is located at the predetermined depth, the delay-and-sum calculator may use, as the transmission time, a second arrival time being a time amount required for transmitted ultrasound to travel though any path from a transducer element of the first group to a point at the same depth as the intermediate point, and for a plurality of measurement point between the boundary point and the intermediate point, the delay-and-sum calculator may set respective transmission times so that the transmission times monotonically increase as measurement point depth increases, without any discontinuity between the transmission times.

This structure ensures that, for measurement points in the target area that are located along a straight line perpendicular to the transducer element array direction, transmission time monotonically increases without discontinuity as depth increases. Thus, this structure improves ultrasound image quality pertaining to the second area and a boundary between the first area and the second area.

(9) In the ultrasound signal processing device of (8), for each of the measurement points included in the second area, the delay-and-sum calculator may set the transmission time according to $T_M = \alpha T_1 + (1-\alpha) T_2$ where $T_M$ denotes the transmission time for the measurement point, $T_1$ denotes the first arrival time, and $T_2$ denotes the second arrival time, and where variable $\alpha=0$ for the intermediate point, $\alpha=1$ for the boundary point, and a increases without discontinuity as a difference between measurement point depth and the predetermined depth increases.

This structure ensures, with a simple method, calculating transmission times for measurement points in the target area that are located along a straight line perpendicular to the transducer element array direction so that transmission time monotonically increases without discontinuity as depth increases.

(10) In the ultrasound signal processing device of (2), for two consecutive transmission events, the delay-and-sum calculator may set two target areas respectively corresponding to the two consecutive transmission events so that the second areas of the two target areas partially overlap one another in the transducer element array direction.

This structure ensures a maximum overlap count of at least two within the second area, and thus improves ultrasound image quality pertaining to the second area.

(11) In the ultrasound signal processing device of (10), the second areas of the two target areas respectively corresponding to the two consecutive transmission events may overlap one another by at least 50% in terms of area.

This structure ensures an overlap count of at least two within at least 50% of each second area, and thus improves ultrasound image quality pertaining to second areas.

(12) In the ultrasound signal processing device of (2), the delay-and-sum calculator may generate a sub-frame acoustic line signal for the first area and a sub-frame acoustic line signal for the second area, and the synthesizer may combine a plurality of sub-frame acoustic line signals for the first area that correspond one-to-one with the transmission events to generate a first combined acoustic line signal, and combine a plurality of sub-frame acoustic line signals for the second area that correspond one-to-one with the transmission events to generate a second combined acoustic line signal, and generate the frame acoustic line signal by combining the first combined acoustic line signal and the second combined acoustic line signal.

This structure avoids the first area and the second area from affecting one another in terms of image quality, and thus improves ultrasound image quality.

(13) In the ultrasound signal processing device of (1), the ultrasound signal processing circuitry may further operate as: an amplifier that amplifies each sub-frame acoustic line signal by using amplification factors corresponding one-to-one with the measurement points included in the target area, an amplification factor for a given measurement point determined based on the number of signals combined to generate the acoustic line signal for the measurement point.

This structure avoids a difference in overlap count between measurement points from affecting image quality, and thus improves ultrasound image quality.

(14) Another aspect of the present disclosure is an ultrasound signal processing device: performing a plurality of transmission events each involving selecting a first group of transducer elements from among a plurality of transducer elements of a ultrasound probe that are arranged in at least one line along a transducer element array direction, and causing each transducer element in the first group to transmit ultrasound towards a subject; for each of the transmission events, generating a sub-frame acoustic line signal based on ultrasound reflection received from the subject in response to the transmission event, to yield a plurality of sub-frame acoustic line signals each corresponding to a different one of the transmission events; and generating a frame acoustic line signal based on the sub-frame acoustic line signals for the transmission events. The ultrasound signal processing device includes ultrasound signal processing circuitry that operates as: a transmitter that, in each of the transmission events, selects the first group and causes each transducer element in the first group to transmit ultrasound focusing at a predetermined depth in the subject, the first group shifting in the transducer element array direction from one transmission event to another; a receiver that selects at least some transducer elements among the plurality of transducer elements of the ultrasound probe, and generates a receive signal sequence for each of the at least some transducer elements based on ultrasound reflection received by the transducer element; a delay-and-sum calculator that, for each of the transmission events: sets a target area including a plurality of measurement points, the target area at least including an area where the ultrasound transmitted from the first group in the transmission event focuses in the subject, wherein at the predetermined depth, a width of the target area in the transducer element array direction greater than a width of a single transducer element in the transducer element array direction; and generates a sub-frame acoustic line signal composed of a plurality of acoustic line signals, one for each measurement point included in the target area, by performing, for each measurement point that is included in the target area, delay-and-sum processing with respect to one or more receive signal sequences corresponding to the measurement point, the one or more receive signal sequences corresponding to the measurement point respectively generated for one or more transducer elements composing a second group of transducer elements, among the plurality of transducer elements of the ultrasound probe, based on ultrasound reflection received from the measurement point; and a synthesizer that generates a frame acoustic line signal based on a plurality of sub-frame acoustic line signals corresponding one-to-one with the transmission events.

This structure improves image quality at areas in ultrasound images where two consecutive transmission events overlap, even when the shift amount is set to a width of a single transducer element.

(15) Another aspect of the present disclosure is an ultrasound diagnostic device including the ultrasound signal processing device of (1). In the ultrasound diagnostic device, the ultrasound signal processing device may be configured so that the ultrasound probe is connectable thereto.

This structure achieves an ultrasound diagnostic device having the above-described features.

Although the technology pertaining to the present disclosure has been fully described by way of examples with reference to the accompanying drawings, it is to be noted that various changes and modifications will be apparent to those skilled in the art. Therefore, unless such changes and modifications depart from the scope of the present disclosure, they should be construed as being included therein.

What is claimed is:

1. An ultrasound diagnostic device comprising:
   an ultrasound probe including transducer elements; and
   an ultrasound diagnostic circuit that functions as:
   a transmitter performing an ultrasound transmission event of causing a transmission transducer element array composed of all or some of the transducer elements to transmit ultrasound;
   a receiver generating reception signal sequences, one for each of the transducer elements of a reception transducer element array composed of all or some of the transducer elements, each of the reception signal sequences generated according to a signal based on reflected ultrasound that a corresponding one of the transducer elements receives in response to the transmission of the ultrasound;
   a delay amount generator generating delay amounts, one for each of the transducer elements of the reception transducer element array; and
   a delay processor performing delay processing on the reception signal sequences, based on the delay amounts, wherein
   the delay amount generator includes:
   a transmission time generator generating only once, for a measurement point within an area of reach of the ultrasound of the ultrasound transmission event, a transmission time that is a time period from transmission of the ultrasound until arrival of the ultrasound at the measurement point; and
   a reception time generator generating reception times, one for each of the transducer elements in the reception transducer element array, the reception times each being a time period from reflection of the ultrasound at the measurement point until arrival of the ultrasound at the transducer element, wherein
   the delay amount generator generates the delay amounts based on the transmission time and the reception times, and the transmission time generator,
when distance from a transmission reference point to the measurement point is greater than distance from the transmission reference point to a focal point, generates the transmission time based on a sum of time for transmitted ultrasound to arrive at the focal point from the transmission reference point and time for transmitted ultrasound to arrive at the measurement point from the focal point, and
when distance from the transmission reference point to the measurement point is smaller than distance from the transmission reference point to the focal point, generates the transmission time based on subtracting time for transmitted ultrasound to arrive at the measurement point from the focal point from time for transmitted ultrasound to arrive at the focal point from the transmission reference point.

2. An ultrasound diagnostic device comprising:
an ultrasound probe including transducer elements; and
an ultrasound diagnostic circuit that functions as:
a transmitter performing an ultrasound transmission event of causing a transmission transducer element array composed of all or some of the transducer elements to transmit ultrasound;
a receiver generating reception signal sequences, one for each of the transducer elements of a reception transducer element array composed of all or some of the transducer elements, each of the reception signal sequences generated according to a signal based on reflected ultrasound that a corresponding one of the transducer elements receives in response to the transmission of the ultrasound;
a delay amount generator generating delay amounts, one for each of the transducer elements of the reception transducer element array; and
a delay processor performing delay processing on the reception signal sequences, based on the delay amounts, wherein
the delay amount generator includes:
a transmission time generator generating only once, for a measurement point within an area of reach of the ultrasound of the ultrasound transmission event, a transmission time that is a time period from transmission of the ultrasound until arrival of the ultrasound at the measurement point; and
a reception time generator generating reception times, one for each of the transducer elements in the reception transducer element array, the reception times each being a time period from reflection of the ultrasound at the measurement point until arrival of the ultrasound at the transducer element, wherein
the delay amount generator generates the delay amounts based on the transmission time and the reception times, and
the transmission time generator,
when the measurement point is farther from the transmission transducer element array than a focal point is,
generates the transmission time based on a sum of time for transmitted ultrasound to arrive at the focal point from the transmission reference point and time for transmitted ultrasound to arrive at the measurement point from the focal point, and
when the measurement point is closer to the transmission transducer element array than the focal point is,
generates the transmission time based on subtracting time for transmitted ultrasound to arrive at the measurement point from the focal point from time for transmitted ultrasound to arrive at the focal point from the transmission reference point.

3. The ultrasound diagnostic device of claim 1, wherein the delay processor identifies, for each transducer element of the reception transducer element array, a reception signal value corresponding to a delay amount from the reception signal sequences, and generates an acoustic line signal for the measurement point based on the reception signal values identified.

4. The ultrasound diagnostic device of claim 3, wherein the transmission event is performed a plurality of times,
the transmission time generator generates the transmission time to the measurement point only once for each transmission event, and
the delay processor generates an acoustic line signal for the measurement point, based on the reception signal sequences for each of the transducer elements of the reception transducer element array of each transmission event.

5. The ultrasound diagnostic device of claim 1, wherein the reception time generator generates the reception times based on distances between the measurement point and the transducer elements of the reception transducer element array.

6. The ultrasound diagnostic device of claim 1, wherein the delay amount generator generates the delay amounts for each of the transducer elements of the reception transducer element array by adding the transmission time to the reception times for each of the transducer elements of the reception transducer element array.

7. The ultrasound diagnostic device of claim 1, wherein the receiver generates the reception signal sequences according to signals based on reflected ultrasound that the transducer elements receive from inside a subject in response to the transmission of the ultrasound, and
the measurement point is set inside the subject.

8. An ultrasound diagnostic method comprising:
performing an ultrasound transmission event of causing a transmission transducer element array composed of all or some transducer elements of an ultrasound probe to transmit ultrasound;
generating reception signal sequences, one for each of the transducer elements of a reception transducer element array composed of all or some of the transducer elements, each of the reception signal sequences generated according to a signal based on reflected ultrasound that a corresponding one of the transducer elements receives in response to the transmission of the ultrasound;
generating delay amounts, one for each of the transducer elements of the reception transducer element array; and
performing delay processing on the reception signal sequences, based on the delay amounts, wherein
the delay amount generating includes:
generating only once, for a measurement point within an assumed area of reach of the ultrasound of the ultrasound transmission event, a transmission time that is a time period from transmission of the ultrasound until arrival of the ultrasound at the measurement point; and
generating reception times, one for each of the transducer elements in the reception transducer element array, the reception times each being a time period from reflection of the ultrasound at the measurement point until arrival of the ultrasound at the transducer element, wherein the delay amount generating generates the delay amounts based on the transmission time and the reception times, and the transmission time generating,
when distance from a transmission reference point to the measurement point is greater than distance from the transmission reference point to a focal point,
generates the transmission time based on a sum of time for transmitted ultrasound to arrive at the focal point from the transmission reference point and time for transmitted ultrasound to arrive at the measurement point from the focal point, and
when distance from the transmission reference point to the measurement point is smaller than distance from the transmission reference point to the focal point,
generates the transmission time based on subtracting time for transmitted ultrasound to arrive at the measurement point from the focal point from time for transmitted ultrasound to arrive at the focal point from the transmission reference point.

9. An ultrasound diagnostic method comprising:
performing an ultrasound transmission event of causing a transmission transducer element array composed of all or some transducer elements of an ultrasound probe to transmit ultrasound;
generating reception signal sequences, one for each of the transducer elements of a reception transducer element array composed of all or some of the transducer elements, each of the reception signal sequences generated according to a signal based on reflected ultrasound that a corresponding one of the transducer elements receives in response to the transmission of the ultrasound;
generating delay amounts, one for each of the transducer elements of the reception transducer element array; and
performing delay processing on the reception signal sequences, based on the delay amounts, wherein
the delay amount generating includes:
generating only once, for a measurement point within an assumed area of reach of the ultrasound of the ultrasound transmission event, a transmission time that is a time period from transmission of the ultrasound until arrival of the ultrasound at the measurement point; and
generating reception times, one for each of the transducer elements in the reception transducer element array, the reception times each being a time period from reflection of the ultrasound at the measurement point until arrival of the ultrasound at the transducer element, wherein
the delay amount generating generates the delay amounts based on the transmission time and the reception times, and the transmission time generating,
when the measurement point is farther from the transmission transducer element array than a focal point is,
generates the transmission time based on a sum of time for transmitted ultrasound to arrive at the focal point from the transmission reference point and time for transmitted ultrasound to arrive at the measurement point from the focal point, and
when the measurement point is closer to the transmission transducer element array than the focal point is,
generates the transmission time based on subtracting time for transmitted ultrasound to arrive at the measurement point from the focal point from time for transmitted ultrasound to arrive at the focal point from the transmission reference point.

10. The ultrasound diagnostic method of claim 8, wherein in the delay processing, for each transducer element of the reception transducer element array, a reception signal value corresponding to a delay amount is identified from the reception signal sequences, and an acoustic line signal for the measurement point is generated based on the reception signal values identified.

11. The ultrasound diagnostic method of claim 10, wherein
the transmission event is performed a plurality of times,
the transmission time generating generates the transmission time to the measurement point only once for each transmission event, and
the delay processing generates an acoustic line signal for the measurement point, based on the reception signal sequences for each of the transducer elements of the reception transducer element array of each transmission event.

12. The ultrasound diagnostic method of claim 8, wherein the reception time generating generates the reception times based on distances between the measurement point and the transducer elements of the reception transducer element array.

13. The ultrasound diagnostic method of claim 8, wherein the delay amount generating generates the delay amounts for each of the transducer elements of the reception transducer element array by adding the transmission time to the reception times for each of the transducer elements of the reception transducer element array.

14. The ultrasound diagnostic method of claim 8, wherein the reception signal sequences are generated according to signals based on reflected ultrasound that the transducer elements receive from inside a subject in response to the transmission of the ultrasound, and
the measurement point is set inside the subject.

* * * * *